United States Patent [19]

Biller et al.

[11] Patent Number: 5,885,983

[45] Date of Patent: Mar. 23, 1999

[54] INHIBITORS OF MICROSOMAL TRIGLYCERIDE TRANSFER PROTEIN AND METHOD

[75] Inventors: Scott A. Biller, Hopewell; John K. Dickson, Jr., Eastampton, both of N.J.

[73] Assignee: Bristol-Myers Squibb Company, Princeton, N.J.

[21] Appl. No.: 847,775

[22] Filed: Apr. 23, 1997

Related U.S. Application Data

[60] Provisional application No. 60/017,254, May 10, 1996.

[51] Int. Cl.$^6$ ............... A61K 31/395; A61K 31/41; A61K 31/435; A61K 31/495; C07D 205/04

[52] U.S. Cl. ............... 514/210; 514/235.5; 514/248; 514/252; 514/290; 514/292; 514/314; 514/340; 514/367; 514/374; 514/378; 514/397; 514/403; 514/406; 514/414; 548/180; 548/215; 548/248; 548/314; 548/362.5; 548/364.1; 548/467; 548/930; 548/935; 546/85; 546/111; 546/156; 546/169; 546/268.1; 544/168; 544/235; 544/238; 544/277; 544/406; 544/407

[58] Field of Search ............... 548/930, 935, 548/180, 362.5, 364.1, 467, 215, 248, 314; 546/156, 169, 268.1, 85, 111; 544/238, 168, 406, 407, 235, 277; 514/340, 314, 367, 403, 252, 397, 235.5, 290, 292, 248, 266, 374, 378, 406, 414, 210

[56] References Cited

U.S. PATENT DOCUMENTS

| | | | |
|---|---|---|---|
| 3,910,931 | 10/1975 | Cavalla et al. | 260/293.62 |
| 4,123,527 | 10/1978 | Melloni | 424/244 |
| 4,289,781 | 9/1981 | Bengtsson et al. | 424/267 |
| 4,367,232 | 1/1983 | Boix-Igleasias et al. | 424/267 |
| 4,576,940 | 3/1986 | Tahara et al. | 514/212 |
| 4,581,355 | 4/1986 | Tahara et al. | 514/212 |
| 4,607,042 | 8/1986 | Pierce | 514/323 |
| 4,826,975 | 5/1989 | Picciola et al. | 544/391 |
| 5,026,858 | 6/1991 | Vega-Noverola et al. | 546/224 |
| 5,028,616 | 7/1991 | Desai et al. | 514/321 |
| 5,032,598 | 7/1991 | Baldwin et al. | 514/318 |
| 5,087,621 | 2/1992 | Pinol | 514/210 |
| 5,098,915 | 3/1992 | Desai et al. | 514/324 |
| 5,130,333 | 7/1992 | Pan et al. | 514/460 |
| 5,189,045 | 2/1993 | Peglion et al. | 514/319 |
| 5,212,182 | 5/1993 | Musser et al. | 514/314 |
| 5,215,989 | 6/1993 | Baldwin et al. | 514/252 |
| 5,292,883 | 3/1994 | Martin et al. | 546/201 |
| 5,410,057 | 4/1995 | Baroni | 544/334 |
| 5,527,801 | 6/1996 | Masuda et al. | 514/255 |

FOREIGN PATENT DOCUMENTS

| | | |
|---|---|---|
| 0584446A2 | 3/1994 | European Pat. Off. |
| 0643057A1 | 3/1995 | European Pat. Off. |
| 49109369 | 10/1974 | Japan |
| WO93/05778 | 9/1991 | WIPO |
| WO96/40640 | 12/1996 | WIPO |

OTHER PUBLICATIONS

Frigola J et al. J. Med. Chem. 36(7), 801–10, 1993.

Nisato D and Frigerio M. J. Heterocycl. Chem. 22(4), 961–3, 1985.

Masuda K et al. Takeda Kenkyusho Ho. 31(4), 453–9, 1972.

Hirata M et al. Takeda Kenkyusho Ho. 31(2), 206–20, 1972.

Chen TY et al. Bull. Chem. Soc. Jap. 41(3), 712–6, 1968.

Melloni P et al. J. Med. Chem. 22(2), 183–91, 1978.

Bulleid & Freedman, Nature 335, 649–651 (1988). "Defective co–translational formation of disulphide bonds in protein disulphideisomerase–deficient microsomes".

Koivu et al., J. Biol. Chem. 262, 6447–6449 (1987). "A Single Polypeptide Acts Both as the β Subunit of Prolyl 4–Hydroxylase and as a Protein Disulfide–Isomerase*".

Kane & Havel in the Metabolic Basis of Inherited Disease, Sixth Edition, 1139–1164 (1989). "Disorders of the Biogenesis and Secretion of Lipoproteins Containing The B Apolipoproteins".

Schaefer et al., Clin. Chem. 34, B9–B12 (1988), "Genetics and Abnormalties in Metabolism of Lipoproteins".

Drayna et al., Nature 327, 632–634 (1987). "Cloning and sequencing of human cholesteryl ester transfer protein cDNA.".

Pihlajaniemi et al., EMBO J. 6, 643–649 (1987). "Molecular cloning of the β–subunit of human prolyl–4–hydroxylase. This subunit and protein disulphide isomerase are products of the same gene".

Yamaguchi et al., Biochem. Biophys. Res. Comm. 146, 1485–1492 (1987). "Sequence of Membrane–Associated Thyroid Hormone Binding Protein From Bovine Liver: Its Identity with Protein Disulphide Isomerase".

Edman et al., Nature 317, 267–270 (1985). Sequence of protein disulphide isomerase and implications of its relationship to thioredoxin.

Kao et al., Connective Tissue Research 18, 157–174 (1988). "Isolation of cDNA Clones and Genomic DNA Clones of β–Subunit of Chicken Proplyl 4–Hydroxylase*".

Wetterau, J. et al., Biochem 30, 9728–9735 (1991). "Protein Disulfide Isomerase Appears Necessary To Maintain the Catalytically Active Structure of the Microsomal Triglyceride Transfer Protein".

(List continued on next page.)

Primary Examiner—Evelyn Huang
Attorney, Agent, or Firm—Burton Rodney

[57] ABSTRACT

Compounds are provided which inhibit microsomal triglyceride transfer protein and thus are useful for lowering serum lipids and treating atherosclerosis and related diseases. The compounds have the structure

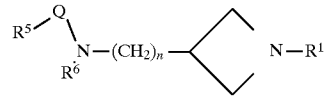

wherein $R^1$ to $R^6$, Q, and X are as defined herein.

15 Claims, No Drawings

OTHER PUBLICATIONS

Morton, R.E. et al., J. Biol. Chem. 256, 1992–1995 (1981), "A Plasma Inhibitor of Triglyceride and Chloesteryl Ester Transfer Activities".

Wetterau, J. et al., Biochem: 30, 4406–4412 (1991): "Structural Properties of the Microsomal Triglyceride–Transfer Protein Complex".

Wetterau, J. et al., J. Biol. Chem. 265, 9800–9807 (1990). "Protein Disulfide Isomerase Is a Component of the Microsomal Triglyceride Transfer Protein Complex".

Wetterau, J. and Zilversmit, D.B., Chem., and Phys. of Lipids 38, 205–22 (1985). "Purification and Characterization of Microsomal Triglyceride and Cholesteryl Ester Transfer Protein From Bovine Liver Microsomes".

Wetterau, J. and Zilversmit, D.B., Biochimicia et Biophysica Acta 875, 610–617 (1986). "Localization of intracellular triacylglycerol and cholesteryl ester transfer activity in rat tissues".

Wetterau, J. and Zilversmit, D.B., J. Biol. Chem. 259, 10863–10866 (1984) "A Triglyceride and Cholesteryl Ester Transfer Protein Associated with Liver Microsomes".

Wetterau, J., Grant Application entitled: "Intracellular Triglyceride Transport and Metabolism".

Presentation Materials, Aspen Bile Acid/Cholesterol Conference, Aug. 15, 1992.

Wetterau, J. R., et al., Science, vol. 258, 999–1001, Nov. 6, 1992, "Absence of Microsomal Triglyceride Transfer Protein in Individuals with Abetalipoproteinemia".

Archibald, J. L., et al., Journal of Medicinal Chemistry, vol. 14, No. 11, pp. 1054–1059.

Cortizo, L. et al., J. Med. Chem., 34, pp. 2242–2247, 1991.

Hall, I. H. et al., Pharmaceutical Research, vol. 9, No. 10, pp. 1324–1329, 1992.

Hall, I. H., et al., Pharmacological Research Communications, vol. 19, No. 12, pp. 839–858, 1987.

Murthy et al., Eur. J. Med. Chem.—Chim. Ther., vol. 20, No. 6, pp. 547–550, 1985.

INHIBITORS OF MICROSOMAL TRIGLYCERIDE TRANSFER PROTEIN AND METHOD

This application claims the benefit of the provisional application 60/017254, filed on May 10, 1996.

FIELD OF THE INVENTION

This invention relates to novel compounds which inhibit microsomal triglyceride transfer protein, and to methods for decreasing serum lipids and treating atherosclerosis employing such compounds.

BACKGROUND OF THE INVENTION

The microsomal triglyceride transfer protein (MTP) catalyzes the transport of triglyceride (TG), cholesteryl ester (CE), and phosphatidylcholine (PC) between small unilamellar vesicles (SUV). Wetterau & Zilversmit, Chem. Phys. Lipids 38, 205–22 (1985). When transfer rates are expressed as the percent of the donor lipid transferred per time, MTP expresses a distinct preference for neutral lipid transport (TG and CE), relative to phospholipid transport. The protein from bovine liver has been isolated and characterized. Wetterau & Zilversmit, Chem. Phys. Lipids 38, 205–22 (1985). Polyacrylamide gel electrophoresis (PAGE) analysis of the purified protein suggests that the transfer protein is a complex of two subunits of apparent molecular weights 58,000 and 88,000, since a single band was present when purified MTP was electro-phoresed under nondenaturing condition, while two bands of apparent molecular weights 58,000 and 88,000 were identified when electrophoresis was performed in the presence of sodium dodecyl sulfate (SDS). These two polypeptides are hereinafter referred to as 58 kDa and 88 kDa, respectively, or the 58 kDa and the 88 kDa component of MTP, respectively, or the low molecular weight subunit and the high molecular weight subunit of MTP, respectively.

Characterization of the 58,000 molecular weight component of bovine MTP indicates that it is the previously characterized multifunctional protein, protein disulfide isomerase (PDI). Wetterau et al., J. Biol. Chem. 265, 9800–7 (1990). The presence of PDI in the transfer protein is supported by evidence showing that (1) the amino terminal 25 amino acids of the bovine 58,000 kDa component of MTP is identical to that of bovine PDI, and (2) disulfide isomerase activity was expressed by bovine MTP following the dissociation of the 58 kDa–88 kDa protein complex. In addition, antibodies raised against bovine PDI, a protein which by itself has no TG transfer activity, were able to immunoprecipitate bovine TG transfer activity from a solution containing purified bovine MTP.

PDI normally plays a role in the folding and assembly of newly synthesized disulfide bonded proteins within the lumen of the endoplasmic reticulum. Bulleid & Freedman, Nature 335, 649–51 (1988). It catalyzes the proper pairing of cysteine residues into disulfide bonds, thus catalyzing the proper folding of disulfide bonded proteins. In addition, PDI has been reported to be identical to the beta subunit of human prolyl 4-hydroxylase. Koivu et al., J. Biol. Chem. 262, 6447–9 (1987). The role of PDI in the bovine transfer protein is not clear. It does appear to be an essential component of the transfer protein as dissociation of PDI from the 88 kDa component of bovine MTP by either low concentrations of a denaturant (guanidine HCl), a chaotropic agent (sodium perchlorate), or a nondenaturing detergent (octyl glucoside) results in a loss of transfer activity. Wetterau et al., Biochemistry 30, 9728–35 (1991). Isolated bovine PDI has no apparent lipid transfer activity, suggesting that either the 88 kDa polypeptide is the transfer protein or that it confers transfer activity to the protein complex.

The tissue and subcellular distribution of MTP activity in rats has been investigated. Wetterau & Zilversmit, Biochem. Biophys. Acta 875, 610–7 (1986). Lipid transfer activity was found in liver and intestine. Little or no transfer activity was found in plasma, brain, heart, or kidney. Within the liver, MTP was a soluble protein located within the lumen of the microsomal fraction. Approximately equal concentrations were found in the smooth and rough microsomes.

Abetalipoproteinemia is an autosomal recessive disease characterized by a virtual absence of plasma lipoproteins which contain apolipoprotein B (apoB). Kane & Havel in The Metabolic Basis of Inherited Disease, Sixth Edition, 1139–64 (1989). Plasma TG levels may be as low as a few mg/dL, and they fail to rise after fat ingestion. Plasma cholesterol levels are often only 20–45 mg/dL. These abnormalities are the result of a genetic defect in the assembly and/or secretion of very low density lipoproteins (VLDL) in the liver and chylomicrons in the intestine. The molecular basis for this defect has not been previously determined. In subjects examined, triglyceride, phospholipid, and cholesterol synthesis appear normal. At autopsy, subjects are free of atherosclerosis. Schaefer et al., Clin. Chem. 34, B9–12 (1988). A link between the apoB gene and abetalipoproteinemia has been excluded in several families. Talmud et al., J. Clin. Invest. 82, 1803–6 (1988) and Huang et al., Am. J. Hum. Genet. 46, 1141–8 (1990).

Subjects with abetalipoproteinemia are afflicted with numerous maladies. Kane & Havel, supra. Subjects have fat malabsorption and TG accumulation in their enterocytes and hepatocytes. Due to the absence of TG-rich plasma lipoproteins, there is a defect in the transport of fat-soluble vitamins such as vitamin E. This results in acanthocytosis of erythrocytes, spinocerebellar ataxia with degeneration of the fasciculus cuneatus and gracilis, peripheral neuropathy, degenerative pigmentary retinopathy, and ceroid myopathy. Treatment of abetalipoproteinemic subjects includes dietary restriction of fat intake and dietary supplementation with vitamins A, E and K.

In vitro, MTP catalyzes the transport of lipid molecules between phospholipid membranes. Presumably, it plays a similar role in vivo, and thus plays some role in lipid metabolism. The subcellular (lumen of the microsomal fraction) and tissue distribution (liver and intestine) of MTP have led to speculation that it plays a role in the assembly of plasma lipoproteins, as these are the sites of plasma lipoprotein assembly. Wetterau & Zilversmit, Biochem. Biophys. Acta 875, 610–7 (1986). The ability of MTP to catalyze the transport of TG between membranes is consistent with this hypothesis, and suggests that MTP may catalyze the transport of TG from its site of synthesis in the endoplasmic reticulum (ER) membrane to nascent lipoprotein particles within the lumen of the ER.

Olofsson and colleagues have studied lipoprotein assembly in HepG2 cells. Bostrom et al., J. Biol. Chem. 263, 4434–42 (1988). Their results suggest small precursor lipoproteins become larger with time. This would be consistent with the addition or transfer of lipid molecules to nascent lipoproteins as they are assembled. MTP may play a role in this process. In support of this hypothesis, Howell and Palade, J. Cell Biol. 92, 833–45 (1982), isolated nascent lipoproteins from the hepatic Golgi fraction of rat liver. There was a spectrum of sizes of particles present with varying lipid and protein compositions. Particles of high density lipoprotein (HDL) density, yet containing apoB, were found. Higgins and Hutson, *J. Lipid Res.* 25, 1295–1305 (1984), reported lipoproteins isolated from Golgi were consistently larger than those from the endoplasmic reticulum, again suggesting the assembly of lipoproteins is a progressive event.

Recent reports (Science, Vol. 258, page 999, 1992; D. Sharp et. al., Nature, Vol. 365, page 65, 1993) demonstrate that the defect causing abetalipoproteinemia is in the MTP gene, and as a result, the MTP protein. Individuals with abetalipoproteinemia have no MTP activity, as a result of mutations in the MTP gene, some of which have been characterized. These results indicate that MTP is required for the synthesis of apoB containing lipoproteins, such as VLDL, the precursor to LDL. It therefore follows that inhibitors of MTP would inhibit the synthesis of VLDL and LDL, thereby lowering VLDL levels, LDL levels, cholesterol levels, and triglyceride levels in animals and man.

Canadian Patent Application No. 2,091,102 published Mar. 2, 1994 (corresponding to U.S. application Ser. No. 117,362, filed Sep. 3, 1993 (file DC21b)), U.S. Pat. No. 5,595,872 reports MTP inhibitors which also block the production of apoB containing lipoproteins in a human hepatic cell line (HepG2 cells). This provides further support for the proposal that an MTP inhibitor would lower apoB containing lipoprotein and lipid levels in vivo. This Canadian patent application discloses a method for identifying the MTP inhibitors

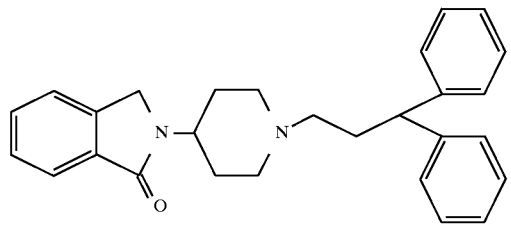

which has the name 2-[1-(3, 3-diphenylpropyl)-4-piperidinyl]-2, 3-dihydro-3-oxo-1H-isoindole hydrochloride and

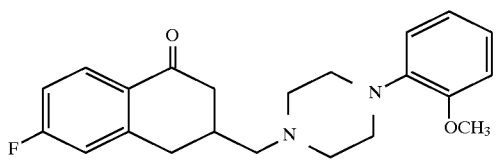

which has the name 1-[3-(6-fluoro-1-tetralanyl)methyl]-4-O-methoxyphenyl piperazine EP 0643057A1 published Mar. 15, 1995, discloses MTP inhibitors of the structure

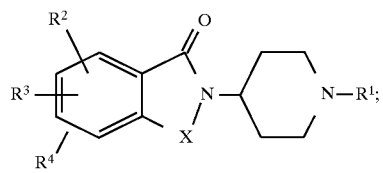

or

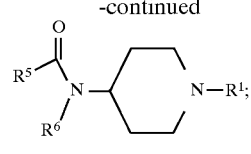

or

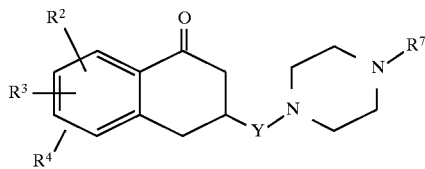

where

X is:

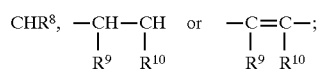

$R^8$, $R^9$ and $R^{10}$ are independently hydrogen, alkyl, alkenyl, alkynyl, aryl, arylalkyl, heteroaryl, heteroarylalkyl, cycloalkyl, or cycloalkylalkyl;

Y is

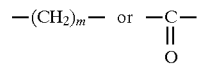

where m is 2 or 3;

$R^1$ is alkyl, alkenyl, alkynyl, aryl, heteroaryl, arylalkyl (wherein alkyl has at least 2 carbons), diarylalkyl, arylalkenyl, diarylalkenyl, arylalkynyl, diarylalkynyl, diarylalkylaryl, heteroarylalkyl (wherein alkyl has at least 2 carbons), cycloalkyl, or cycloalkylalkyl (wherein alkyl has at least 2 carbons); all of the aforementioned $R^1$ groups being optionally substituted through available carbon atoms with 1, 2, or 3 groups selected from halo, haloalkyl, alkyl, alkenyl, alkoxy, aryloxy, aryl, arylalkyl, alkyl-mercapto, arylmercapto, cycloalkyl, cycloalkyl-alkyl, heteroaryl, fluorenyl, heteroarylalkyl, hydroxy or oxo; or $R^1$ is a group of the structure

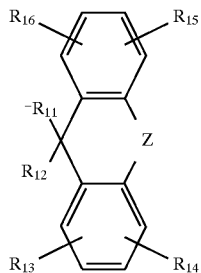

$R^{11}$ is a bond, alkylene, alkenylene or alkynylene of up to 6 carbon atoms, arylene (for example

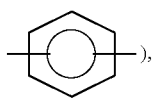

or mixed arylene-alkylene (for example

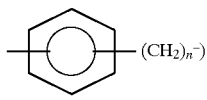

where n is 1 to 6;

$R^{12}$ is hydrogen, alkyl, alkenyl, aryl, heteroaryl, haloalkyl, arylalkyl, arylalkenyl, cycloalkyl, aryloxy, alkoxy, arylalkoxy, heteroarylalkyl or cycloalkylalkyl;

Z is a bond, O, S, N-alkyl, N-aryl, or alkylene or alkenylene of from 1 to 5 carbon atoms;

$R^{13}$, $R^{14}$, $R^{15}$, and $R^{16}$ are independently hydrogen, alkyl, halo, haloalkyl, aryl, cycloalkyl, cycloheteroalkyl, alkenyl, alkynyl, hydroxy, alkoxy, nitro, amino, thio, alkylsulfonyl, arylsulfonyl, alkylthio, arylthio, carboxy, aminocarbonyl, alkylcarbonyloxy, alkylcarbonylamino, arylalkyl, heteroaryl, heteroarylalkyl, or aryloxy;

or $R^1$ is

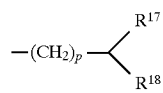

wherein p is 1 to 8 and $R^{17}$ and $R^{18}$ are each independently H, alkyl, alkenyl, aryl, arylalkyl, heteroaryl, heteroarylalkyl, cycloalkyl or cycloalkylalkyl, at least one of $R^{17}$ and $R^{18}$ being other than H;

or $R^1$ is

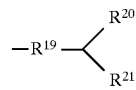

wherein $R^{19}$ is aryl or heteroaryl;

$R^{20}$ is aryl or heteroaryl;

$R^{21}$ is H, alkyl, aryl, alkylaryl, arylalkyl, aryloxy, arylalkoxy, heteroaryl, heteroarylalkyl, heteroarylalkoxy, cycloalkyl, cycloalkylalkyl or cycloalkylalkoxy;

$R^2$, $R^3$, $R^4$ are independently hydrogen, halo, alkyl, haloalkyl, alkenyl, alkoxy, aryloxy, aryl, arylalkyl, alkylmercapto, arylmercapto, cycloalkyl, cycloalkylalkyl, heteroaryl, heteroarylalkyl, hydroxy or haloalkyl;

$R^5$ is alkyl of at least 2 carbons, alkenyl, alkynyl, aryl, heteroaryl, arylalkyl, heteroarylalkyl, cycloalkyl, cycloalkylalkyl, polycycloalkyl, polycycloalkylalkyl, cycloalkenyl, cycloalkenylalkyl, polycycloalkenyl, polycycloalkenylalkyl, heteroarylcarbonyl, all of the $R^5$ and $R^6$ substituents being optionally substituted through available carbon atoms with 1, 2, or 3 groups selected from hydrogen, halo, alkyl, haloalkyl, alkoxy, haloalkoxy, alkenyl, alkynyl, cycloalkyl, cycloalkylalkyl, cycloheteroalkyl, cycloheteroalkylalkyl, aryl, heteroaryl, arylalkyl, arylcyclo-alkyl, arylalkynyl, aryloxy, aryloxyalkyl, aryl-alkoxy, arylazo, heteroaryloxo, heteroarylalkyl, heteroarylalkenyl, heteroaryloxy, hydroxy, nitro, cyano, amino, substituted amino (wherein the amino includes 1 or 2 substituents which are alkyl, or aryl or any of the other aryl compounds mentioned in the definitions), thiol, alkylthio, arylthio, heteroarylthio, arylthioalkyl, alkylcarbonyl, arylcarbonyl, arylaminocarbonyl, alkoxycarbonyl, aminocarbonyl, alkynylaminocarbonyl, alkylaminocarbonyl, alkenylaminocarbonyl, alkylcarbonyloxy, arylcarbonyloxy, alkylcarbonylamino, arylcarbonylamino, arylsulfinyl, arylsulfinylalkyl, arylsulfonyl, alkylsulfonyl, arylsulfonylamino; with the proviso that when $R^5$ is $CH_3$, $R^6$ is not H; and where $R^5$ is phenyl, the phenyl preferably includes an ortho hydrophobic substituent such as alkyl, haloalkyl, aryl, aryloxy or arylalkyl;

$R^6$ is hydrogen or $C_1$–$C_4$ alkyl or $C_1$–$C_4$ alkenyl;

$R^7$ is alkyl, aryl or arylalkyl wherein alkyl or the alkyl portion is optionally substituted with oxo; and including pharmaceutically acceptable salts and anions thereof.

In the formula I compounds, where X is $CH_2$ and $R^2$, $R^3$ and $R^4$ are each H, $R^1$ will be other than 3,3-diphenylpropyl.

In the formula III compounds, where one of $R^2$, $R^3$ and $R^4$ is 6-fluoro, and the others are H, $R^7$ will be other than 4-O-methoxyphenyl.

U.S. application Ser. No. 472,067, filed Jun. 6, 1995 (file DC21e), U.S. Pat. No. 5,739,135 discloses compounds of the structure

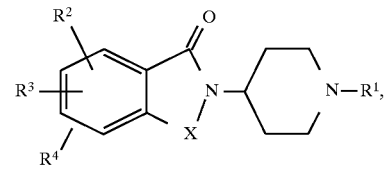

or

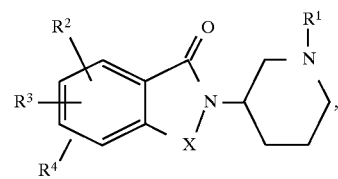

or

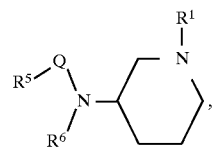

or

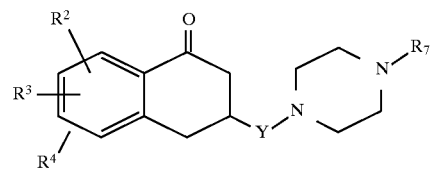

where Q is

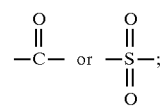

X is:

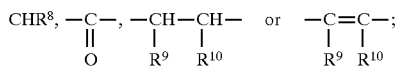

$R^8$, $R^9$ and $R^{10}$ are independently hydrogen, alkyl, alkenyl, alkynyl, aryl, arylalkyl, heteroaryl, heteroarylalkyl, cycloalkyl, or cycloalkylalkyl;

Y is

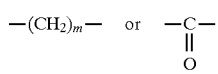

wherein m is 2 or 3;

$R^1$ is alkyl, alkenyl, alkynyl, aryl, heteroaryl, arylalkyl wherein alkyl has at least 2 carbons, diarylalkyl, arylalkenyl, diarylalkenyl, arylalkynyl, diarylalkynyl, diarylalkylaryl, heteroarylalkyl wherein alkyl has at least 2 carbons, cycloalkyl, or cycloalkylalkyl wherein alkyl has at least 2 carbons, all optionally substituted through available carbon atoms with 1, 2, 3 or 4 groups selected from halo, haloalkyl, alkyl, alkenyl, alkoxy, aryloxy, aryl, arylalkyl, alkylmercapto, arylmercapto, cycloalkyl, cyclo-alkylalkyl, heteroaryl, fluorenyl, heteroarylalkyl, hydroxy or oxo;

or $R^1$ is a fluorenyl-type group of the structure

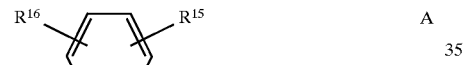 A

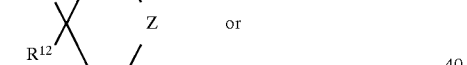 B

 C

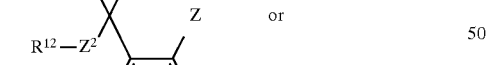 D $R^1$ is an indenyl-type group of the structure

 E (a = 2, 3 or 4)

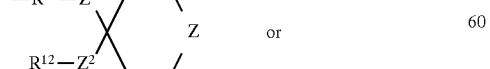 F

 G

 H $Z^1$ and $Z^2$ are the same or different and are independently a bond, O, S,

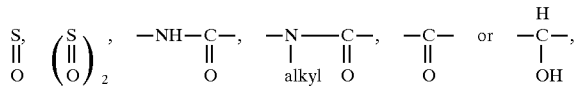

with the proviso that with respect to B, at least one of $Z^1$ and $Z^2$ will be other than a bond; $R^{11}$ is a bond, alkylene, alkenylene or alkynylene of up to 10 carbon atoms; arylene or mixed arylene-alkylene; $R^{12}$ is hydrogen, alkyl, alkenyl, aryl, haloalkyl, trihaloalkyl, trihaloalkylalkyl, heteroaryl, heteroarylalkyl, arylalkyl, arylalkenyl, cyclo-alkyl, aryloxy, alkoxy, arylalkoxy or cycloalkyl-alkyl, with the provisos that (1) when $R^{12}$ is H, aryloxy, alkoxy or

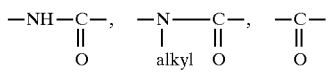

or arylalkoxy, then $Z^2$ is a bond and
(2) when $Z^2$ is a bond, $R^{12}$ cannot be heteroaryl or heteroarylalkyl;

Z is bond, O, S, N-alkyl, N-aryl, or alkylene or alkenylene from 1 to 5 carbon atoms; $R^{13}$, $R^{14}$, $R^{15}$, and $R^{16}$ are independently hydrogen, alkyl, halo, haloalkyl, aryl, cycloalkyl, cyclo-heteroalkyl, alkenyl, alkynyl, hydroxy, alkoxy, nitro, amino, thio, alkylsulfonyl, arylsulfonyl, alkylthio, arylthio, aminocarbonyl, alkylcarbonyloxy, arylcarbonylamino, alkylcarbonylamino, arylalkyl, heteroaryl, heteroarylalkyl or aryloxy;

$R^{15a}$ and $R^{16a}$ are independently hydrogen, alkyl, halo, haloalkyl, aryl, cycloalkyl, cycloheteroalkyl, alkenyl, alkynyl, alkoxy, alkylsulfonyl, arylsulfonyl, alkylthio, arylthio, aminocarbonyl, alkylcarbonyloxy, arylcarbonylamino, alkylcarbonylamino, arylalkyl, heteroaryl, heteroarylalkyl, or aryloxy;

or $R^1$ is a group of the structure

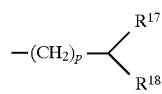

wherein p is 1 to 8 and $R^{17}$ and $R^{18}$ are each independently H, alkyl, alkenyl, aryl, arylalkyl, heteroaryl, heteroarylalkyl, cycloalkyl or cycloalkylalkyl at least one of $R^{17}$ and $R^{18}$ being other than H;

or $R^1$ is a group of the structure

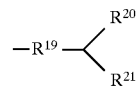

wherein $R^{19}$ is aryl or heteroaryl;
$R^{20}$ is aryl or heteroaryl;
$R^{21}$ is H, alkyl, aryl, alkylaryl, arylalkyl, aryloxy, arylalkoxy, heteroaryl, heteroarylalkyl, heteroarylalkoxy, cycloalkyl, cycloalkylalkyl or cycloalkylalkoxy;
$R^2$, $R^3$, $R^4$ are independently hydrogen, halo, alkyl, alkenyl, alkoxy, aryloxy, aryl, arylalkyl, alkylmercapto, arylmercapto, cycloalkyl, cycloalkylalkyl, heteroaryl, heteroarylalkyl, hydroxy or haloalkyl;
$R^5$ is independently alkyl, alkenyl, alkynyl, aryl, alkoxy, aryloxy, arylalkoxy, heteroaryl, arylalkyl, heteroarylalkyl, cycloalkyl, cycloalkylalkyl, polycycloalkyl, polycycloalkylalkyl, cycloalkenyl, cycloheteroalkyl, heteroaryloxy, cycloalkenylalkyl, polycycloalkenyl, polycycloalkenylalkyl, heteroarylcarbonyl, amino, alkylamino, arylamino, heteroarylamino, cycloalkyloxy, cycloalkylamino, all optionally substituted through available carbon atoms with 1, 2, 3 or 4 groups selected from hydrogen, halo, alkyl, haloalkyl, alkoxy, haloalkoxy, alkenyl, alkynyl, cycloalkyl, cycloalkylalkyl, cycloheteroalkyl, cycloheteroalkylalkyl, aryl, heteroaryl, arylalkyl, arylcycloalkyl, arylalkenyl, arylalkynyl, aryloxy, aryloxyalkyl, arylalkoxy, arylazo, heteroaryloxo, heteroarylalkyl, heteroarylalkenyl, heteroaryloxy, hydroxy, nitro, cyano, amino, substituted amino, thiol, alkylthio, arylthio, heteroarylthio, arylthioalkyl, alkylcarbonyl, arylcarbonyl, arylaminocarbonyl, alkoxycarbonyl, aminocarbonyl, alkynylaminocarbonyl, alkylaminocarbonyl, alkenylaminocarbonyl, alkylcarbonyloxy, arylcarbonyloxy, alkylcarbonylamino, arylcarbonylamino, arylsulfinyl, arylsulfinylalkyl, arylsulfonyl, alkylsulfonyl, arylsulfonylamino, heteroarylcarbonylamino, heteroarylsulfinyl, heteroarylthio, heteroarylsulfonyl, alkylsulfinyl;
$R^6$ is hydrogen or $C_1$–$C_4$ alkyl or $C_1$–$C_4$ alkenyl; all optionally substituted with 1, 2, 3 or 4 groups which may independently be any of the substituents listed in the definition of $R^5$ set out above;
$R^7$ is alkyl, aryl or arylalkyl wherein alkyl by itself or as part of arylalkyl is optionally substituted with oxo

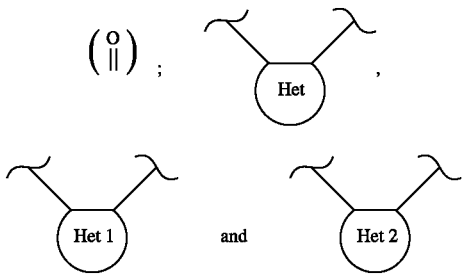

are the same or different and are independently selected from heteroaryl containing 5- or 6-ring members; and N-oxides

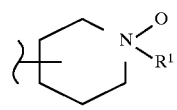

thereof; and
pharmaceutically acceptable salts thereof; with the provisos that where in the first formula X is $CH_2$, and $R^2$, $R^3$ and $R^4$ are each H, then $R^1$ will be other than 3,3-diphenylpropyl, and in the fifth formula, where one of $R^2$, $R^3$ and $R^4$ is 6-fluoro, and the others are H, $R^7$ will be other than 4-(2-methoxyphenyl).

U.S. application Ser. No. 548,811 filed Jan. 11, 1996 (file DC21h), discloses compounds having the structure

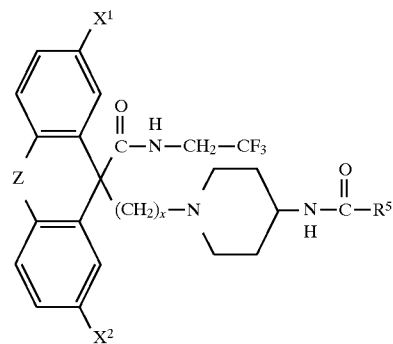

including the piperidine N-oxide thereof or a pharmaceutically acceptable salt thereof, wherein Z is a bond, O or S;

$X^1$ and $X^2$ are independently selected from H or halo;

x is an integer from 2 to 6;

$R^5$ is heteroaryl, aryl, heterocycloalkyl or cycloalkyl, each $R^5$ group being optionally substituted with 1, 2, 3 or 4 substituents which may be the same or different.

SUMMARY OF THE INVENTION

In accordance with the present invention, novel compounds are provided which are inhibitors of MTP and have the structure

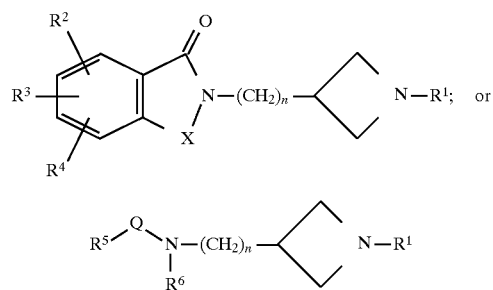

where Q is

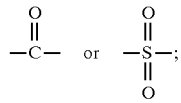

X is: $CHR^8$,

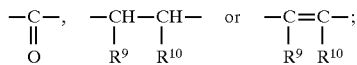

n is 0 or 1; $R^8$, $R^9$ and $R^{10}$ are independently hydrogen, alkyl, alkenyl, alkynyl, aryl, arylalkyl, heteroaryl, heteroarylalkyl, cycloalkyl, or cycloalkylalkyl;

$R^1$ is alkyl, alkenyl, alkynyl, aryl, heteroaryl, arylalkyl (wherein alkyl preferably has at least 2 carbons, more preferably at least 3 carbons), diarylalkyl, arylalkenyl, diarylalkenyl, arylalkynyl, diarylalkynyl, diarylalkylaryl, heteroarylalkyl (wherein alkyl preferably has at least 2 carbons, more preferably at least 3 carbons), cycloalkyl, or cycloalkylalkyl (wherein alkyl preferably has at least 2 carbons, more preferably at least 3 carbons); all of the aforementioned $R^1$ groups being optionally substituted through available carbon atoms with 1, 2, 3 or 4 groups selected from halo, haloalkyl, alkyl, alkenyl, alkoxy, aryloxy, aryl, arylalkyl, alkyl-mercapto, arylmercapto, cycloalkyl, cycloalkyl-alkyl, heteroaryl, fluorenyl, heteroarylalkyl, hydroxy or oxo; or $R^1$ is a fluorenyl-type group of the structure

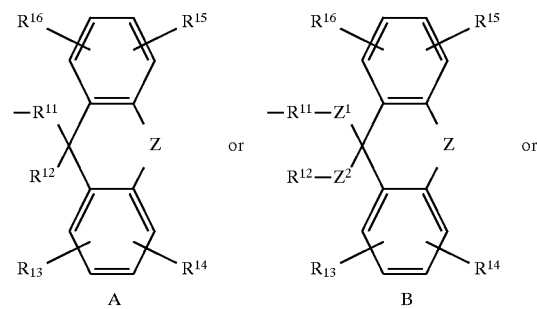

$R^1$ is an indenyl-type group of the structure

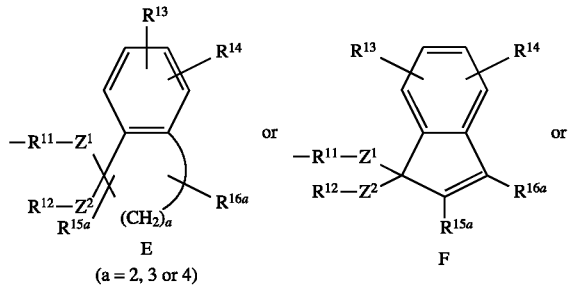

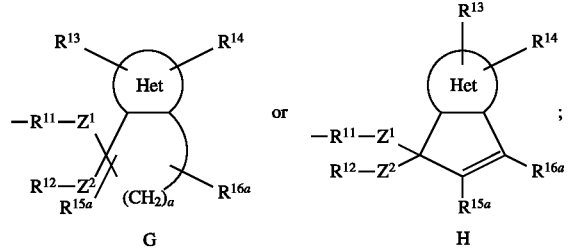

$Z^1$ and $Z^2$ are the same or different and are independently a bond, O, S,

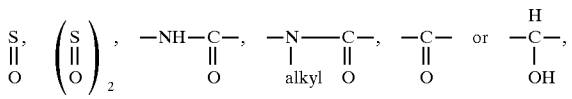

with the proviso that with respect to B, at least one of $Z^1$ and $Z^2$ will be other than a bond;

$R^{11}$ is a bond, alkylene, alkenylene or alkynylene of up to 10 carbon atoms, arylene (for example

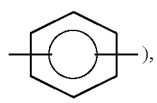

or mixed arylene-alkylene (for example

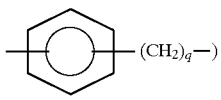

where q is 1 to 6;

$R^{12}$ is hydrogen, alkyl, alkenyl, aryl, haloalkyl, trihaloalkyl, trihaloalkylalkyl, heteroaryl, heteroarylalkyl, arylalkyl, arylalkenyl, cyclo-alkyl, aryloxy, alkoxy, arylalkoxy or cycloalkyl-alkyl; with the provisos that (1) when $R^{12}$ is H, aryloxy, alkoxy or arylalkoxy, then $Z^2$ is

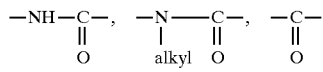

or a bond;

and (2) when $Z^2$ is a bond, $R^{12}$ cannot be heteroaryl or heteroarylalkyl;

Z is a bond, O, S, N-alkyl, N-aryl, or alkylene or alkenylene of from 1 to 5 carbon atoms;

$R^{13}$, $R^{14}$, $R^{15}$, and $R^{16}$ are independently hydrogen, alkyl, halo, haloalkyl, aryl, cycloalkyl, cycloheteroalkyl, alkenyl, alkynyl, hydroxy, alkoxy, nitro, amino, thio, alkylsulfonyl, arylsulfonyl, alkylthio, arylthio, aminocarbonyl, alkylcarbonyloxy, arylcarbonylamino, alkylcarbonylamino, arylalkyl, heteroaryl, heteroarylalkyl, or aryloxy;

$R^{15a}$ and $R^{16a}$ are independently any of the $R^{15}$ or $R^{16}$ groups except hydroxy, nitro, amino or thio;

or $R^1$ is

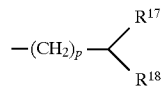

wherein p is 1 to 8 and $R^{17}$ and $R^{18}$ are each independently H, alkyl, alkenyl, aryl, arylalkyl, heteroaryl, heteroarylalkyl, cycloalkyl or cycloalkylalkyl, at least one of $R^{17}$ and $R^{18}$ being other than H;

or $R^1$ is

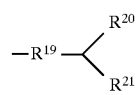

wherein $R^{19}$ is aryl or heteroaryl;

$R^{20}$ is aryl or heteroaryl;

$R^{21}$ is H, alkyl, aryl, alkylaryl, arylalkyl, aryloxy, arylalkoxy, heteroaryl, heteroarylalkyl, heteroarylalkoxy, cycloalkyl, cycloalkylalkyl or cycloalkylalkoxy;

$R^2$, $R^3$, $R^4$ are independently hydrogen, halo, alkyl, alkenyl, alkoxy, aryloxy, aryl, arylalkyl, alkylmercapto, arylmercapto, cycloalkyl, cycloalkylalkyl, heteroaryl, heteroarylalkyl, hydroxy or haloalkyl;

$R^5$ is alkyl, alkenyl, alkynyl, aryl, alkoxy, aryloxy, arylalkoxy, heteroaryl, arylalkyl, heteroarylalkyl, cycloalkyl, cycloheteroalkyl, heteroaryloxy, cycloalkylalkyl, polycycloalkyl, polycycloalkylalkyl, cycloalkenyl, cycloalkenylalkyl, polycycloalkenyl, polycycloalkenylalkyl, heteroarylcarbonyl, amino, alkylamino, arylamino, heteroarylamino, cycloalkyloxy, cycloalkylamino, all of the $R^5$ substituents and $R^6$ substituents (set out hereinafter) being optionally substituted through available carbon atoms with 1, 2, 3 or 4 groups selected from hydrogen, halo, alkyl, haloalkyl, alkoxy, haloalkoxy, alkenyl, alkynyl, cycloalkyl, cycloalkylalkyl, cycloheteroalkyl, cycloheteroalkylalkyl, aryl, heteroaryl, arylalkyl, arylcycloalkyl, arylalkenyl, arylalkynyl, aryloxy, aryloxyalkyl, arylalkoxy, arylazo, heteroaryloxo, heteroarylalkyl, heteroarylalkenyl, heteroaryloxy, hydroxy, nitro, cyano, amino, substituted amino (wherein the amino includes 1 or 2 substituents which are alkyl, aryl or heteroaryl, or any of the other aryl compounds mentioned in the definitions), thiol, alkylthio, arylthio, heteroarylthio, arylthioalkyl, alkylcarbonyl, arylcarbonyl, arylaminocarbonyl, alkoxycarbonyl, aminocarbonyl, alkynylaminocarbonyl, alkylaminocarbonyl, alkenylaminocarbonyl, alkylcarbonyloxy, arylcarbonyloxy, alkylcarbonylamino, arylcarbonylamino, arylsulfinyl, arylsulfinylalkyl, arylsulfonyl, alkylsulfonyl, arylsulfonylamino, heteroarylcarbonylamino, heteroarylsulfinyl, heteroarylthio, heteroarylsulfonyl, or alkylsulfinyl. Where $R^5$ is phenyl, aryl, heteroaryl or cycloalkyl; this group preferably includes an ortho hydrophobic substituent such as alkyl, haloalkyl (with up to 5 halo groups), alkoxy, haloalkoxy (with up to 5 halo groups), aryl, aryloxy or arylalkyl;

$R^6$ is hydrogen or $C_1$–$C_4$ alkyl or $C_1$–$C_4$ alkenyl;

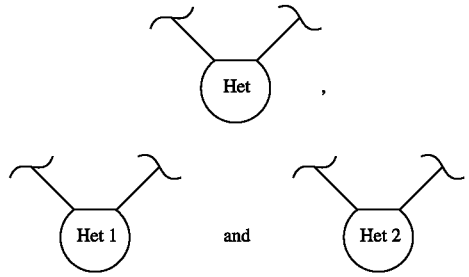

are the same or different and are independently selected from heteroaryl containing 5- or 6-ring members; and including N-oxides of the formulae I and II compounds, that is

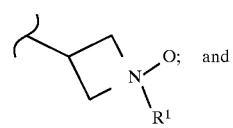

including pharmaceutically acceptable salts thereof such as alkali metal salts such as lithium sodium or potassium, alkaline earth metal salts such as calcium or magnesium, as well as zinc or aluminum and other cations such as ammonium, choline, diethanolamine, ethylenediamine, t-butylamine, t-octylamine, dehydroabietylamine, as well as pharmaceutically acceptable anions such as chloride, bromide, iodide, tartrate, acetate, methanesulfonate, maleate, succinate, glutarate, and salts of naturally occurring amino acids such as arginine, lysine, alanine and the like, and prodrug esters thereof.

In the formula I compounds, where X is $CH_2$ and $R^2$, $R^3$ and $R^4$ are each H, $R^1$ will preferably be other than 3,3-diphenylpropyl.

Thus, the compounds of formulae I and II of the invention encompass compounds of the structure

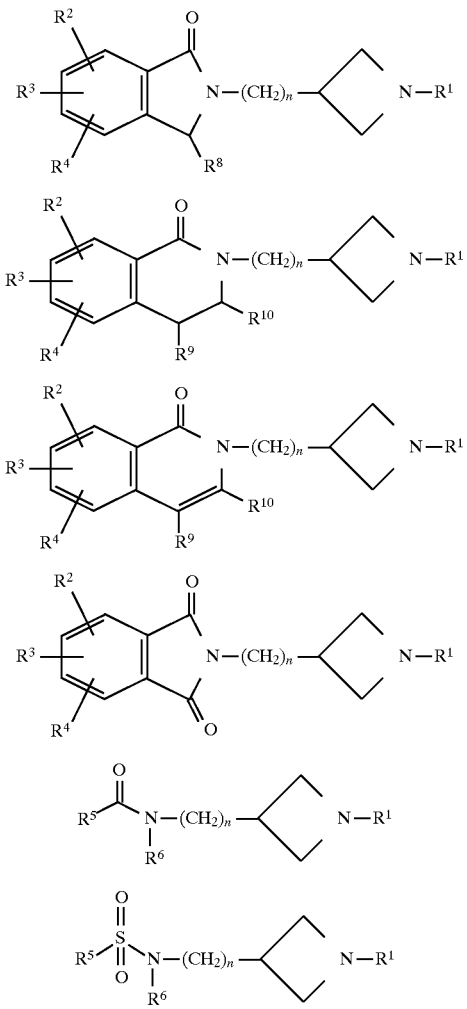

In addition, in accordance with the present invention, a method for preventing, inhibiting or treating atherosclerosis, pancreatitis or obesity is provided, wherein a compound of formula I or II as defined hereinbefore is administered in an amount which decreases the activity of microsomal triglyceride transfer protein.

Furthermore, in accordance with the present invention, a method is provided for lowering serum lipid levels, cholesterol and/or triglycerides, or inhibiting and/or treating hyperlipemia, hyperlipidemia, hyperlipoproteinemia, hypercholesterolemia and/or hypertriglyceridemia, wherein a compound of formula I or II is administered in an amount which decreases the activity of microsomal triglyceride transfer protein.

DETAILED DESCRIPTION OF THE INVENTION

The following definitions apply to the terms as used throughout this specification, unless otherwise limited in specific instances.

The term "MTP" refers to a polypeptide or protein complex that (1) if obtained from an organism (e. g., cows, humans, etc.), can be isolated from the microsomal fraction of homogenized tissue; and (2) stimulates the transport of triglycerides, cholesterol esters, or phospholipids from synthetic phospholipid vesicles, membranes or lipoproteins to synthetic vesicles, membranes, or lipoproteins and which is distinct from the cholesterol ester transfer protein [Drayna et al., *Nature* 327, 632–634 (1987)] which may have similar catalytic properties. However, the MTP molecules of the present invention do not necessarily need to be catalytically active. For example, catalytically inactive MTP or fragments thereof may be useful in raising antibodies to the protein.

The phrase "stabilizing" atherosclerosis as used in the present application refers to slowing down the development of and/or inhibiting the formation of new atherosclerotic lesions.

The phrase "causing the regression of" atherosclerosis as used in the present application refers to reducing and/or eliminating atherosclerotic lesions.

Unless otherwise indicated, the term "lower alkyl", "alkyl" or "alk" as employed herein alone or as part of another group includes both straight and branched chain hydrocarbons, containing 1 to 40 carbons, preferably 1 to 20 carbons, more preferably 1 to 12 carbons, in the normal chain, such as methyl, ethyl, propyl, isopropyl, butyl, t-butyl, isobutyl, pentyl, hexyl, isohexyl, heptyl, 4,4-dimethylpentyl, octyl, 2,2,4-trimethyl-pentyl, nonyl, decyl, undecyl, dodecyl, the various branched chain isomers thereof, and the like as well as such groups including 1 to 4 substituents such as halo, for example F, Br, Cl or I or $CF_3$, alkoxy, aryl, aryloxy, aryl(aryl) or diaryl, arylalkyl, arylalkyloxy, alkenyl, cycloalkyl, cycloalkylalkyl, cycloalkylalkyloxy, amino, hydroxy, acyl, heteroaryl, heteroaryloxy, heteroarylalkyl, heteroarylalkoxy, aryloxyalkyl, aryloxyaryl, alkylamido, alkanoylamino, arylcarbonylamino, nitro, cyano, thiol, haloalkyl, trihaloalkyl and/or alkylthio, as well as any of the other substituents as defined for $R^5$ and $R^6$.

Unless otherwise indicated, the term "cycloalkyl" as employed herein alone or as part of another group includes saturated or partially unsaturated (containing 1 or 2 double bonds) cyclic hydrocarbon groups containing 1 to 3 rings, including monocyclicalkyl, bicyclicalkyl and tricyclicalkyl, containing a total of 3 to 20 carbons forming the rings, preferably 4 to 12 carbons, forming the ring and which may be fused to 1 or 2 aromatic rings as described for aryl, which include cyclopropyl, cyclobutyl, cyclopentyl, cyclohexyl, cycloheptyl, cyclooctyl, cyclodecyl and cyclododecyl, cyclohexenyl,

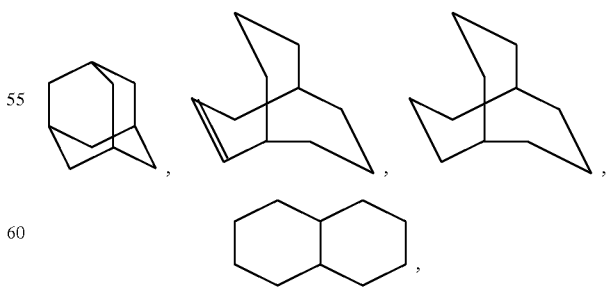

any of which groups may be optionally substituted with 1 to 4 substituents such as halogen, alkyl, alkoxy, hydroxy, aryl, aryloxy, arylalkyl, cycloalkyl, alkylamido, alkanoylamino, oxo, acyl, arylcarbonylamino, amino, nitro, cyano, thiol and/or alkylthio, as well as any of the other substituents as defined for $R^5$ or $R^6$.

The term "cycloalkenyl" as employed herein alone or as part of another group refers to cyclic hydrocarbons containing 5 to 20 carbons, preferably 6 to 12 carbons and 1 or 2 double bonds. Exemplary cycloalkenyl groups include cyclopentenyl, cyclohexenyl, cycloheptenyl, cyclooctenyl, cyclohexadienyl, and cycloheptadienyl, which may be optionally substituted as defined for cycloalkyl.

The term "polycycloalkyl" as employed herein alone or as part of another group refers to a bridged multicyclic group containing 5 to 20 carbons and containing 0 to 3 bridges, preferably 6 to 12 carbons and 1 or 2 bridges. Exemplary polycycloalkyl groups include [3.3.0]-bicyclo-octanyl, adamantanyl, [2.2.1]-bicycloheptanyl, [2.2.2]-bicyclooctanyl and the like and may be optionally substituted as defined for cycloalkyl.

The term "polycycloalkenyl" as employed herein alone or as part of another group refers to a bridged multicyclic group containing 5 to 20 carbons and containing 0 to 3 bridges and containing 1 or 2 double bonds, preferably 6 to 12 carbons and 1 or 2 bridges. Exemplary polycyclo-alkyl groups include [3.3.0]-bicyclooctenyl, [2.2.1]-bicycloheptenyl, [2.2.2]-bicyclooctenyl and the like and may be optionally substituted as defined for cycloalkyl.

The term "aryl" or "Ar" as employed herein alone or as part of another group refers to monocyclic and bicyclic aromatic groups containing 6 to 10 carbons in the ring portion (such as phenyl or naphthyl) and may optionally include one to three additional rings fused to Ar (such as aryl, cycloalkyl, heteroaryl or cycloheteroalkyl rings) and may be optionally substituted through available carbon atoms with 1, 2, 3 or 4 groups selected from hydrogen, halo, haloalkyl, alkyl, haloalkyl, alkoxy, haloalkoxy, alkenyl, trifluoromethyl, trifluoromethoxy, alkynyl, cycloalkylalkyl, cycloheteroalkyl, cycloheteroalkylalkyl, aryl, heteroaryl, arylalkyl, aryloxy, aryloxyalkyl, arylalkoxy, arylthio, arylazo, heteroarylalkyl, heteroarylalkenyl, heteroarylheteroaryl, heteroaryloxy, hydroxy, nitro, cyano, amino, substituted amino wherein the amino includes 1 or 2 substituents (which are alkyl, aryl or any of the other aryl compounds mentioned in the definitions), thiol, alkylthio, arylthio, heteroarylthio, arylthioalkyl, alkoxyarylthio, alkylcarbonyl, arylcarbonyl, alkylaminocarbonyl, arylaminocarbonyl, alkoxycarbonyl, aminocarbonyl, alkylcarbonyloxy, arylcarbonyloxy, alkylcarbonylamino, arylcarbonylamino, arylsulfinyl, arylsulfinylalkyl, arylsulfonylamino or arylsulfonaminocarbonyl, or any of the substituents as defined for the $R^5$ or $R^6$ groups set out above.

The term "aralkyl", "aryl-alkyl" or "aryllower alkyl" as used herein alone or as part of another group refers to alkyl groups as discussed above having an aryl substituent, such as benzyl or phenethyl, or naphthylpropyl, or an aryl as defined above.

The term "lower alkoxy", "alkoxy", "aryloxy" or "aralkoxy" as employed herein alone or as part of another group includes any of the above alkyl, aralkyl or aryl groups linked to an oxygen atom.

The term "amino" as employed herein alone or as part of another group may optionally be substituted with one or two substituents such as alkyl and/or aryl.

The term "lower alkylthio", "alkylthio", "arylthio" or "aralkylthio" as employed herein alone or as part of another group includes any of the above alkyl, aralkyl or aryl groups linked to a sulfur atom.

The term "lower alkylamino", "alkylamino", "arylamino", or "arylalkylamino" as employed herein alone or as part of another group includes any of the above alkyl, aryl or arylalkyl groups linked to a nitrogen atom.

The term "acyl" as employed herein by itself or part of another group as defined herein, refers to an organic radical linked to a carbonyl

group, examples of acyl groups include alkanoyl, alkenoyl, aroyl, aralkanoyl, heteroaroyl, cycloalkanoyl and the like.

The term "alkanoyl" as used herein alone or as part of another group refers to alkyl linked to a carbonyl group.

Unless otherwise indicated, the term "lower alkenyl" or "alkenyl" as used herein by itself or as part of another group refers to straight or branched chain radicals of 2 to 20 carbons, preferably 3 to 12 carbons, and more preferably 1 to 8 carbons in the normal chain, which include one to six double bonds in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12-tetradecatrienyl, and the like, and which may be optionally substituted with 1 to 4 substituents, namely, halogen, haloalkyl, alkyl, alkoxy, alkenyl, alkynyl, aryl, arylalkyl, cyclo-alkyl, amino, hydroxy, heteroaryl, cycloheteroalkyl, alkanoylamino, alkylamido, arylcarbonylamino, nitro, cyano, thiol and/or alkylthio, as well as any of the other substituents as defined for $R^5$ or $R^6$.

Unless otherwise indicated, the term "lower alkynyl" or "alkynyl" as used herein by itself or as part of another group refers to straight or branched chain radicals of 2 to 20 carbons, preferably 2 to 12 carbons and more preferably 2 to 8 carbons in the normal chain, which include one triple bond in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl,3-undecynyl, 4-dodecynyl and the like, and which may be optionally substituted with 1 to 4 substituents, namely, halogen, haloalkyl, alkyl, alkoxy, alkenyl, alkynyl, aryl, arylalkyl, cycloalkyl, amino, heteroaryl, cycloheteroalkyl, hydroxy, alkanoylamino, alkylamido, arylcarbonyl-amino, nitro, cyano, thiol, and/or alkylthio, as well as any of the other substituents as defined for $R^5$ or $R^6$.

The term "alkylene" as employed herein alone or as part of another group (which also encompasses "alkyl" as part of another group such as arylalkyl or heteroarylalkyl) refers to alkyl groups as defined above having single bonds for attachment to other groups at two different carbon atoms and may optionally be substituted as defined above for "alkyl". The definition of alkylene applies to an alkyl group which links one function to another, such as an arylalkyl substituent.

Ther terms "alkenylene" and "alkynylene" as employed herein alone or as part of another group (which also encompass "alkenyl" or "alkynyl", as part of another group such as arylalkenyl or arylalkynyl), refer to alkenyl groups as defined above and alkynyl groups as defined above, respectively, having single bonds for attachment at two different carbon atoms.

Suitable alkylene, alkenylene or alkynylene groups or $(CH_2)_q$ or $(CH_2)_p$ (which may include alkylene, alkenylene or alkynylene groups) as defined herein, may optionally include 1,2, or 3 alkyl, alkoxy, aryl, heteroaryl, cycloheteroalkyl, alkenyl, alkynyl, oxo, aryloxy, hydroxy, halogen substituents as well as any of the substituents defined for $R^5$ or $R^6$, and in addition, may have one of the carbon atoms in the chain replaced with an oxygen atom, N—H, N-alkyl or N-aryl. Examples of alkylene, alkenylene, alkynylene, $(CH_2)_q$ and $(CH_2)_p$ groups include

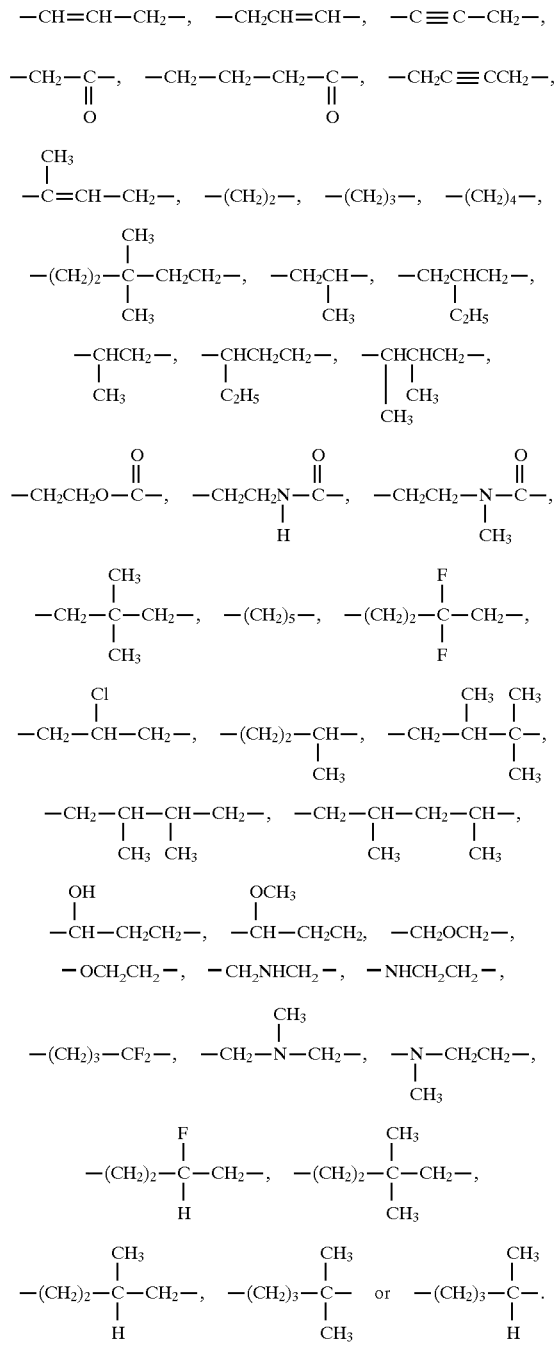

The term "halogen" or "halo" as used herein alone or as part of another group refers to chlorine, bromine, fluorine, and iodine as well as $CF_3$, with chlorine or fluorine being preferred.

The term "metal ion" refers to alkali metal ions such as sodium, potassium or lithium and alkaline earth metal ions such as magnesium and calcium, as well as zinc and aluminum.

The term "cycloheteroalkyl" as used herein alone or as part of another group refers to a 5-, 6- or 7-membered saturated or partially unsaturated ring which includes 1 to 2 hetero atoms such as nitrogen, oxygen and/or sulfur, linked through a carbon atom or a heteroatom, where possible, optionally via the linker $(CH_2)_p$ (which is defined above), such as

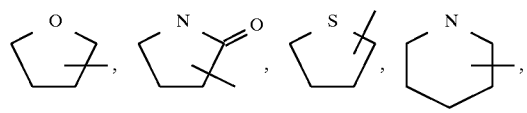

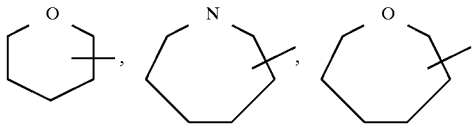

and the like. The above groups may include 1 to 3 substituents such as any of the $R^1$, $R^5$ or $R^6$ groups as defined above. In addition, any of the above rings can be fused to 1 or 2 cycloalkyl, aryl, heteroaryl or cycloheteroalkyl rings.

The term "heteroaryl" or

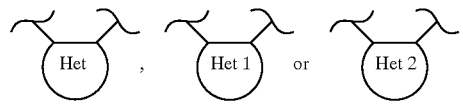

(also referred to as heteroaryl) as used herein alone or as part of another group refers to a 5- or 6-membered aromatic ring which includes 1, 2, 3 or 4 hetero atoms such as nitrogen, oxygen or sulfur, and such rings fused to an aryl, cycloalkyl, heteroaryl or cycloheteroalkyl ring (e.g. benzo-thiophenyl, indolyl), linked through a carbon atom or a heteroatom, where possible, optionally via the linker $(CH_2)_p$ (which is defined above), such as

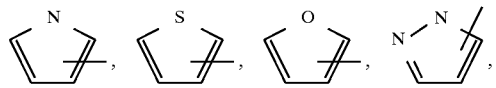

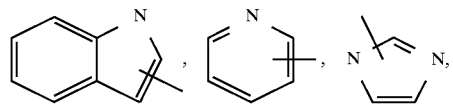

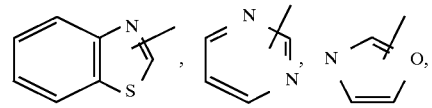

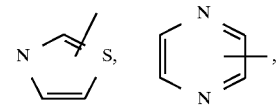

and the like, and includes all possible N-oxide derivatives.

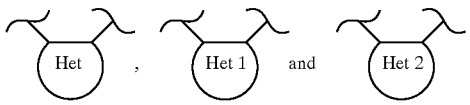

are the same or different as defined hereinbefore and are attached to the central ring of the indenyl or fluorenyl type group at adjacent positions (that is ortho or 1,2-positions). Examples of such groups include

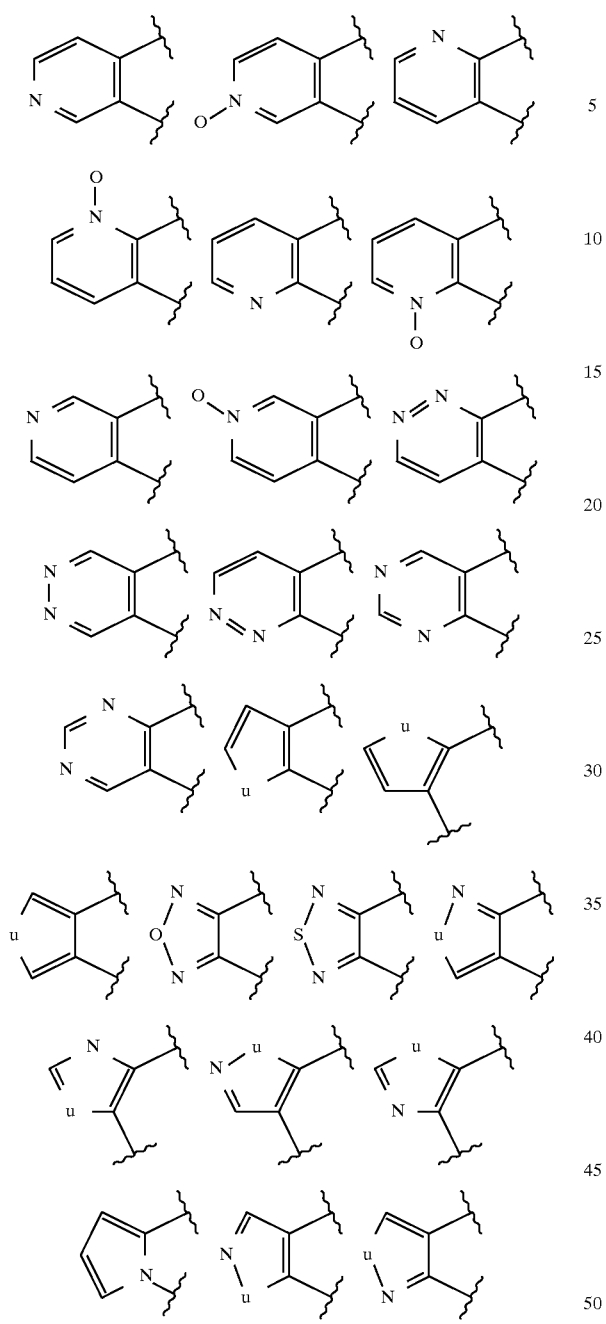

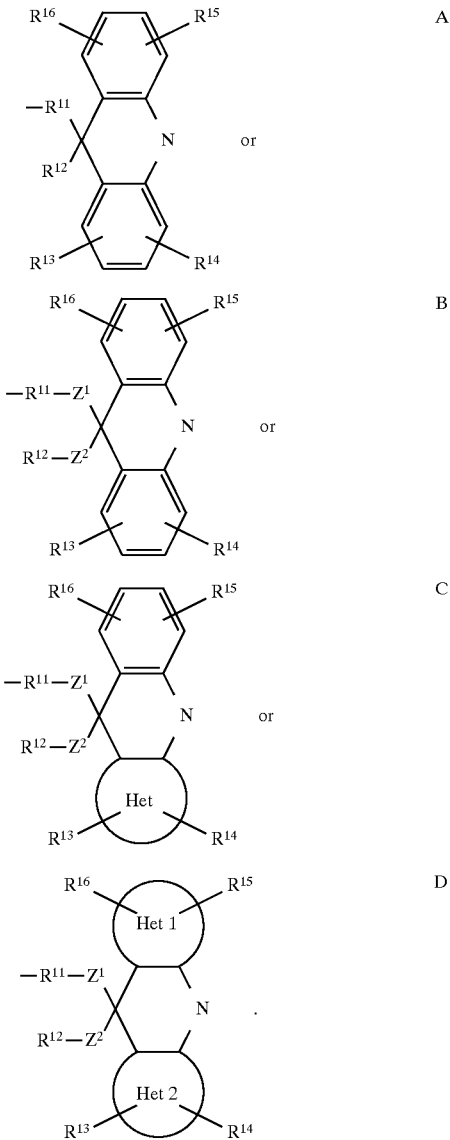

wherein u is selected from O, S, and $NR^{7a}$; $R^{7a}$ is H, lower alkyl, aryl, $—C(O)R^{7b}$, $—C(O)OR^{7b}$; $R^{7b}$ is alkyl or aryl, and includes all possible N-oxide derivatives.

The heteroaryl groups including the above groups may optionally include 1 to 4 substituents such as any of the substituents listed for aryl, or those substituents indicated for $R^5$ or $R^6$ groups as defined above. In addition, any of the above rings can be fused to a cycloalkyl, aryl, heteroaryl or cycloheteroalkyl ring.

The term "cycloheteroalkylalkyl" as used herein alone or as part of another group refers to cycloheteroalkyl groups as defined above linked through a C atom or heteroatom to a $(CH_2)_p$ chain.

The term "heteroarylalkyl" or "heteroarylalkenyl" as used herein alone or as part of another group refers to a heteroaryl group as defined above linked through a C atom or heteroatom to a $—(CH_2)_p$-chain, alkylene or alkenylene as defined above.

The term "fluorenyl" or "fluorenyl analog" or "fluorenyl-type group" as employed herein refers to a group of the structure:

The term "indenyl-type group" as emplyed herein refers to a group of the structure

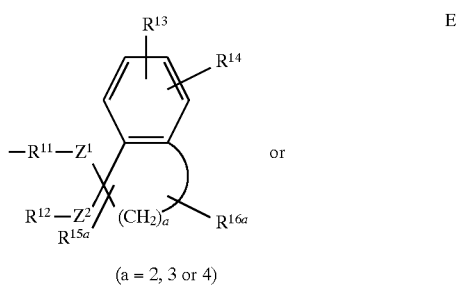

(a = 2, 3 or 4)

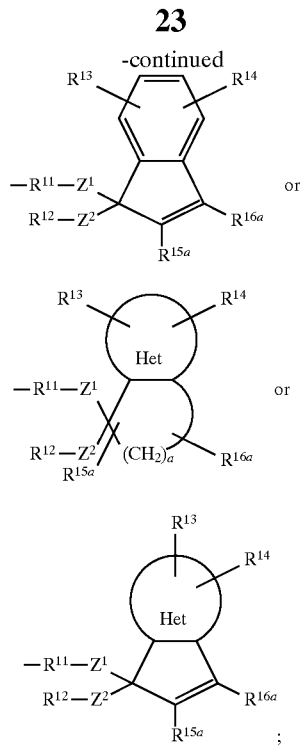

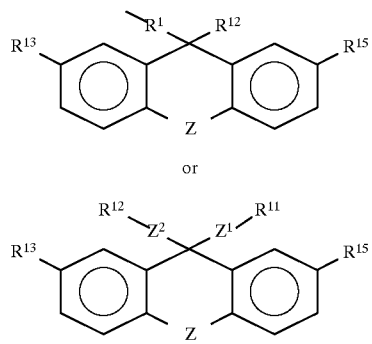

$Z$, $Z^1$, $Z^2$, $R^{11}$, $R^{12}$, $R^{13}$, $R^{14}$, $R^{15}$, $R^{16}$, $R^{15a}$ and as used in the above groups A through H are as defined hereinbefore.

Preferred are compounds of formulae I and II wherein $R^1$ is arylalkyl, arylalkenyl, heteroarylalkyl, heteroarylalkenyl, (including where $Z^1$ is a bond and $R^{11}$ is alkylene or alkenylene and $Z^2$ is

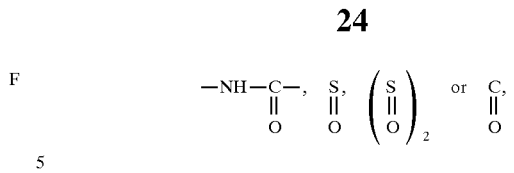

and $R^{12}$ is $C_1$–$C_3$ alkyl or 1,1,1-trifluoroethyl, $R^{13}$ is H or F and $R^{15}$ is H or F, and Z is a bond or O; and where $R^{11}$ is alkylene or alkenylene or alkylene substituted with oxo, $R^{12}$ is alkyl, alkenyl, aralkyl, aralkenyl, Z is O, S or a bond); or

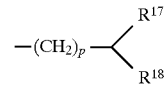

(wherein $R^{17}$ and $R^{18}$ are each independently alkyl, alkenyl, aryl, arylalkyl, heteroaryl, heteroarylalkyl, cycloalkyl or cycloalkylalkyl); or

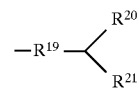

wherein $R^{19}$ is aryl or heteroaryl;
$R^{20}$ is aryl or heteroaryl;
$R^{21}$ is alkyl, aryl, alkylaryl, arylalkyl aryloxy, arylalkoxy, heteroaryl, heteroarylalkyl, heteroarylalkoxy, cycloalkyl, cycloalkylalkyl or cycloalkylalkoxy.

In structure I, it is preferred that $R^2$, $R^3$ and $R^4$ are each H and X is $CH_2$, $CH_2CH_2$, or CH=CH and n is 0.

In structure II, it is preferred that $R^6$ is H or $CH_3$ and $R^5$ is cycloalkyl, phenyl, aryl or heteroaryl, or cycloalkyl, phenyl, aryl heteroaryl having an ortho hydrophobic substituent which is alkyl, alkoxy, haloalkyl (containing up to five halo groups), trifluoromethyl, aryl, aryloxy, arylalkyl, arylalkoxy, haloalkoxy (containing up to five halo groups) and n is 0.

In structure II, it is also preferred that $R^1$ is arylalkyl or heteroarylalkyl wherein alkyl of each has at least 2 carbons (preferably at least 3 carbons) and $R^5$ and $R^6$ may be as defined hereinbefore and may or may not be the preferred groups set out above.

It is to be understood that combinations of substituents which lead to chemically unstable molecules are not included within the scope of the present invention; for example, compounds of the invention will not include —O—O—, —O—C—OH, N—C—OH and —S—C—OH linkages.

The compounds of formulae I and II may be prepared by the exemplary processes described in the following reaction schemes. Exemplary reagents and procedures for these reactions appear hereinafter and in the working Examples.

Scheme I.
Routes to Isoindolinone Azetidines
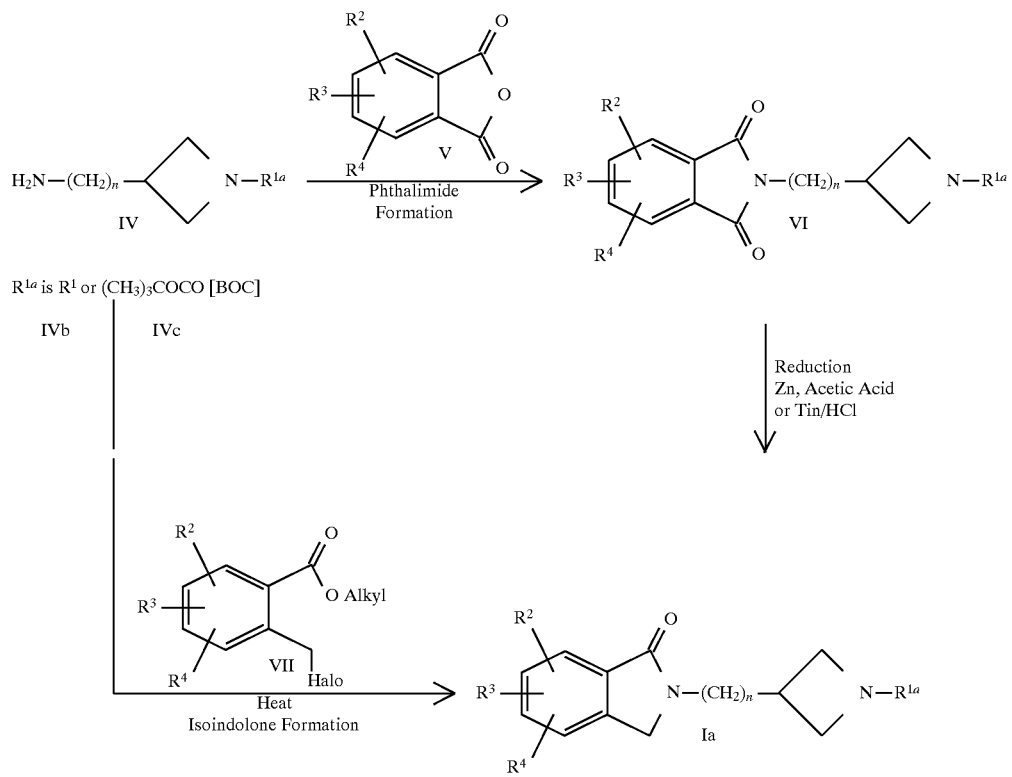
Scheme II.
Additional Routes to Isoindolinone Azetidines
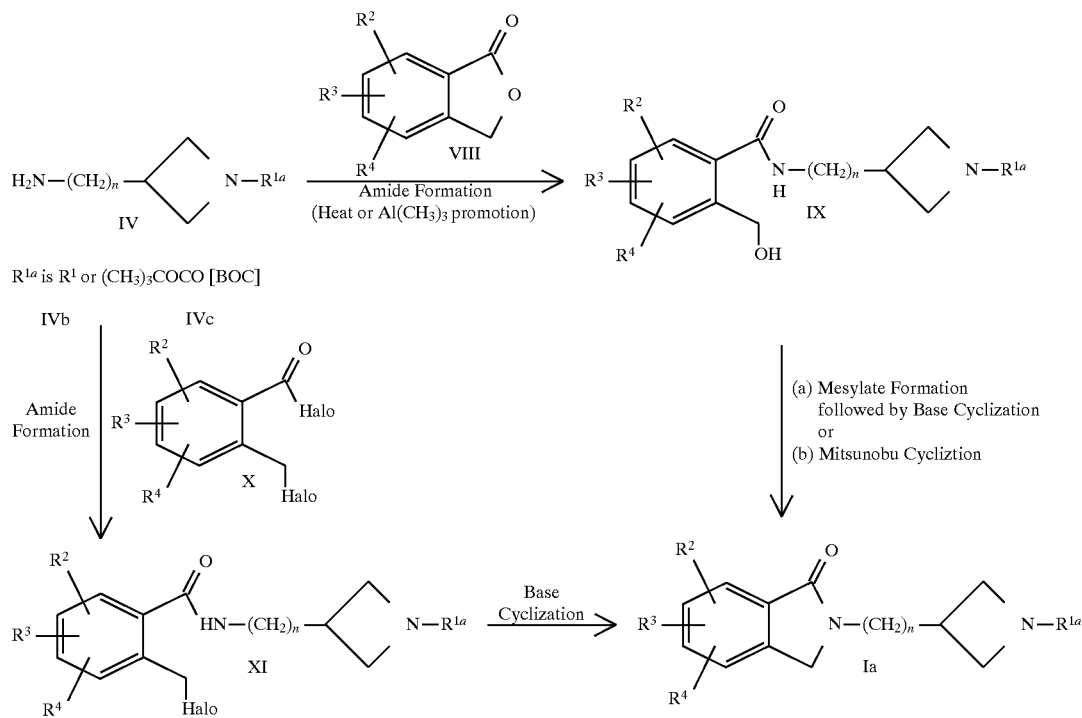

Scheme III.
Introduction of R¹ by Alkylation or Arylation
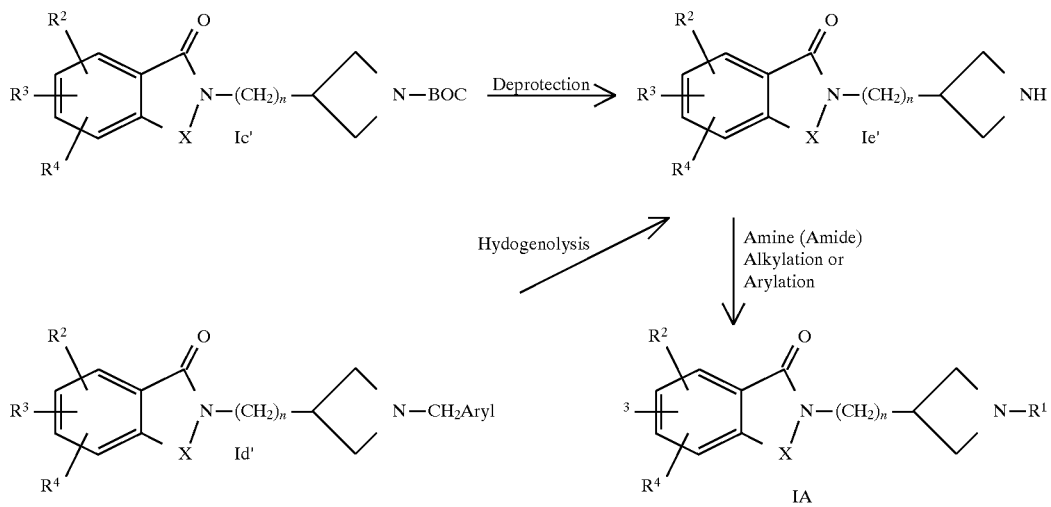
Scheme IV.
Routes to Starting Materials IVb, IVc, IVd and IVe
Scheme (1). Route to 3-amino-azetidine starting material (IVd)
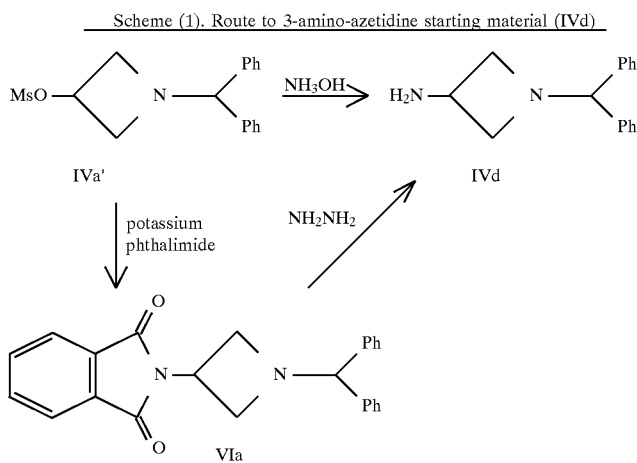
Scheme (2). Routes to IVb and IVc
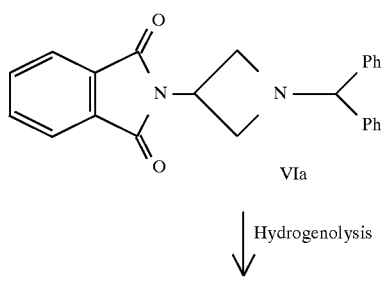

-continued
Scheme (2). Routes to IVb and IVc
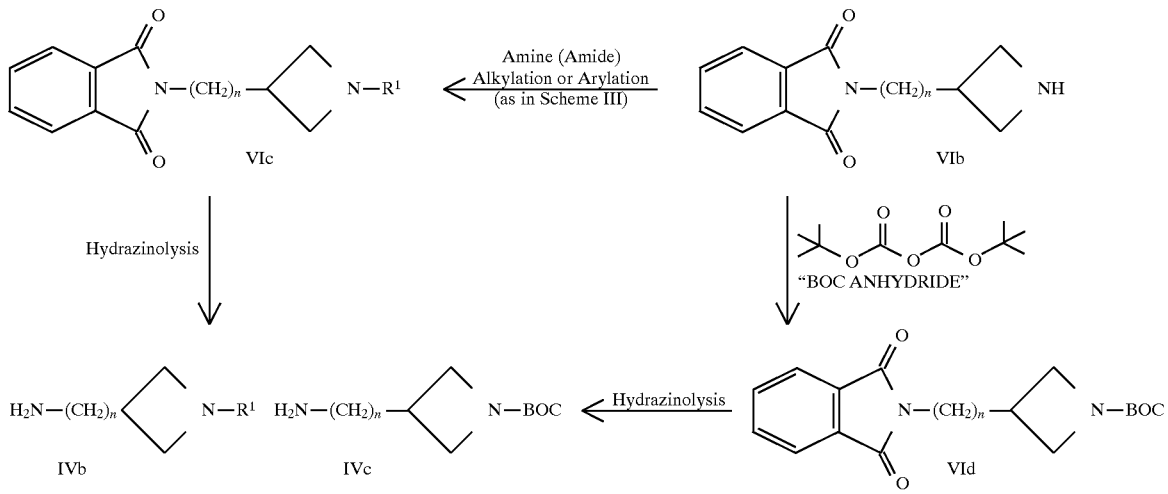
Scheme (3). Route to 3-(aminomethyl)-azetidine starting material (IVe)
-continued
Scheme (3). Route to 3-(aminomethyl)-azetidine starting material (IVe)
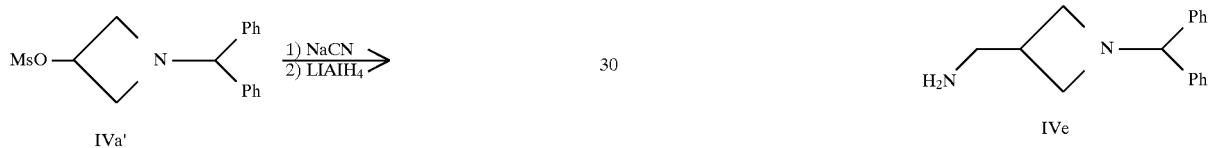
Scheme V.
General Routes to Starting Materials IVb
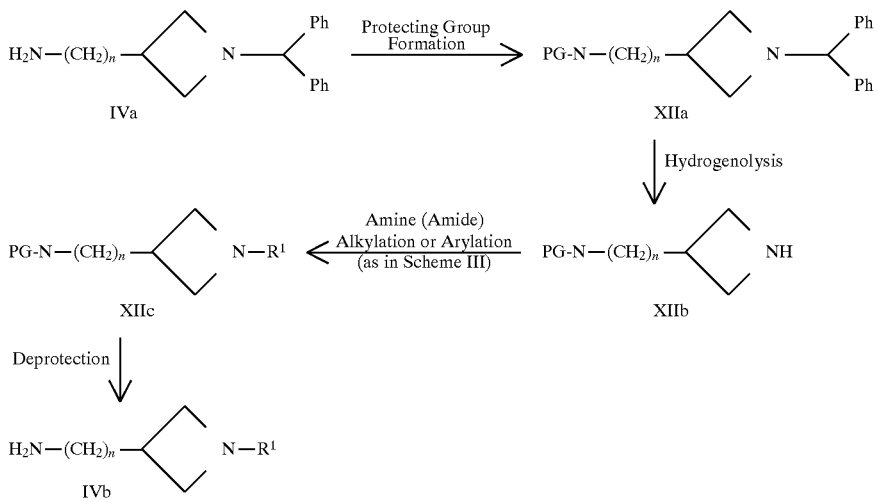

Schemes VI and VII.
General Routes to II
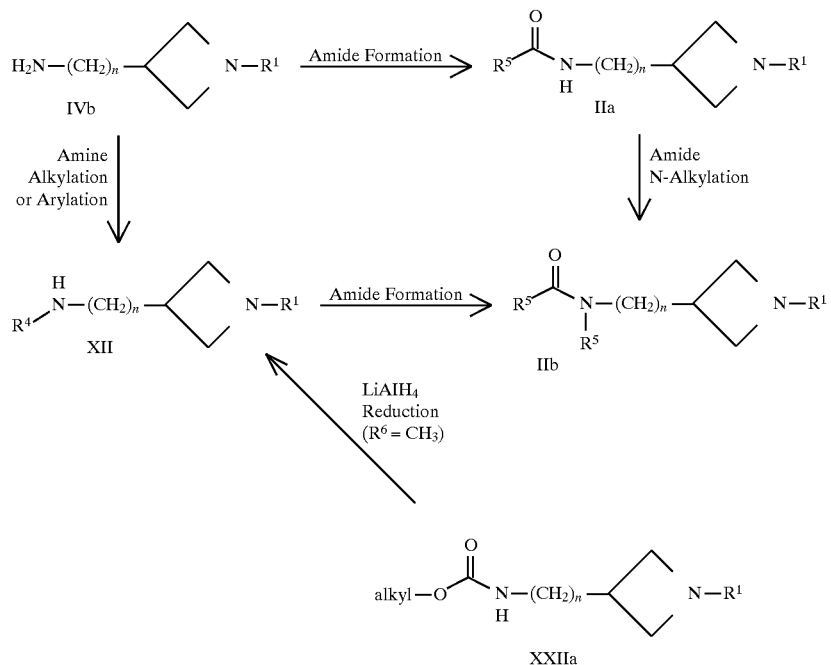
Scheme VIII
Preparation of Compounds I$^b$, I$^c$
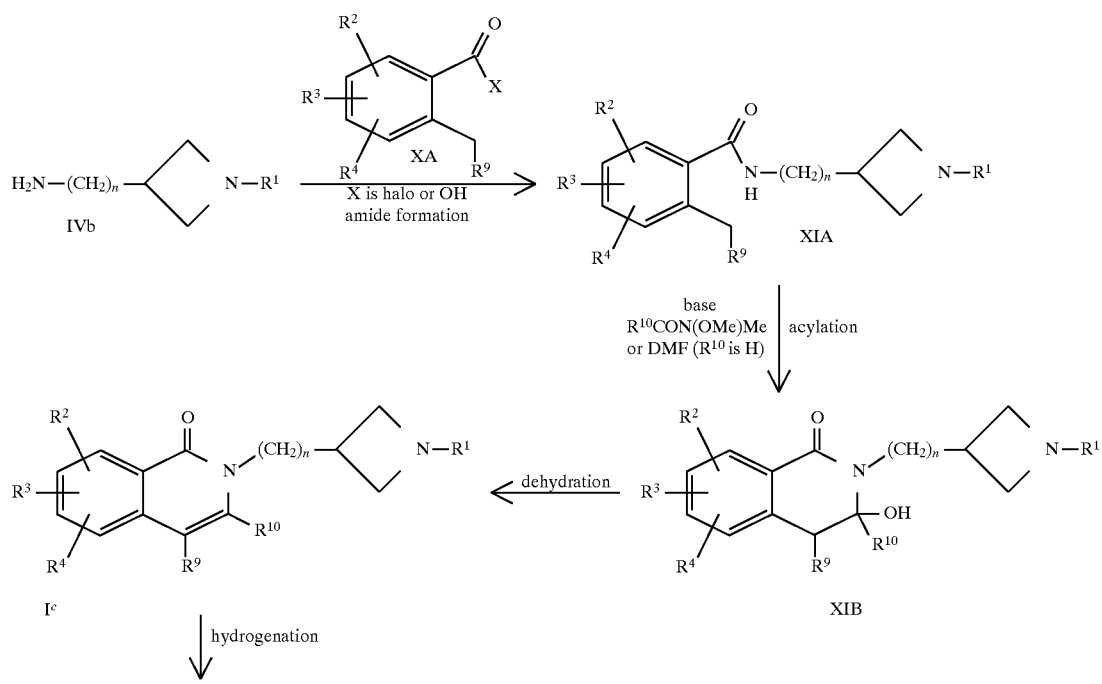

-continued
Scheme VIII
Preparation of Compounds I$^b$, I$^c$

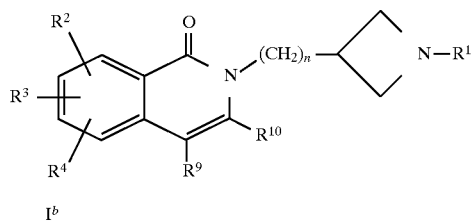

I$^b$

Scheme IX
Preparation of Compounds IA$^1$–IA$^2$

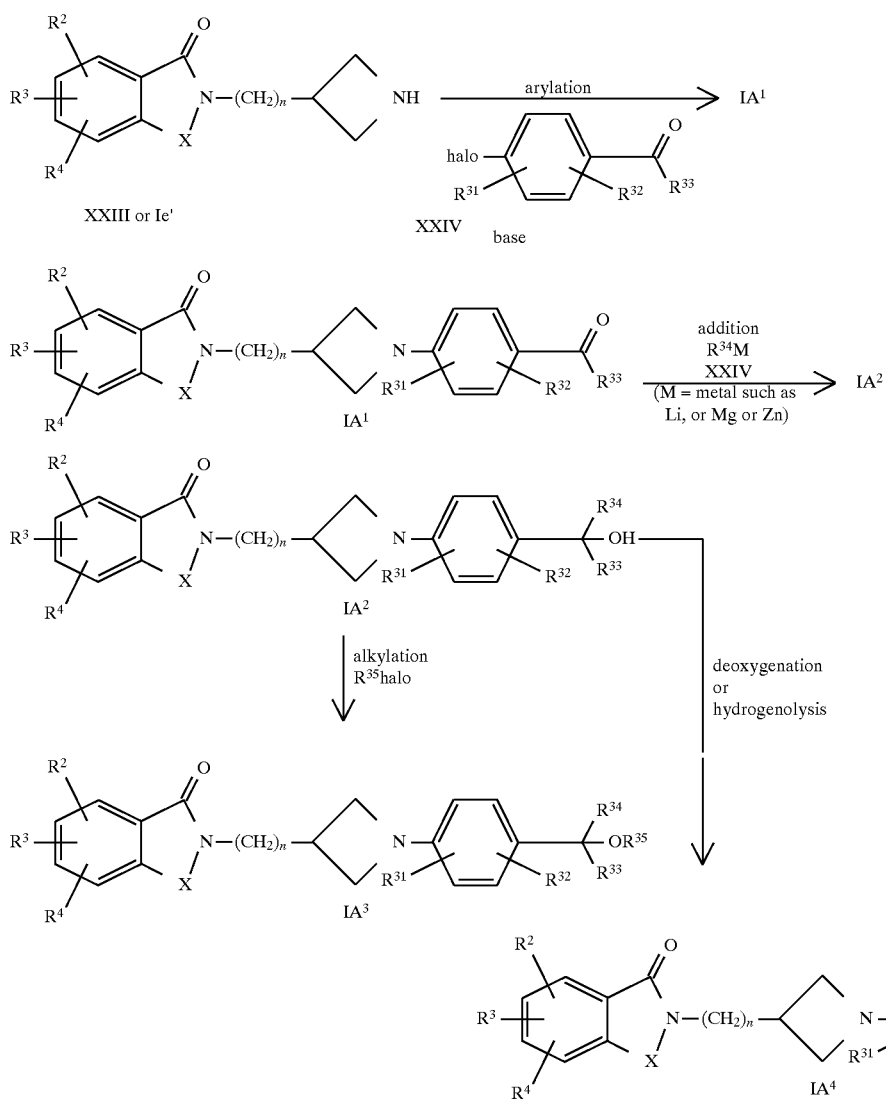

R$^{31}$ and R$^{32}$ are independently selected from any of the R$^2$, R$^3$, or R$^4$ radicals;

R$^{33}$ and R$^{34}$ are independently selected from any of the R$^1$ radicals as well as aryloxy, alkoxy, arylalkoxy, heteroarylalkoxy and heteroaryloxy;

R$^{35}$ can be any of the R$^1$ radicals.

Scheme X
Preparation of Compound I$^a$
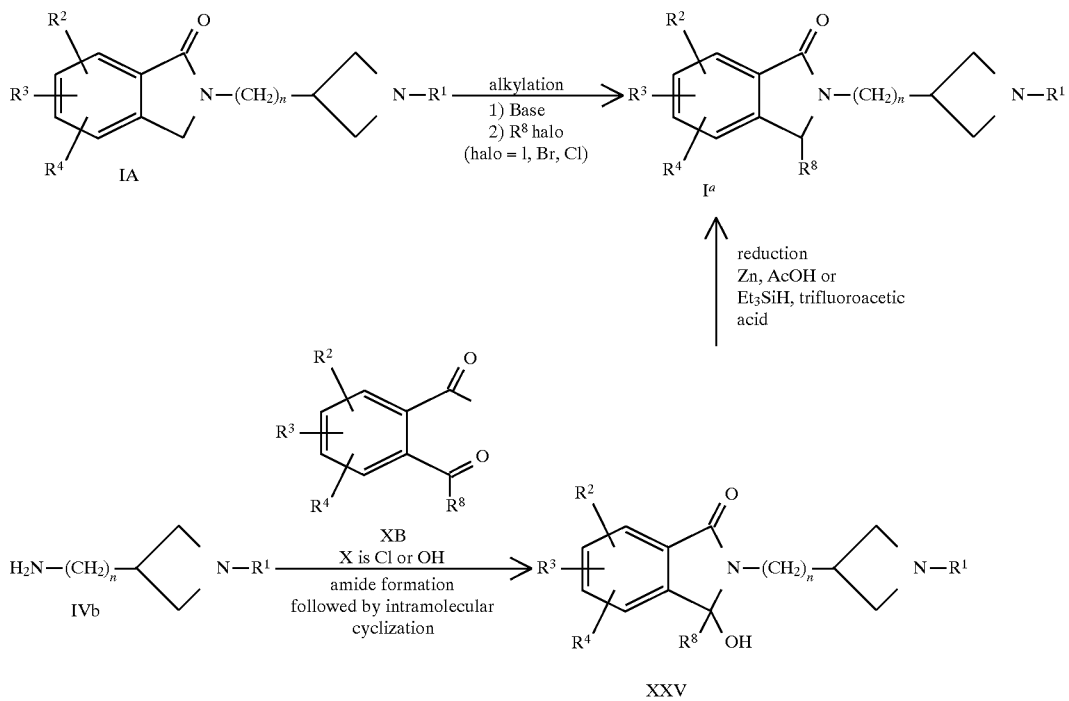
Scheme XI
Preparation of Compound II
(Robotic Amide Coupling)
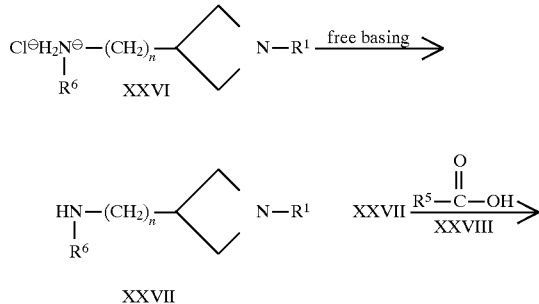
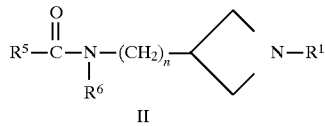
-continued
Scheme XI
Preparation of Compound II
(Robotic Amide Coupling)
In the following Schemes XII et al, in the fluorenyl rings or fluorenyl analogs, the fused aryl groups:
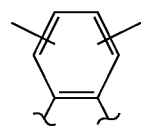
may each optionally be replaced by a 5- or 6-membered heteroaryl ring as defined herein.

Scheme XII
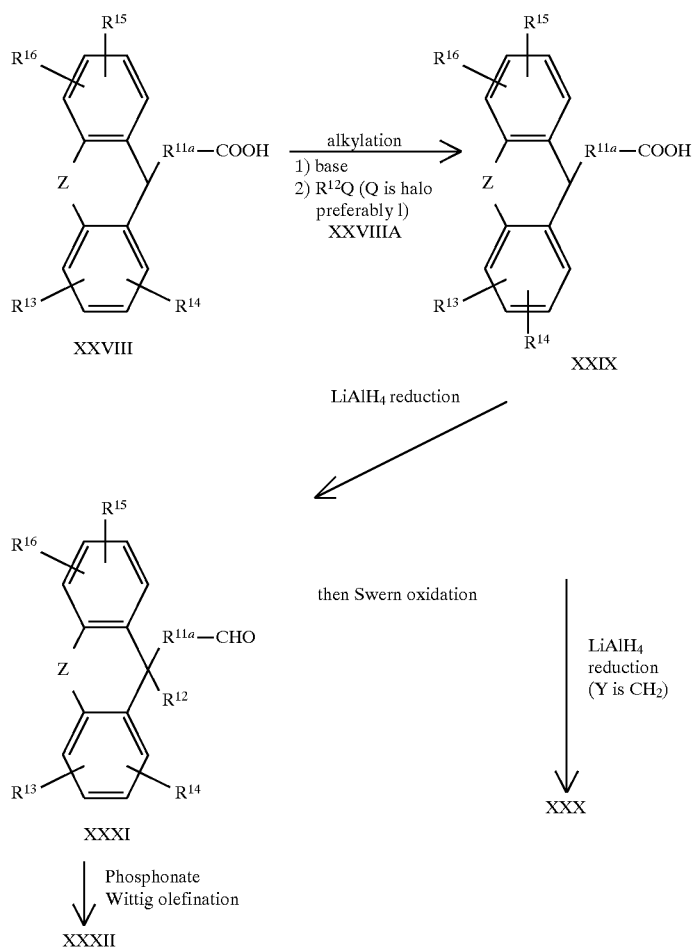
$R^{11a}$ can be any of the $R^{11}$ radicals.
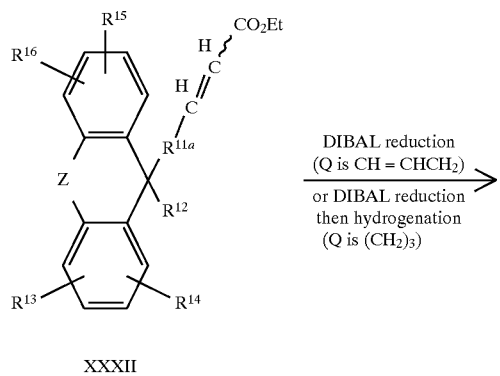
XXXII

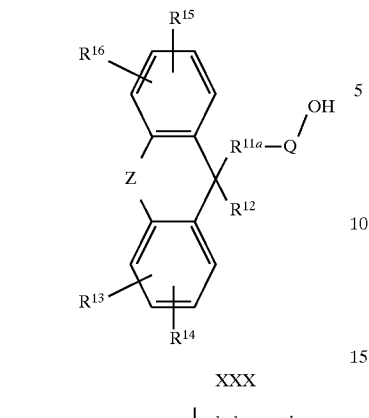
XXX
↓ halogenation or sulfonation
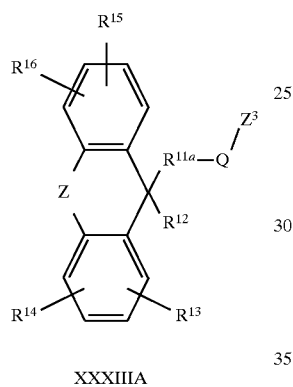
XXXIIIA
$Z^3$ is halo or Osulfonate
Scheme XIII
Preparation of Intermediates where $Z^2$ is S, SO or $SO_2$
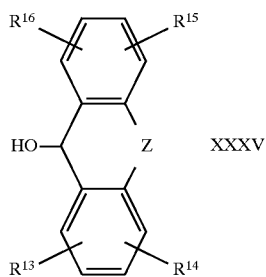  XXXV
↓ acid treatment
   $R^{12}SH$ -continued
Scheme XIII
Preparation of Intermediates where $Z^2$ is S, SO or $SO_2$
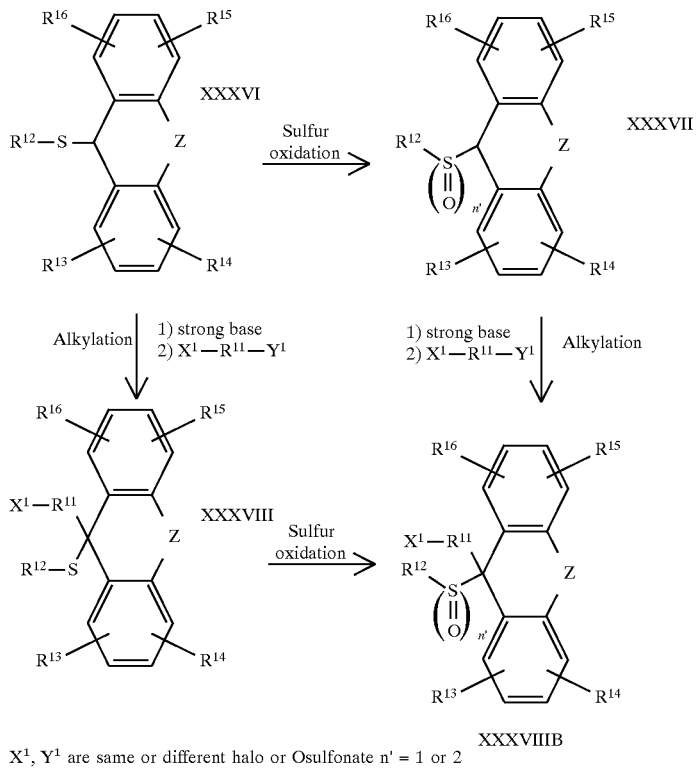
$X^1$, $Y^1$ are same or different halo or Osulfonate n' = 1 or 2
Scheme XIVA
Preparation of A (Intermediates where $Z^2$ is NHCO)
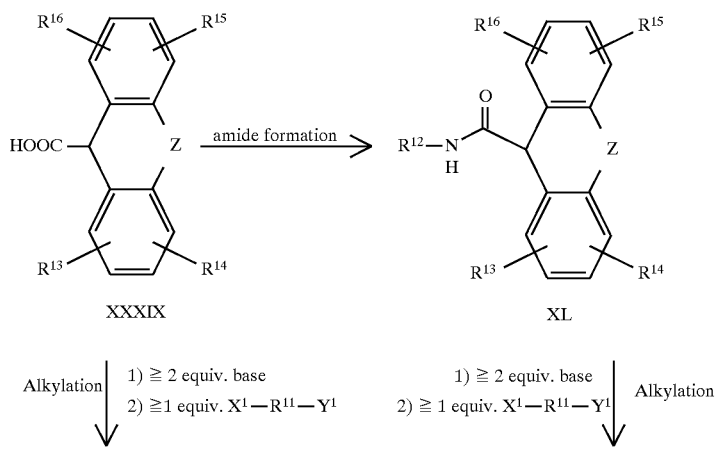

Scheme XIVA
Preparation of A (Intermediates where $Z^2$ is NHCO)

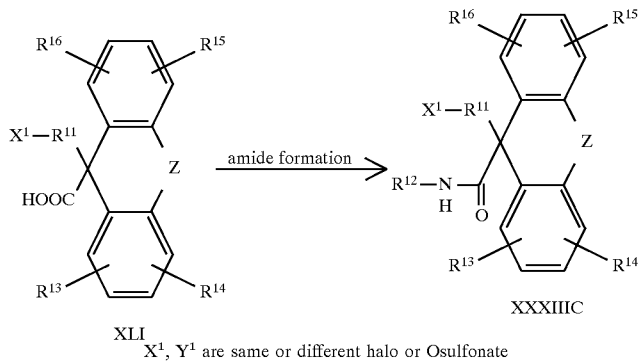

XLI
$X^1$, $Y^1$ are same or different halo or Osulfonate

Scheme XIVB
Alternating Procedure for Preparing Intermediate XL
(Shown in Scheme XIVA)

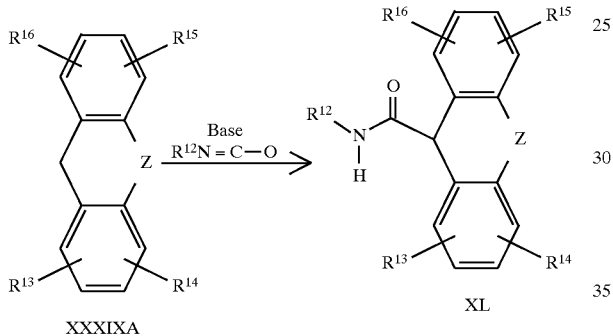

In carrying out the above reaction, bases such as n-butyllithiun, lithium bis(trimethylsilyl) amide and sodium bis(trimethylsilyl) amide may be employed in an aprotic solvent such as THF, at between −78° C. and 35° C.

It is preferable to have the starting material and isocyanate ($R^{12}N = C - O$) together in solvent, and then add the base, and optionally add further excess isocyanate subsequently.

Scheme XV
Preparation of Intermediate where $Z^1$ is $-N-C-$ with H on N and =O on C

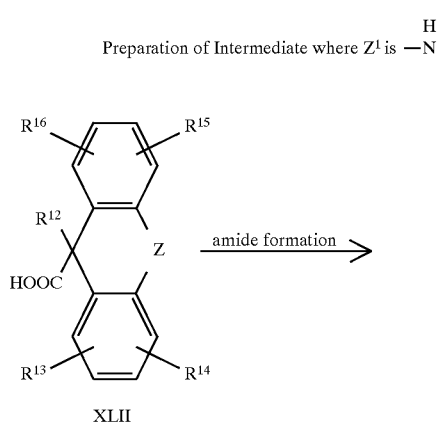

XLII

-continued
Scheme XV

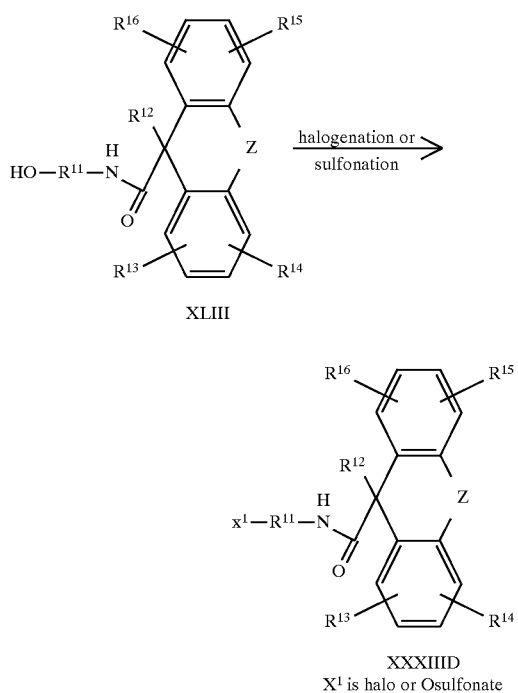

XLIII

XXXIIID
$X^1$ is halo or Osulfonate

Scheme XVI

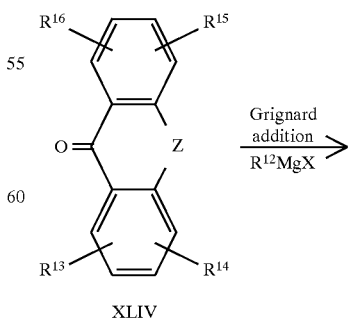

XLIV

-continued
Scheme XVI
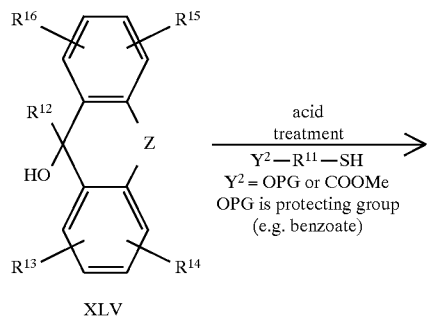
XLV
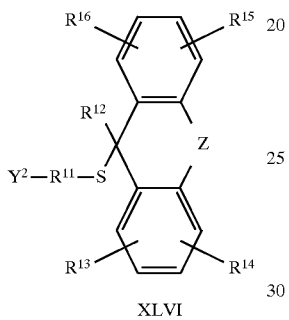
XLVI
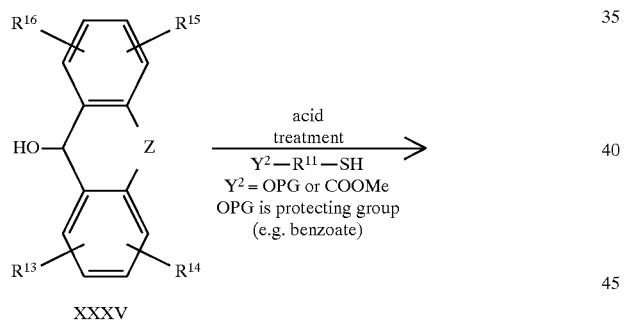
XXXV
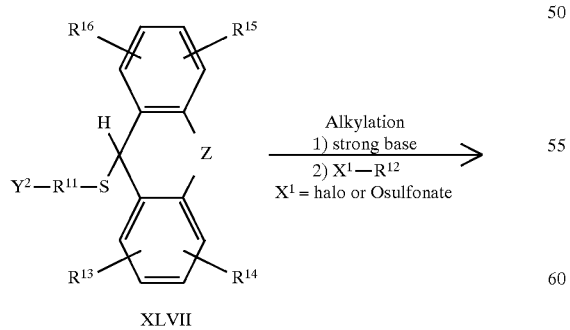
XLVII
-continued
Scheme XVI
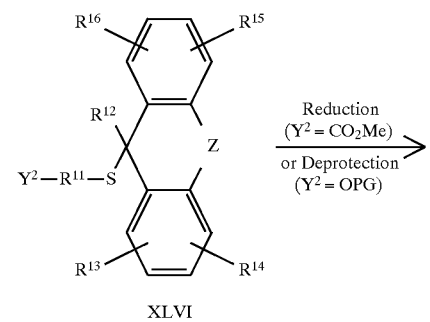
XLVI
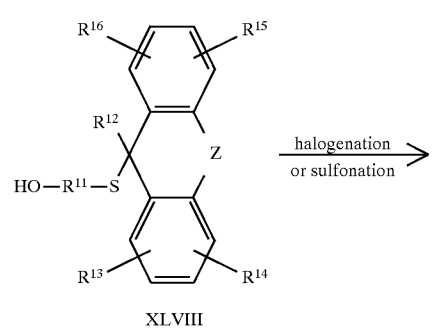
XLVIII
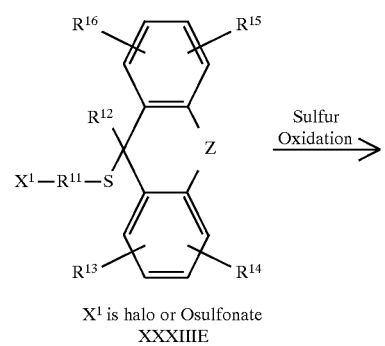
$X^1$ is halo or Osulfonate
XXXIIIE
XXXIIIF (n' = 1)
XXXIIIG (n' = 2)

Scheme XVIA
Preparation of Ketones
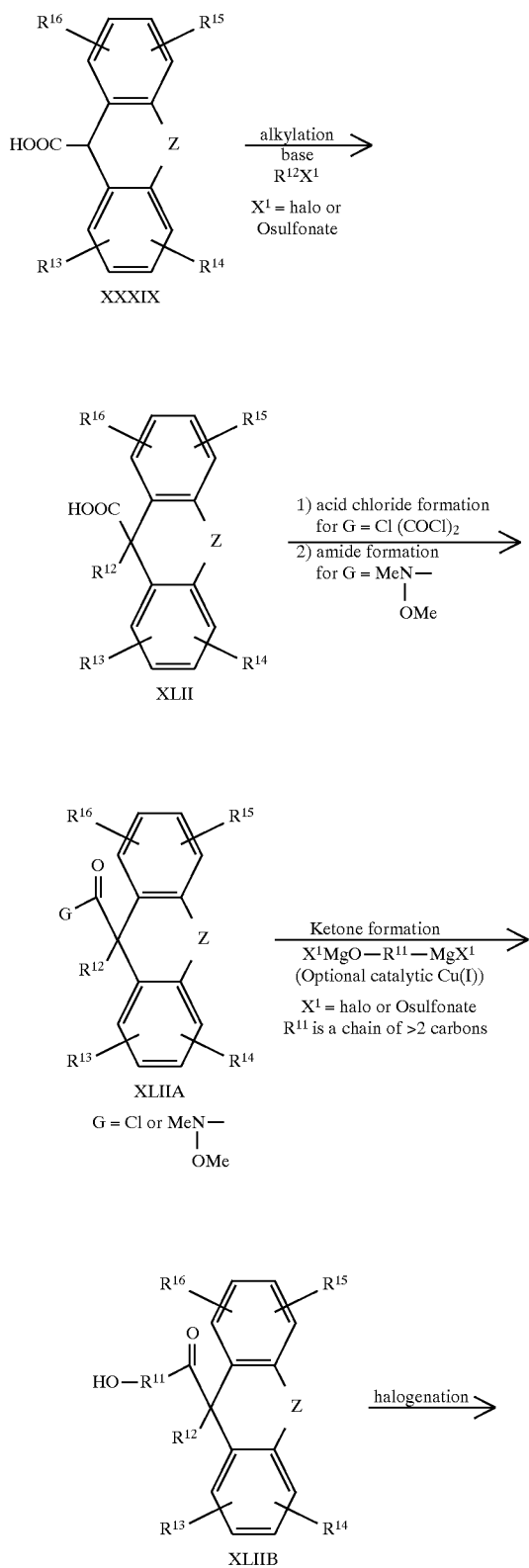
-continued
Scheme XVIA
Preparation of Ketones
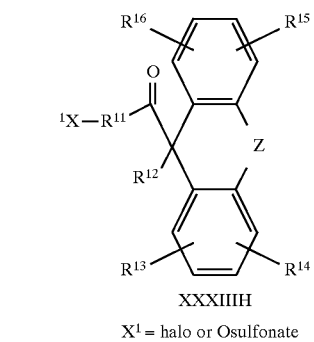
$X^1$ = halo or O-sulfonate
Scheme XVIB.
Preparation of Ketones (Preferred Route)
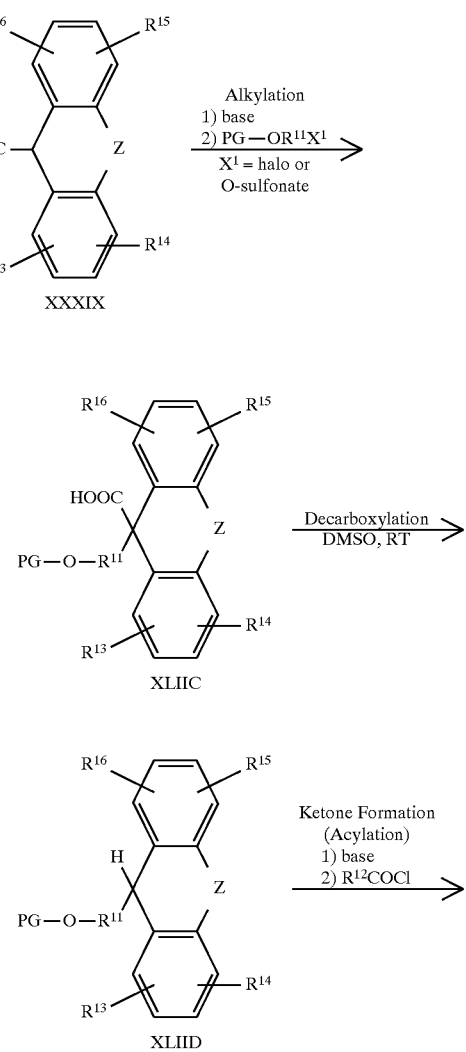

Scheme XVIB.
Preparation of Ketones (Preferred Route)
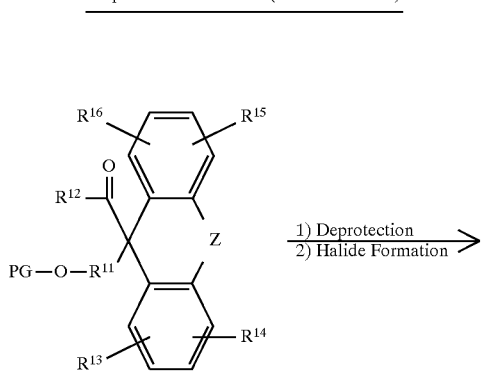
XLIIE
1) Deprotection
2) Halide Formation →
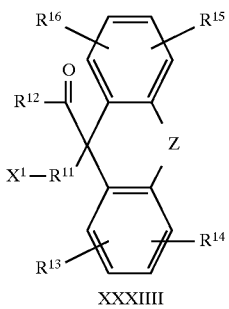
XXXIIII
PG is an appropiate protecting group:
such as t-butyl(dimethyl)silyl or
t-butyl(diphenyl)silyl, which can be
deprotected with aqueous acid of n-Bu₄NF.
Scheme XVIIA
Preparation of Amide Linked Compounds
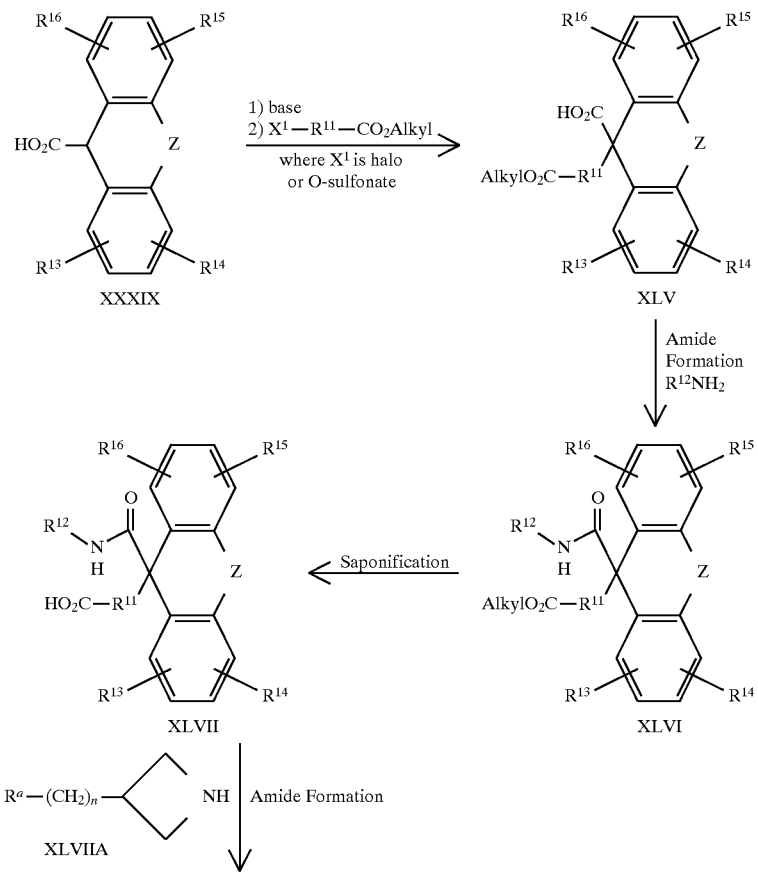

-continued
Scheme XVIIA
Preparation of Amide Linked Compounds
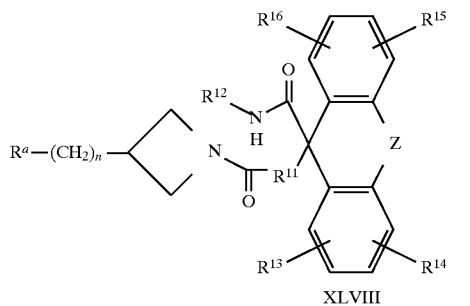
XLVIII
R$^a$ is
Scheme XVIIB
Preparation of Carbamate and Urea Linked Compounds -continued
Scheme XVIIB
Preparation of Carbamate and Urea Linked Compounds
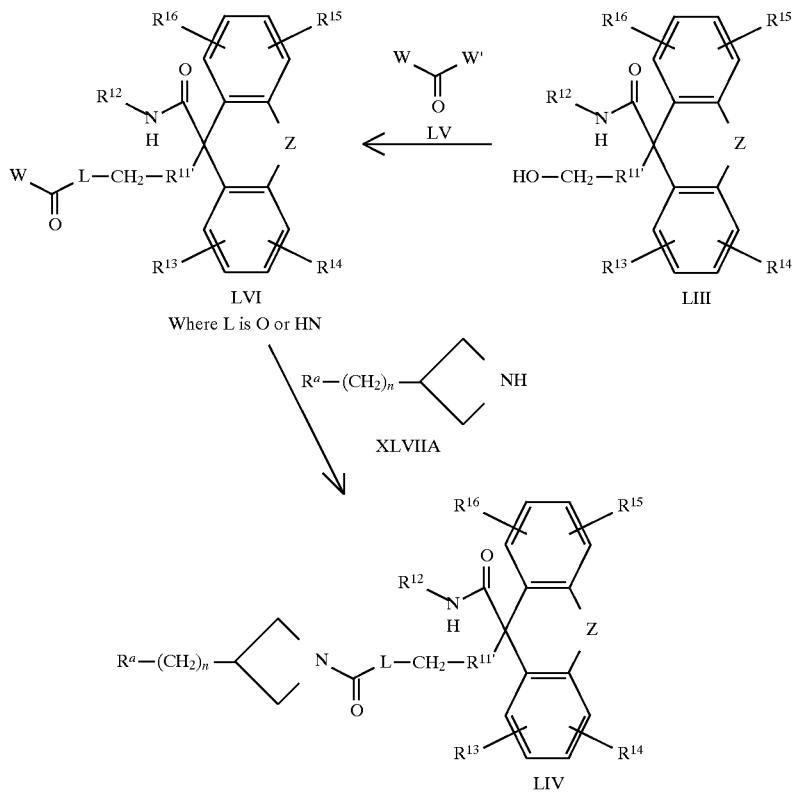
Scheme XVIIIA
Formation of Sulfonamides
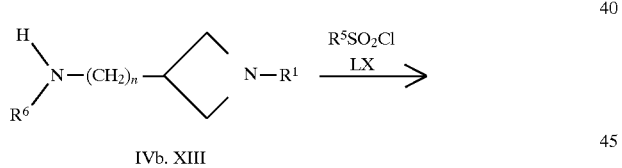
Scheme XVIIIB
Formation of Ureas ($R^5$ is Amino)
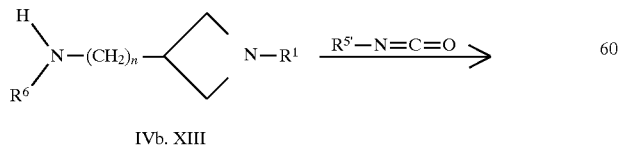
-continued
Scheme XVIIIB
Formation of Ureas ($R^5$ is Amino)
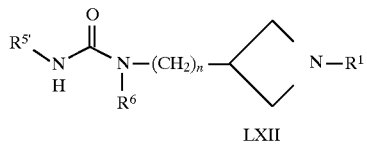
Scheme XIXA
General Route to Final Product
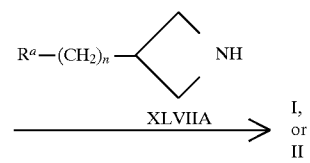
$R^1-X^1$
(where $R^1$ is as in XXXIII A–K or any other $R^1$ is defined herein)

Scheme XIXB
General Route to Final Products (I or II)
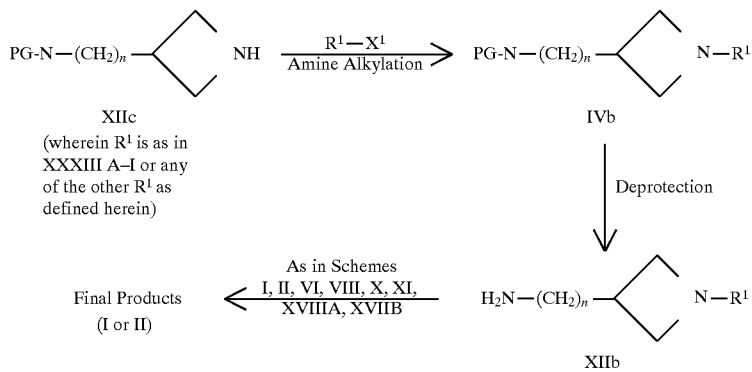
(Example of a protected nitrogen (PG-N) is the t-BuOC=ONH (BOC amino) group, which can be deprotected under mild conditions, such as anhydrous HCl in dioxane or neat trifluoroacetic acid).
Scheme XX
Oxidation of sulfur at the end of the reaction sequence
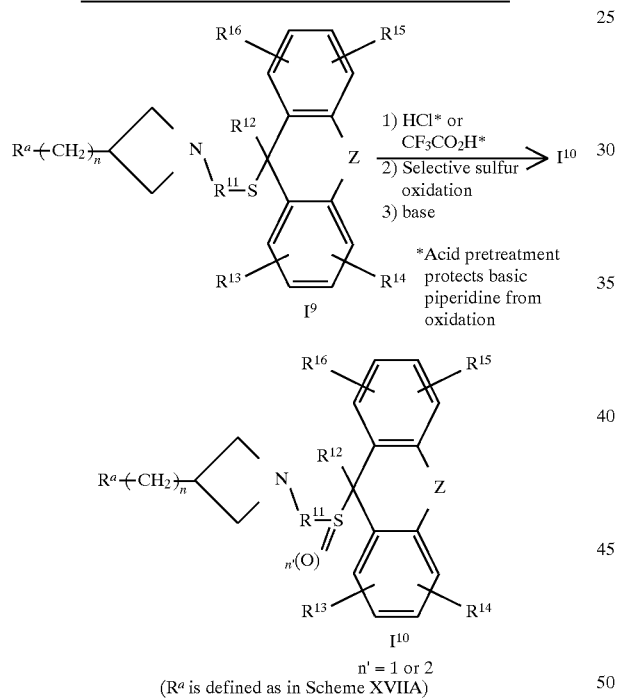
n' = 1 or 2
($R^a$ is defined as in Scheme XVIIA)

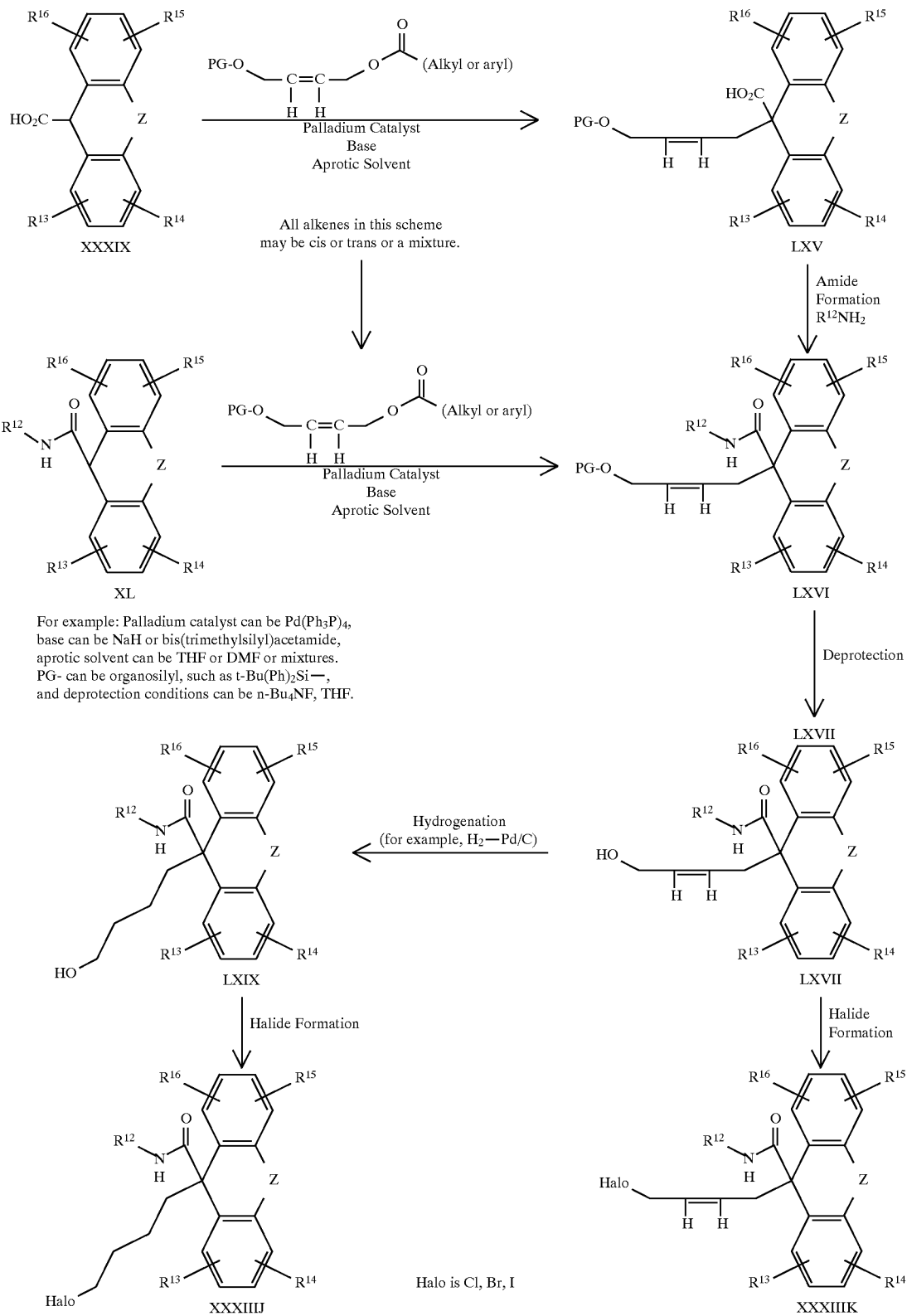

Scheme XXII
Preparation of N-Oxides of Formulae I and II Compounds

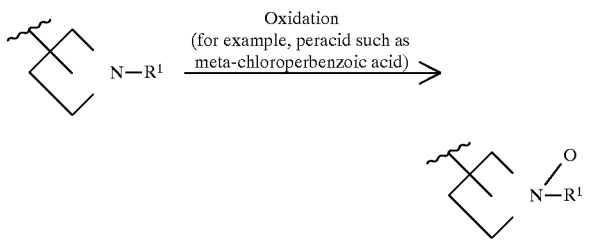

In the above Reaction Schemes XII through XXI, the starting fluorenyl-type acid XXVIII, alcohol XXXV, acids XXXIX and XLII, ketone XLIV, hydride XXXIXA, and amide XL groups may be substituted with corresponding acid, alcohol, ketone, hydride and amide containing fluorenyl type groups as set out in A, B, C and D or indenyl-type groups as set out in E, F, G and/or H to provide an intermediate compound for use in preparing a compound of formula I or II of the invention as per Reaction Schemes I to XXII.

Phthalimide formation (Reaction Schemes I and IV) may be carried out by heating to about 80° to 150° C. in an oil bath optionally in an inert solvent or by various other procedures known in the art.

Reduction (Reaction Scheme I) may be carried out by treatment with such reducing agents as zinc in the presence of acetic acid or tin in the presence of hydrochloric acid under an inert atmoshphere (e.g., argon).

Isoindolone formation (Reaction Scheme I) may be carried out by heating in the range of about 50° to 150° C. in an organic solvent (e.g., toluene, ethanol, dimethylformamide) optionally in the presence of a salt (e.g., potassium carbonate) or a tertiary amine base (e.g., 2,6-di-t-butyl-pyridine or triethylamine).

Amide formation (Reaction Schemes II, VI, VII, VIII, X, XI, XIVA, XV, XVI, XVIA, XVIB, XVIIA, XVIIB, XXI), may be carried out by a number of methods known in the art. For example, an amine substrate may be treated with (1) an acid halide $R^5C(O)$halo or compound X or XA in an aprotic solvent, optionally in the presence of a tertiary amine base (e.g., triethylamine); (2) the acid halide in the presence of an aqueous base under Schotten-Baumann conditions; (3) a free carboxylic acid ($R^5CO_2H$) in the presence of a coupling agent such as dicyclohexylcarbodiimide (DCC), diisopropyl carbodiimide (DIC) or 1-(3-dimethylamino-propyl)-3-ethylcarbodiimide hydrochloride (WSC), optionally in the presence of 1-hydroxybenzotriazole (HOBT); (4) the free acid in the presence of N, N-carbonyl-diimidazole in an aprotic organic solvent followed by the amine substrate; (5) trialkylaluminum (e.g., $Al(CH_3)_3$) in an aprotic solvent, followed by an ester (e.g., $R^5CO_2$alkyl or compound VIII) or (6) mixed anhydride formation, by reacting the acid with an acid chloride (e.g., isobutyl chloroformate or bis-(2-oxo-3-oxazolidinyl)-phosphinic chloride (Bop-Cl)) in the presence of a tertiary amine base (e.g., triethylamine) followed by treatment with the amine substrate.

Mesylate formation (Reaction Scheme II) may be carried out by treatment of the amine-alcohol substrate with methanesulfonyl chloride and triethylamine or pyridine or in an aprotic solvent, such as dichloromethane.

Base cyclization (Reaction Schemes II, VIII, XXII) may be carried out by treatment with a base (e.g., potassium t-butoxide, lithium hexamethyl-disilazide ($LiN(TMS)_2$) or sodium hydride) in an inert solvent (e.g., dimethylformamide, tetrahydrofuran, dimethoxymethane, or toluene). Mitsunobu cyclization (Reaction Scheme II) may be carried out by procedures generally known in the art. See, e.g., R. K. Olsen, *J. Org. Chem.*, 49, 3527 (1984); Genin, M. J., et al., *J. Org. Chem.*, 58, 2334–7 (1993).

Alternatively, a mixture of compounds IV and VIII can be converted to compound Ia in a single pot by heating the mixture in a protic solvent (e.g., water, methanol, ethenyl or isopropanol or mixtures thereof) at 100° to 200° C. See, e.g., European patent application 81/26,749, FR 2, 548,666 (1983).

Protection and deprotection (Reaction Schemes III, IV, V, XVI, XVIB, XIXB, XXI) may be carried out by procedures generally known in the art. See, for example, T. W. Greene, *Protecting Groups in Organic Synthesis*, Second edition, 1991. PG in Scheme V denotes a nitrogen-protecting group. One particularly useful group is tert-butoxy-carbonyl (BOC) which can be derived from the associated anhydride as shown in Scheme IV. BOC-protected amines may typically be deprotected by treatment with acid (e.g., trifluoroacetic acid or hydrochloric acid) in procedures well understood by those having ordinary skill in the art.

Hydrogenolysis (Reaction Schemes III, IV, V) may be carried out with $H_2$ using a balloon apparatus or a Parr Shaker in the presence of a catalyst (e.g., pallladium on activated carbon).

Amine/Amide alkylation and arylation (Reaction Schemes III, IV, V, IX, XII, XIXA, XIXB) may be carried out by methods known in the art. Suitable procedures are described in Cortizo, L., *J. Med. Chem.* 34, 2242–2247 (1991). For example, the alkylation or arylation may be carried out by treating the amine substrate with a halide (e.g., $R^1$-halo) or an oxytosylate (e.g., $R^1$-O-tosylate) in an aprotic solvent (e.g., dimethylformamide), optionally in the presence of a tertiary amine (e.g., triethylamine), an inorganic base (e.g., potassium carbonate, NaH), or lithium hexamethyl-disilazide).

Reductive amination may be employed as an alternative to the foregoing amine alkylation and arylation procedures where W is H,H when $R^1$, $R^6$ or $R^7$ is $R^9R^{10}CH$— and $R^9$ and $R^{10}$ are each independently hydrogen, alkyl, alkenyl, aryl, heteroaryl, arylalkyl, heteroarylalkyl, cycloalkyl, or cycloalkylalkyl, or $R^9$ and $R^{10}$ together are alkylene (i.e., $R^9R^{10}CH$— forms a cycloalkyl group). Such reductive amination may be carried out by treating the amine with (a) a ketone or aldehyde ($R^9$—C(O)—$R^{10}$), (b) $NaBH_4$, $NaBH_3CN$ or $NaB(acetoxy)_3H$, (c) a protic solvent (e.g., methanol) or a dipolar aprotic solvent (e.g., acetonitrile), and, optionally, (d) an acid (e.g., acetic acid, trifluoroacetic acid, hydrochloric acid, or titanium isopropoxide). When $R^1$ is aryl or heteroaryl, transition metals (e. g., palladium or copper salts or complexes) may be used to promote the arylation reaction.

Alkylation of the isoindolone (Reaction Scheme X) may be carried out by treatment of the isoindolone with a strong base (i.e. sodium bis(trimethylsilyl)-amide or lithium diisopropylamide) followed by an alkyl halide (e.g. $R^8$-halo) or alkyl sulfonate (e.g. $R^8$-tosylate) in an inert solvent (e.g. tetrahydrofuran or dimethoxyethane). Alternatively, as seen in Scheme X, amine IVb can be treated under amide formation conditions with a ketone with the structure XB to provide a hydroxylactam XXV, which could be subjected to reduction conditions with such reducing agents as zinc in acetic acid or triethylsilane in trifluoroacetic acid to give $I^a$.

Hydrazinolysis of phthalimides may be carried out by standard means known in the art. See, e.g., T. W. Greene, *Protecting Groups in Organic Synthesis*, Second edition, 1991.

Amide N-alkylation (Reaction Scheme VI) may be carried out by base treatment (e.g., NaH, KH, KN[Si(CH$_3$)$_3$]$_2$, K$_2$CO$_3$, P4-phosphazene base, or butyl lithium) in an aprotic organic solvent, followed by treatment with R$^6$-halo or R$^6$-O-tosylate. Use of P-phosphazene base is described in T. Pietzonka, D. Seebach, *Angew. Chem. Int. Ed. Engl.* 31, 1481, 1992.

Compound III can also be prepared from compound XX as described by Cortizo, L., *J. Med. Chem.* 34, 2242–2247 (1991).

Dehydration (Scheme VIII) may be carried out employing a strong acid such as hydrochloric acid, sulfuric acid or trifluoroacetic acid.

Hydrogenation (Scheme VIII) may be carried out in the presence of a conventional catalyst such as Pd/C or Pt or Rh under a H$_2$ atmosphere.

The addition reaction shown in Scheme IX may be carried out by treating IA$^1$ with an organometallic reagent XXIV, such as an organolithium or organic magnesium compound where organo is alkyl or aryl.

The deoxygenation or hydrogenation reaction (Scheme IX) is carried out in the presence of a strong acid such as trifluoroacetic acid or boron trifluoride etherate, in the presence of a hydride source such as triethyl silane or tris(trimethylsilyl)silane.

The alkylation in Schemes XII, XIII, XIV, XVI, XVIA, XVIB is carried out in the presence of base such as butyllithium or sodium bis(trimethylsilyl)-amide. It will be appreciated that R$^{12}$ in R$^{12}$Q may be any of the R$^{12}$ groups as defined hereinbefore.

Alternatively, the alkylation in the above Schemes can be performed where either or both Z$^1$ or Z$^2$ is a bond, using a palladium catalyzed allylic alkylation procedure. In this reaction, the fluorenyl-type or indenyl-type precursors (compounds XXVIII, XXXVI, XXXVII, XXXIX, XL, XLVII) are reacted with a base (sodium hydride, sodium bis(trimethylsilyl)amide or bis(trimethylsilyl)acetamide), a palladium catalyst (for example Pd(Ph$_3$)$_4$) and an allylic acetate

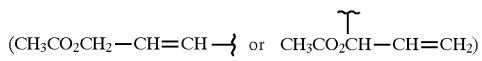

in an inert solvent (for example THF). This reaction is to introduce either -R$^{12}$ (Scheme XII) or -R$^{11}$-X$^1$ (Schemes XIII, XIV, XVI, XVIA) or -R$^{11}$-OPG (Scheme XVIB, Scheme XXI). The product of this reaction contains either an -R$^{12}$ group or an -R$^{11}$-X$^1$ group (or an -R$^{11}$-OPG group) which begins with

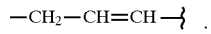

Saturation of the alkene in R$^{11}$ or R$^{12}$ can be accomplished by standard catalytic hydrogenation conditions.

With respect to Scheme XII, the LiAlH$_4$ reduction, Swern oxidation, Wittig olefination and halogenation/sulfonation reactions are conventional reactions well known to those skilled in the art.

The sulfur oxidation in Schemes XIII, XVI and XVIII is carried out as follows.

Sulfides of structures XXXVI, XXXVIII, XXXIIIE and I$^9$ can be selectively oxidized to sulfoxides by 1 molar equivalent of reagents known in the art, such as 30% H$_2$O$_2$, NaIO$_4$, and peracids (e.g., metachloroperbenzoic acid). The resulting sulfoxides can be further transformed to corresponding sulfones by another molar equivalent or excess of 30% H$_2$O$_2$, KMnO$_4$, KHSO$_5$, or peracids (e.g., metachloroperbenzoic acid). Alternatively, the sulfones can be directly prepared from sulfides with 2 molar equivalents or more of oxidizing agents, such as 30% H$_2$O$_2$ and peracids (e.g., metachloroperbenzoic acid). In cases where an amine (such as an azetidine in I$^9$) is present during the oxidation, the basic nitrogen may be protected by pretreatment with an acid such as HCl or CF$_3$CO$_2$H (see Scheme XIX).

To prepare examples where Z$^1$ or Z$^2$ is —CHOH, the compounds I and II where Z$^1$ or Z$^2$ is C=O can be reduced with a hydride reagent, for example NaBH$_4$.

Preparation of the protected aminoazetidine starting material IVd (Scheme (1)) can be performed by reaction of the known methanesulfonate (Anderson and Lok, J. Org. Chem. 1972, 37, 3953–3955) with ammonia via the procedure of Frigola, et al, J. Med. Chem. 1995, 38, 1203–1215. Alternatively, compound IVd can be prepared via the procedure of Nisato and Frigerio, U.S. Pat. No. 4,943,641.

Preparation of the aminomethylazetidine starting material IVe may be accomplished as described in J. Org. Chem. 1972, 37, 3953–3955.

The compounds of the invention may be employed in preventing, stabilizing or causing regression of atherosclerosis in a mammalian species by administering a therapeutically effective amount of a compound to decrease the activity of MTP.

The compounds of the invention can be tested for MTP inhibitory activity employing the procedures set out in U.S. application Ser. No. 117,362 filed Sep. 3, 1993, U.S. Pat No. 5,595,872 employing MTP isolated from one of the following sources:

(1) bovine liver microsomes,
(2) HepG$_2$ cells (human hepatoma cells) or
(3) recombinant human MTP expressed in baculovirus.

The compounds of the invention may also be employed in lowering serum lipid levels, such as cholesterol or triglyceride (TG) levels, in a mammalian species, by administering a therapeutically effective amount of a compound to decrease the activity of MTP.

The compounds of the invention may be employed in the treatment of various other conditions or diseases using agents which decrease activity of MTP. For example, compounds of the invention decrease the amount or activity of MTP and therefore decrease serum cholesterol and TG levels, and TG, fatty acid and cholesterol absorption and thus are useful in treating hypercholesterolemia, hypertriglyceridemia, hyperlipidemia, pancreatitis, hyperglycemia and obesity.

The compounds of the present invention are agents that decrease the activity of MTP and can be administered to various mammalian species, such as monkeys, dogs, cats, rats, humans, etc., in need of such treatment. These agents can be administered systemically, such as orally or parenterally.

The agents that decrease the activity or amount of MTP can be incorporated in a conventional systemic dosage form, such as a tablet, capsule, elixir or injectable formulation. The above dosage forms will also include the necessary physiologically acceptable carrier material, excipient, lubricant, buffer, antibacterial, bulking agent (such as mannitol), antioxidants (ascorbic acid or sodium bisulfite) or the like. Oral dosage forms are preferred, although parenteral forms are quite satisfactory as well.

The dose administered must be carefully adjusted according to the age, weight, and condition of the patient, as well as the route of administration, dosage form and regimen, and the desired result. In general, the dosage forms described above may be administered in amounts of from about 5 to about 500 mg per day in single or divided doses of one to four times daily.

The following Examples represent preferred embodiments of the invention. All temperatures are in °C. unless indicated otherwise.

EXAMPLE 1

N-(2,2,2-Trifluoroethyl)-9-[5-[3-[[[4'-(trifluoromethyl)[1,1'-biphenyl]-2-yl]carbonyl]amino]-1-azetidinyl]pentyl]-9H-fluorene-9-carboxamide, monohydrochloride

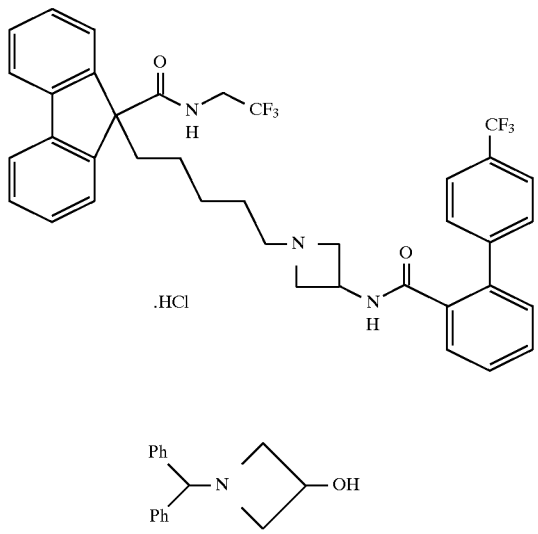

A.

A mixture of epichlorohydrin (19.6 mL, 0.25 mol), benzhydrylamine (43.1 mL, 0.25 mol) and methanol (100 mL) was stirred at RT for 3 days and then refluxed for 2 days. The methanol was removed (reduced pressure) and the residue was washed with acetone (4×150 mL). After drying under high vacuum, a white solid was obtained (37.4 g, 54%). The product (10 g, 41.7 mmol) was partitioned between ethyl ether and 1N NaOH solution and removal of the solvent from the dried ethereal solution gave title compound (8.5 g, 97%) as a white solid (m.p. 108°–110° C.).

B.

To a stirred solution of Part A compound (5.0 g, 20.8 mmol) and triethylamine (4.61 mL, 33.3 mmol) in dichloromethane (35 mL) at 0° C. was added dropwise a solution of methanesulfonyl chloride (2.42 mL, 31.2 mmol) in dichloromethane (15 mL). The reaction was stirred at 0° C. for 10 min. The reaction was washed with water (2×10 mL), brine (2×10 mL) and dried over MgSO$_4$. Evaporation gave title compound (6.6 g, 100%) as an off-white waxy solid.

C.

A mixture of Part B compound (6.5 g, 20.4 mmol), 2-propanol (40 mL) and ammonium hydroxide (30%, 24 mL, 200 mmol) was heated at 70° C. for 2 hr. The solvent was removed in vacuo, and the resulting solution was alkalinized with sodium carbonate and extracted with dichloromethane. Evaporation gave a yellow oil. Purification was performed by flash chromatography on silica gel (500 g), loaded and eluted with 2% methanol in dichloromethane containing 0.5% ammonium hydroxide. Pure fractions were combined and evaporated to give title compound (2.0 g, 41%) as a pale yellow oil.

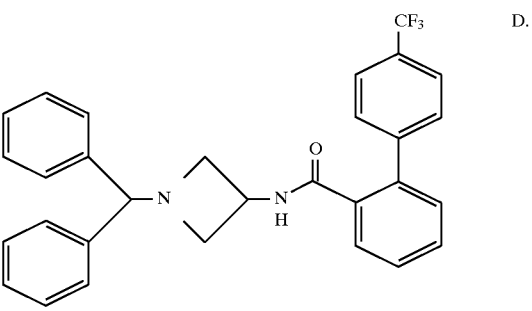
D.

A mixture of Part C compound (320 mg, 1.34 mmol), 4'-(trifluoromethyl)-2-biphenylcarboxylic acid (392 mg, 1.47 mmol), 1-hydroxybenzotriazole hydrate (181 mg, 1.34 mmol), ethyl-3-(3-dimethylamino)-propyl carbodiimide hydrochloride (334 mg, 1.74 mmol) and triethylamine (0.19 mL, 1.34 mmol) in dichloromethane (10 mL) was stirred at RT overnight. The reaction was diluted with dichloromethane (30 mL) and the solution was washed with water (2×15 mL), saturated sodium bicarbonate (2×15 mL), brine (2×15 mL) and dried over MgSO$_4$. Purification was performed by flash chromatography on silica gel (50 g), loaded and eluted with 1.5% methanol in dichloromethane containing 0.2% ammonium hydroxide. Pure fractions were combined and evaporated to give title compound (620 mg, 95%) as a white solid (m.p. 156°–160° C.).

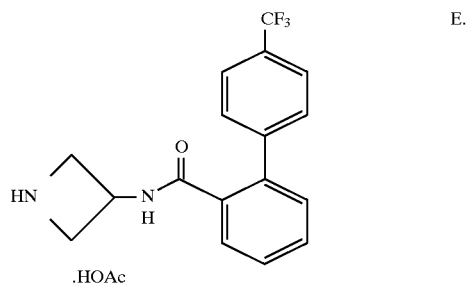
E.

A mixture of Part D compound (280 mg, 0.58 mmol), acetic acid (33 μL, 0.58 mmol) and 10% palladium on carbon (50 mg) was hydrogenated on a Parr shaker at RT and 50 psi overnight. The mixture was filtered through Celite and the filtrate was evaporated to dryness to give title compound (200 mg) as an off-white solid which was carried on without purification.

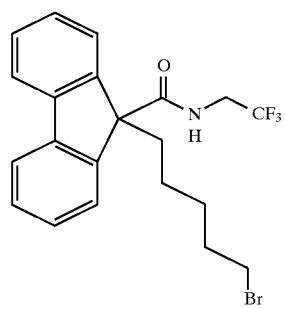
F.

To a solution of 9-fluorenecarboxylic acid (10 g, 47.6 mmol) in THF (200 mL) at 0° C. was added dropwise a solution of n-butyllithium (2.5M, 42 mL, 105 mmol) in THF. The yellow reaction was stirred at 0° C. for 30 min., then 1,5-dibromopentane (16.8 mL, 124 mmol) was added dropwise over 30 min. The reaction was stirred at 0° C. for 30 min, then the reaction was warmed to RT for 30 h. The reaction was extracted with water (3×100 mL) and the combined aqueous layers were extracted with ethyl ether (2×100 mL). The aqueous layer was made acidic with 1N HCl solution, then extracted with dichloromethane (3×150 mL). The combined organic layers were dried over MgSO$_4$. Evaporation gave a crude white solid (15.7 g). To a solution of the crude acid and DMF (20 μL) in CH$_2$Cl$_2$ (200 mL) under argon at 0° C. was added oxalyl chloride (35.7 mL, 2.0M in CH$_2$Cl$_2$, 71.4 mmol) dropwise. The reaction was stirred at 0° C. for 10 min, then warmed to RT and stirred for 1.5 h. The reaction was concentrated in vacuo to give the crude acid chloride as a yellow oil. To a suspension of 2,2,2-trifluoroethylamine hydrochloride (6.45 g, 47.6 mmol) in CH$_2$Cl$_2$ (150 mL) at 0° C. under argon was added triethylamine (14.5 mL, 105 mmol) followed by dropwise addition of a solution of the crude acid chloride in CH$_2$Cl$_2$ (15 mL). The reaction was stirred at 0° C. for 1 h, diluted with CH$_2$Cl$_2$ (300 mL), and washed with water (2×100 mL), 1N HCl (2×100 mL), saturated NaHCO$_3$ (2×100 mL), and brine (2×100 mL), then dried over MgSO$_4$. Evaporation gave 17 g of a oil which was purified by flash chromatography on silica gel (1.5 kg). The crude product was loaded in a mixture of CH$_2$Cl$_2$ and hexane, and eluted with 15% ethyl acetate/hexane. Pure fractions were combined and evaporated to give the title compound (14.7 g, 72%) as a white solid (m.p. 92°–96° C.).

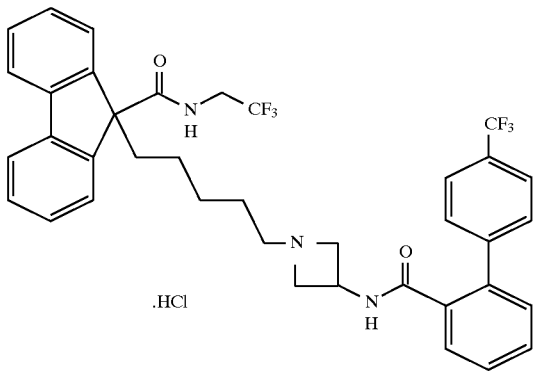

G.

A mixture of Part E compound (200 mg, 0.63 mmol), Part F compound (266 mg, 0.63 mmol) and K$_2$CO$_3$ (95 mg, 0.70 mmol) in DMF (5 mL) was stirred at 50° C. for 16 h. The reaction was evaporated and the residue was partitioned between dichloromethane (60 mL) and water (20 mL). The organic layer was dried over sodium sulfate, then concentrated in vacuo to give a yellow oil, which was chromatographed (2.5% methanol in dichloromethane containing 0.5% ammonium hydroxide) on silica gel (40 g). Pure fractions were combined and evaporated to give a colorless oil (125 mg, 56%). The product was dissolved in MeOH (2 mL), then 1.1M HCl in ethyl ether (1 mL) was added. The reaction was stirred at RT for 10 min. The solution was evaporated and dried under vacuum to give title compound (125 mg, 96%) as a white solid (m.p. 104°–109° C.).

MS (ES, +ions): m/z 680 (M+H).

Anal. Calcd for C$_{38}$H$_{35}$F$_6$N$_3$O$_2$+1.5 HCl+1.1 H$_2$O: C, 60.52; H, 5.17; N, 5.57; Cl, 7.05 Found: C, 60.56; H, 5.05; N, 5.66; Cl, 7.24.

EXAMPLE 2

9-[5-[3-(Benzoylamino)-1-azetidinyl]pentyl]-N-(2,2,2-trifluoroethyl)-9H-fluorene-9-carboxamide, monohydrochloride

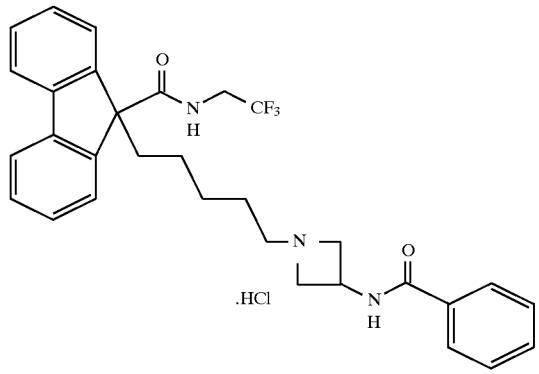

Following the procedure in Example 1 except substituting benzoic acid for 4'-(trifluoromethyl)-2-biphenylcarboxylic acid, title compound was prepared as a white solid.

m.p. 89°–94° C.; MS (ES, +ions): m/z 536 (M+H).

Anal. Calcd for C$_{31}$H$_{32}$F$_3$N$_3$O$_2$+1.3 HCl+1.1 H$_2$O: C, 61.77; H, 5.94; N, 6.97; F, 9.45; Cl, 7.65 Found: C, 61.66; H, 5.61; N, 6.92; F, 9.57; Cl, 7.81.

EXAMPLE 3

N-(2,2,2-Trifluoroethyl)-9-[4-[3-[[[[4'-(trifluoromethyl)[1,1'-biphenyl]-3-yl]carbonyl]amino]methyl]-1-azetidinyl]butyl]-9H-fluorene-9-carboxamide, monohydrochloride

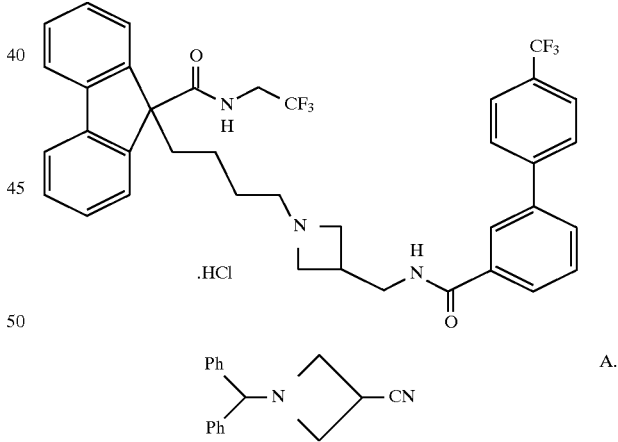

A.

A mixture of Example 1 Part B compound (5.0 g, 15.7 mmol) and sodium cyanide (3.85 g, 78.6 mmol) in DMSO was stirred at 60° C. for 1 h. then warmed to 90° C. Stirring was continued overnight. The reaction was cooled to RT. Dichloromethane (300 mL) was added and the solution was washed with water (2×50 mL), brine (2×50 mL) and dried over MgSO$_4$. Evaporation gave a brown solid. Purification was performed by flash chromatography on silica gel, loaded and eluted with 15% ethyl acetate in hexane. Pure fractions were combined and evaporated to give title compound (2.5 g, 66%) as a white solid (m.p. 151°–155° C.).

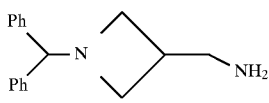
B.

To a solution of Part A compound (1.2 g, 4.82 mmol) in THF (15 mL) at 0° C. was added dropwise 1.0M lithium aluminum hydride in THF. After addition, the reaction was warmed to RT and stirring was continued overnight. A 15% sodium hydroxide solution (15 mL) was added and the mixture was stirred at RT for 4 h. The resulting mixture was filtered through Celite and the filtrate was extracted with ethyl acetate (3×50 mL). The organic layer was washed with water (2×30 mL), brine (2×30 mL) and dried over MgSO$_4$. Evaporation gave title compound (1.05 g, 86%) as a colorless oil.

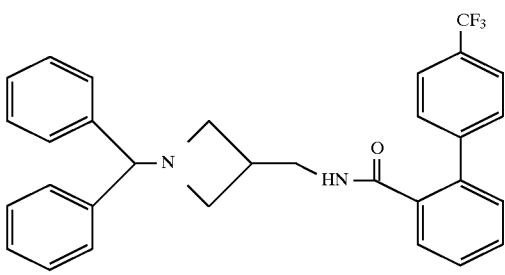
C.

Following the procedure in Example 1 Part D, Part B compound (500 mg, 1.98 mmol) was reacted with 4'-(trifluoromethyl)-2-biphenylcarboxylic acid (580 mg, 2.18 mmol) to give title compound (720 mg, 73%) as a white solid (m.p. 191°–195° C.).

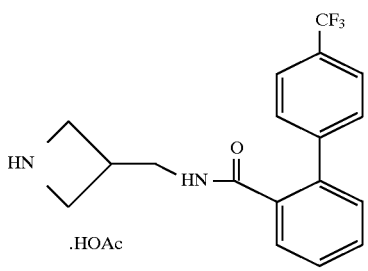
D.

Following the procedure in Example 1 Part E, Part C compound (280 mg, 1.44 mmol) was reacted to give title compound (220 mg, 46%) as an off-white solid which was carried on without purification.

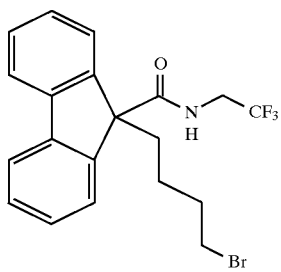
E.

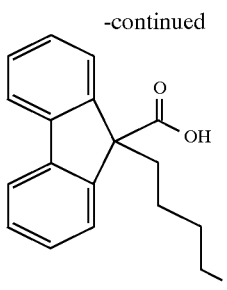
E(1).

To a solution of 9-fluorenecarboxylic acid (50 g, 240 mmol) in THF (1200 mL) at 0° C. was added dropwise a solution of n-butyllithium (2.5M, 211 mL, 530 mmol) in THF. The yellow reaction was stirred at 0° C. for 1 h, then 1,4-dibromobutane (31.3 mL, 260 mmol) was added dropwise over 30 min. The reaction was stirred at 0° C. for 30 min, then the reaction was warmed to RT for 30 h. The reaction was extracted with water (3×750 mL). The combined aqueous layers were extracted with ethyl ether (800 mL). The aqueous layer was made acidic with HCl solution (1N, 500 mL), then extracted with dichloromethane (3×750 mL). The combined organic layers were dried over MgSO$_4$. Evaporation gave title compound (71 g, 85%) as a white solid.

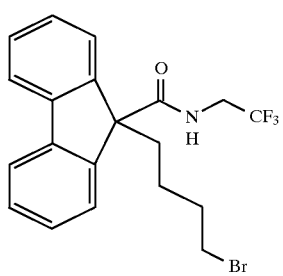
E(2).

To a solution of Part E(1) acid (60 g, 173 mmol) and DMF (100 μL) in CH$_2$Cl$_2$ (600 mL) under argon at 0° C. was added oxalyl chloride (104 mL, 2.0M in CH$_2$Cl$_2$, 208 mmol) dropwise. The reaction was stirred at 0° C. for 10 min, then warmed to RT and stirred for 1.5 h. The reaction was concentrated in vacuo to give the crude acid chloride as a yellow oil. To a suspension of 2,2,2-trifluoroethylamine hydrochloride (25.9 g, 191 mmol) in CH$_2$Cl$_2$ (500 mL) at 0° C. under argon was added triethylamine (73 mL, 521 mmol) followed by dropwise addition of a solution of the crude acid chloride in CH$_2$Cl$_2$ (15 mL). The reaction was stirred at 0° C. for 1 h, diluted with CH$_2$Cl$_2$ (500 mL), and washed with water (2×300 mL), 1N HCl (2×300 mL), saturated NaHCO$_3$ (2×300 mL), and brine (2×300 mL), then dried over MgSO$_4$. Evaporation gave 80 g of a oil which was purified by flash chromatography on silica gel (2.5 kg). The crude product was loaded in a mixture of CH$_2$Cl$_2$ and hexane, and eluted with a step gradient of 10% EtOAc/hexane (4L) to 15% EtOAc/hexane (2L) to 20% EtOAc/hexane (4L). Pure fractions were combined and evaporated to give title compound (52.5 g, 71%) as a white solid (mp 88°–92° C.).

F. N-(2,2,2-Trifluoroethyl)-9-[4-[3-[[[[4'-(trifluoromethyl)[1,1'-biphenyl]-3-yl]-carbonyl]amino]methyl]-1-azetidinyl]butyl]-9H-fluorene-9-carboxamide, monohydrochloride Following the procedure in Example 1 Part D compound (220 mg, 0.32 mmol) was reacted with Part E compound (138 mg, 0.32 mmol) to give title compound (205 mg, 36%) as a white solid (m.p. 79°–83° C.).

MS (ES, +ions): m/z 680 (M+H).

Anal. Calcd for $C_{38}H_{35}F_6N_3O_2$+2.0 HCl+2.0 $H_2O$: C, 58.54; H, 5.17; N, 5.39; Cl, 9.09 Found: C, 58.61; H, 5.03; N, 5.29; Cl, 9.10.

EXAMPLE 4

9-[4-[3-[(Benzoylamino)methyl]-1-azetidinyl]butyl]-N-(2,2,2-trifluoroethyl)-9H-fluorene-9-carboxamide, monohydrochloride

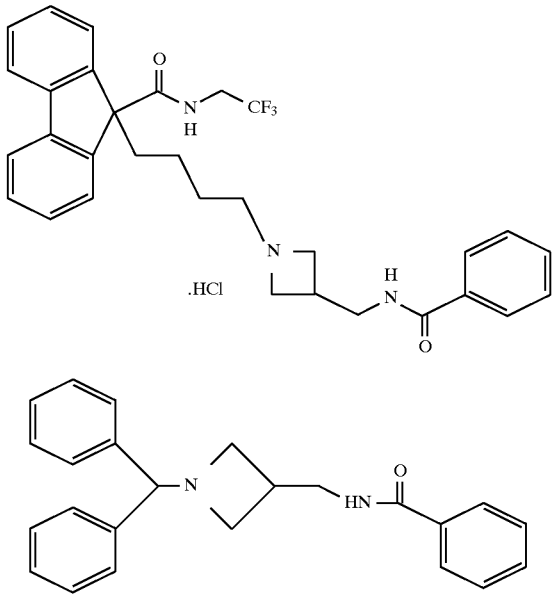

To a solution of Example 3 Part B compound (500 mg, 1.98 mmol), triethylamine 0.4 mL, 2.97 mmol) in dichloromethane (10 mL) at 0° C. was added dropwise a solution of benzoyl chloride in dichloromethane (1 mL). The reaction was stirred at 0° C. for 10 min. Ethyl acetate (50 mL) was added abd the solution was washed with water (2×30 mL), brine (2×30 mL) and dried over $MgSO_4$. Evaporation gave a yellow oil. Purification was performed by flash chromatography on silica gel, loaded and eluted with 2% methanol in dichloromethane. Pure fractions were combined and evaporated to give title compound (420 mg, 62%) as a colorless oil.

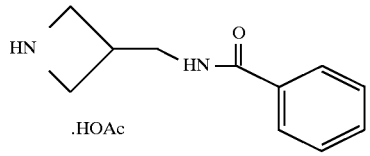

Following the procedure in Example 1 Part E, Part A compound (420 mg, 1.19 mmol) was reacted to give title compound (200 mg, 88%) as a colorless oil which was carried on without purification.

C. 9-[4-[3-[(Benzoylamino)methyl]-1-azetidinyl]butyl]-N-(2,2,2-trifluoroethyl)-9H-fluorene-9-carboxamide, monohydrochloride Following the procedure in Example 1 Part G, Part B compound (161 mg, 0.85 mmol) was reacted with Example 3 Part E compound (361 mg, 0.85 mmol) to give title compound (150 mg, 28%) as a white solid (m.p. 91°–96° C.).

MS (ES, +ions): m/z 536 (M+H).

Anal. Calcd for $C_{31}H_{33}F_3N_3O_2$+HCl+2.4 $H_2O$: C, 60.69; H, 6.18; N, 6.85 Found: C, 61.09; H, 5.91; N, 6.35.

EXAMPLE 5

N-(2,2,2-Trifluoroethyl)-9-[4-[3-[[[4'-(trifluoromethyl)[1,1'-biphenyl]-2-yl]carbonyl]amino]-1-azetidinyl]butyl]-9H-fluorene-9-carboxamide, monohydrochloride

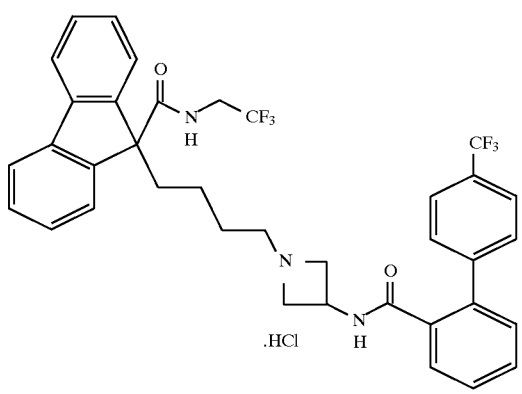

Following the procedure in Example 1, Example 3 Part E compound was substituted for Example 1 Part F compound to give title compound as a white solid.

m.p. 93°–96° C. MS (ES, +ions): m/z 666 (M+H).

EXAMPLE 6

9-[4-[3-(Benzoylamino)-1-azetidinyl]butyl]-N-(2,2,2-trifluoroethyl)-9H-fluorene-9-carboxamide, monohydrochloride

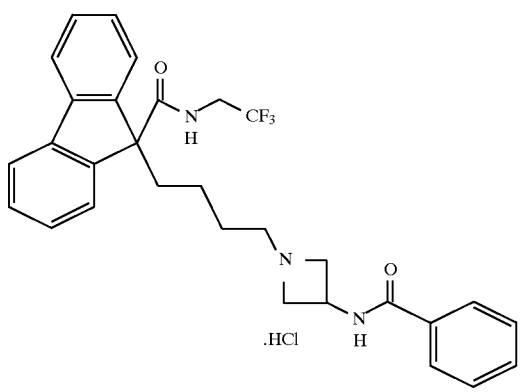

Following the procedure in Example 5 except substituting benzoic acid for 4'-(trifluoromethyl)-2-biphenylcarboxylic acid, title compound was prepared as a white solid.

m.p. 91°–95° C. MS (ES, +ions): m/z 522 (M+H).

Anal. Calcd for $C_{30}H_{30}F_3N_3O_2$+1.4 HCl+1.5 $H_2O$: C, 60.09; H, 5.78; N, 7.01; F, 9.50; Cl, 8.28 Found: C, 60.15; H, 5.59; N, 7.18; F, 9.13; Cl, 8.67.

Example 7

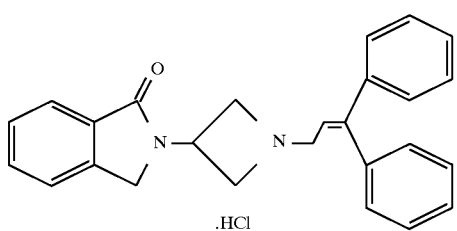

-continued
Example 8A:
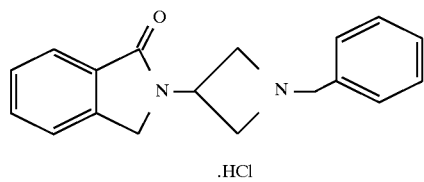
.HCl
Example 8B:
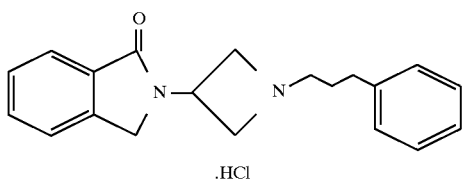
.HCl
Example 8C:
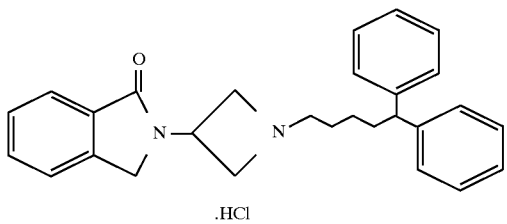
.HCl
Example 8D:
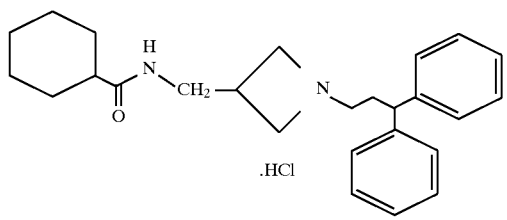
.HCl
Example 9:
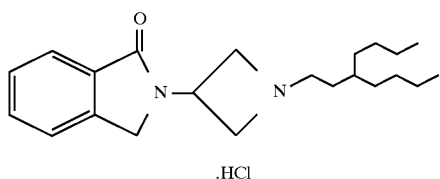
.HCl
Example 10:
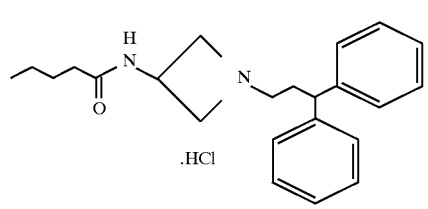
.HCl
-continued
Example 11:
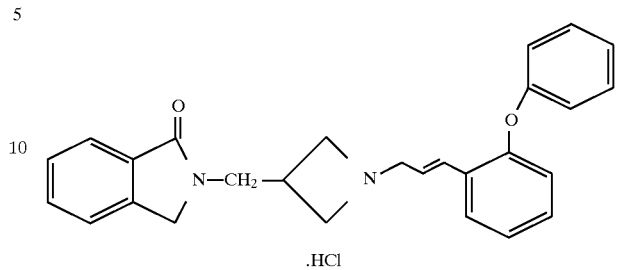
.HCl
Example 12:
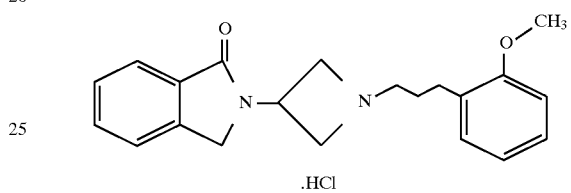
.HCl
Example 13:
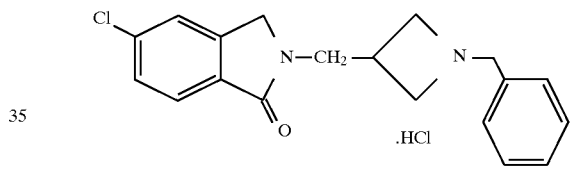
.HCl
Example 14:
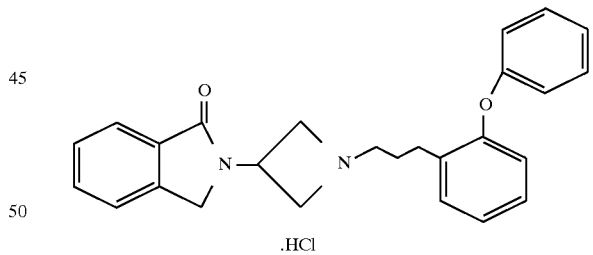
.HCl
Example 15:
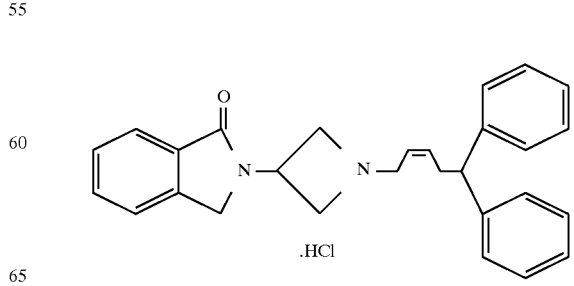
.HCl -continued
Example 16:

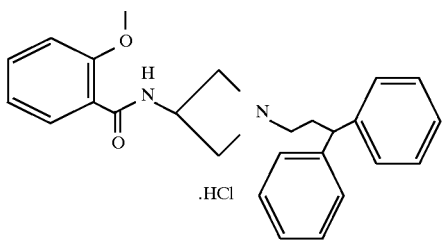
.HCl

Example 17:

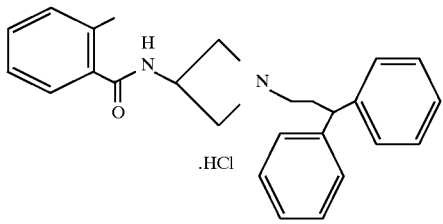
.HCl

Example 18:

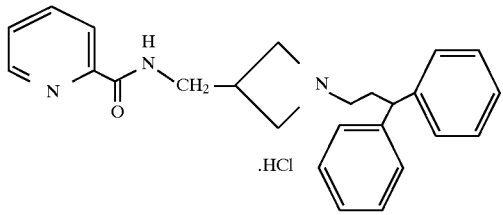
.HCl

Example 19:

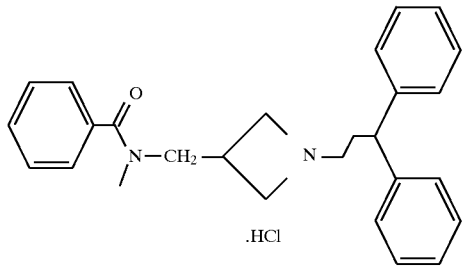
.HCl

EXAMPLES 20 to 202

TABLE A

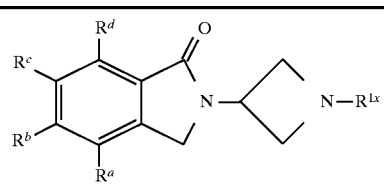

where $R^{1x}$ is (a) 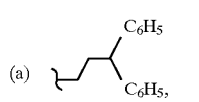    b) 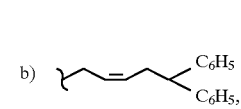

TABLE A-continued (c) -fluorenyl with butyl chain), ($R^e = C_3H_7$ or $CF_3CH_2$)

(d) ![butylsulfonyl fluorenyl structure]    or   (e) ![Rᵉ-NH-C(=O)-fluorenyl with allyl chain structure]

| $R^a$ | $R^b$ | $R^c$ | $R_d$ |
|---|---|---|---|
| H | H | H | F |
| H | H | H | -O-propyl |
| H | H | F | Cl |
| H | H | $CF_3$ | H |
| H | $OCH_3$ | H | H |
| H | H | H | $-OCH_2$-phenyl |
| $-OCH_2$-phenyl | H | H | H |
| H | H | phenyl | H |
| F | Cl | H | H |
| H | H | H | -S-phenyl |
| H | H | H | -C$_6$H$_4$-$CF_3$ |
| -C$_6$H$_4$-$CF_3$ | H | H | H |
| H | H | Cl | H |
| H | H | H | -C$_6$H$_4$-Cl |
| H | H | H | H |
| H | H | H | Cl |
| H | H | $CH_3$ | H |
| H | $CH3$ | H | thienyl |
| $SCH_3$ | H | H | H |
| H | H | $OCH_3$ | H |
| H | H | H | $SCH_3$ |
| H | H | H | H |
| H | H | H | $-CH_2-\!\!\equiv\!\!-H$ |
| H | cyclopropyl | H | H |
| H | H | H | $-CH_2-$cyclopropyl |

Example 203
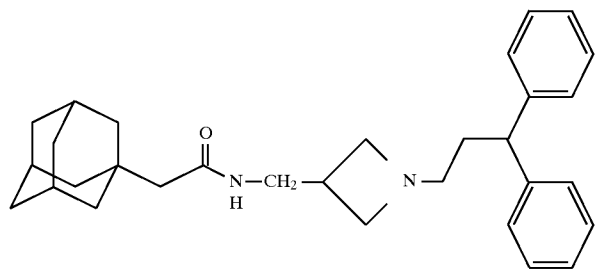
Example 204
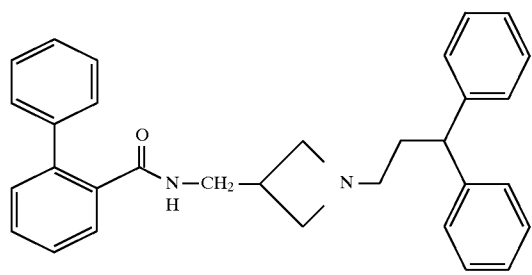
Example 205
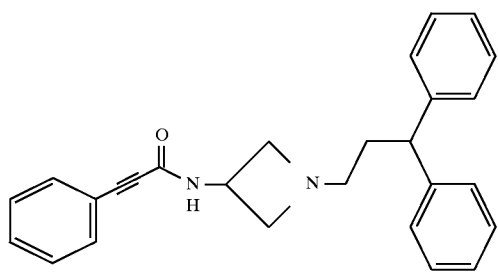
Example 206
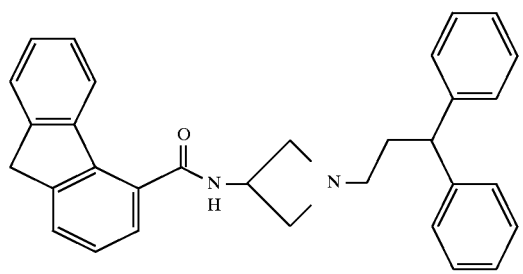

-continued
Example 207
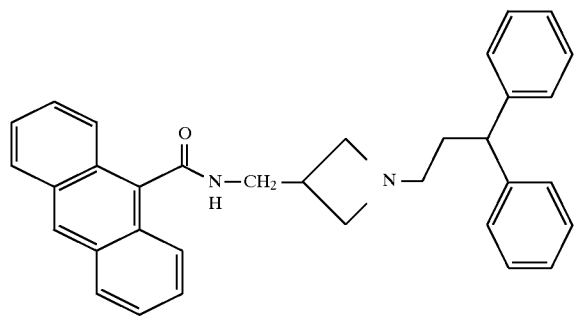
Example 208
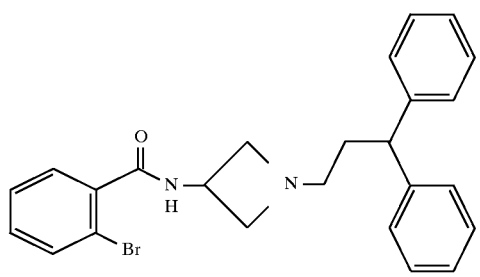
Example 209
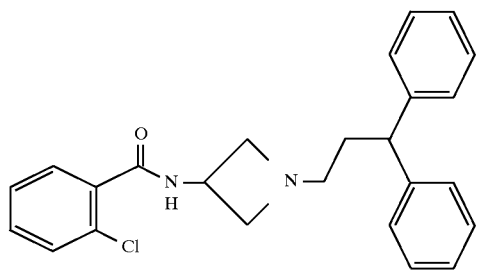
Example 210
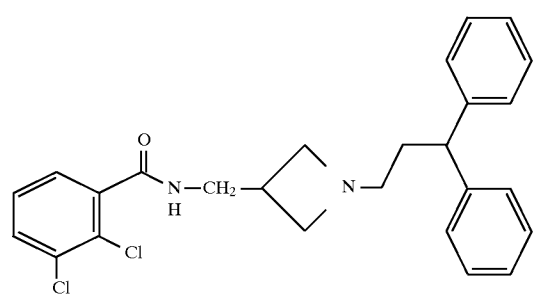
Example 211
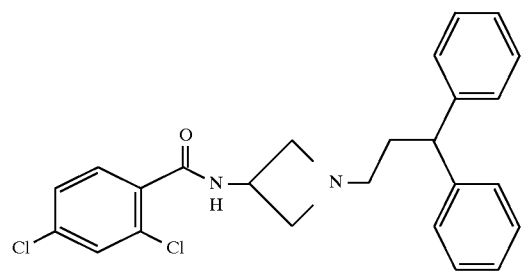

-continued
Example 212
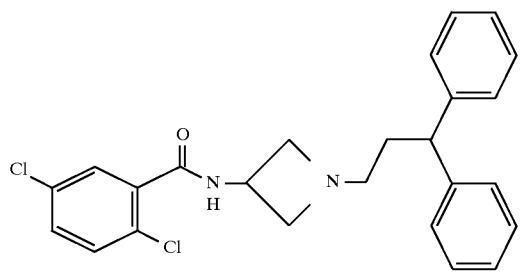
Example 213
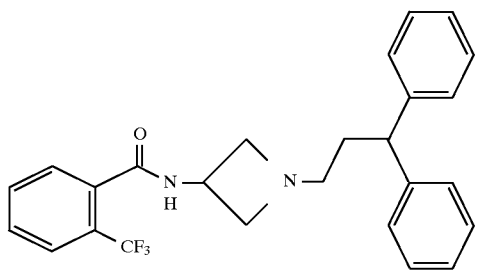
Example 214
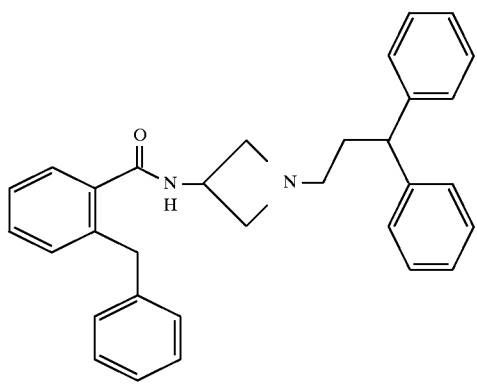
Example 215
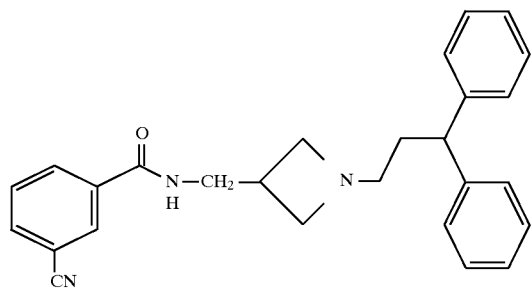

-continued
Example 216
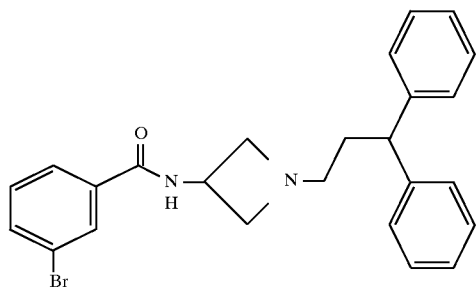
Example 217
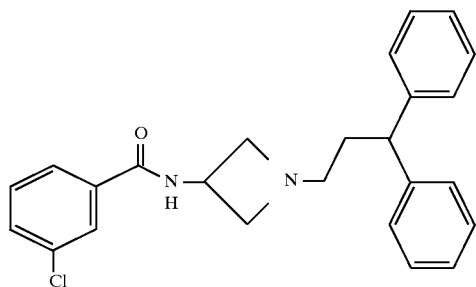
Example 218
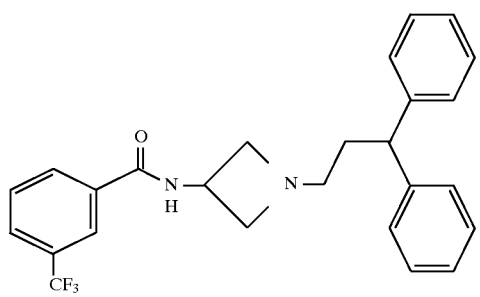
Example 219
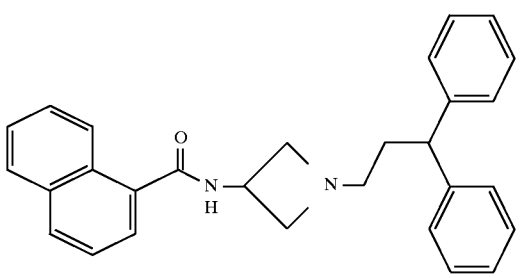
Example 220:
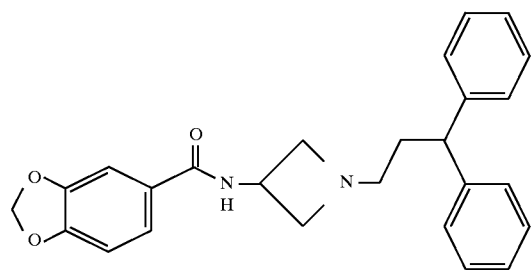

-continued
Example 221:
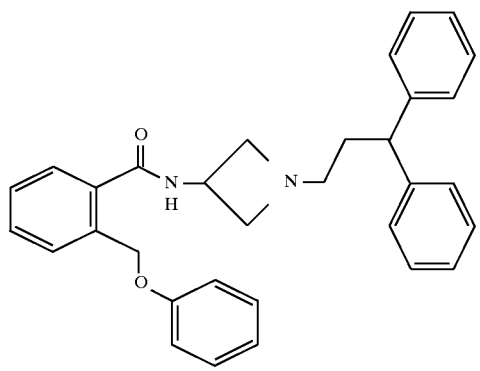
Example 222:
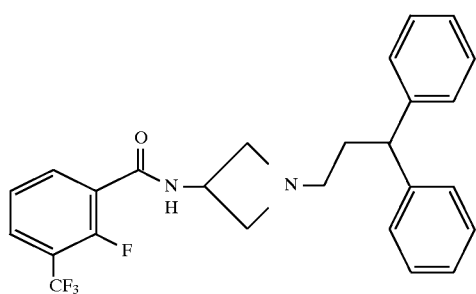
Example 223:
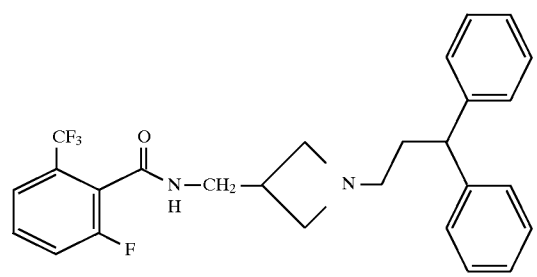
Example 224:
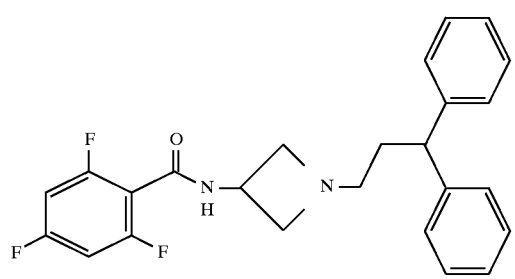

-continued
Example 225:
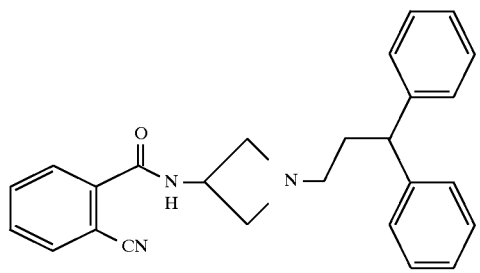
Example 226:
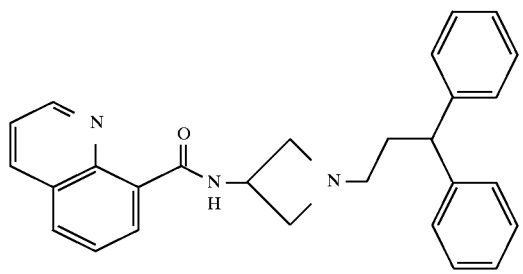
Example 227:
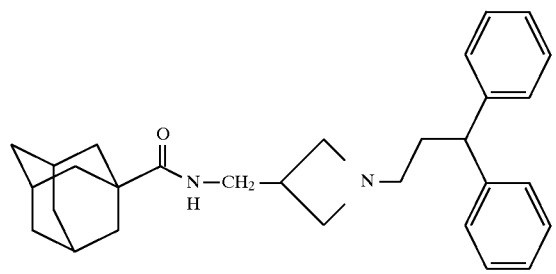
Example 228:
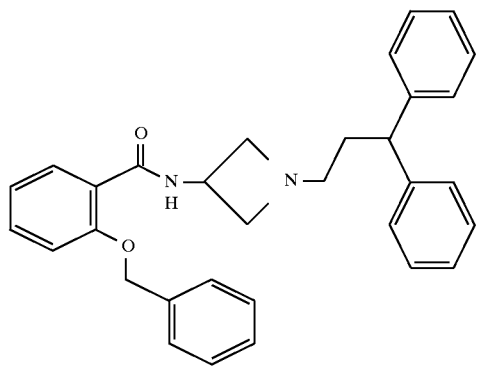
Example 229:
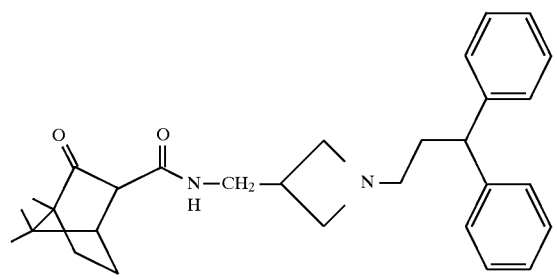

Example 230:
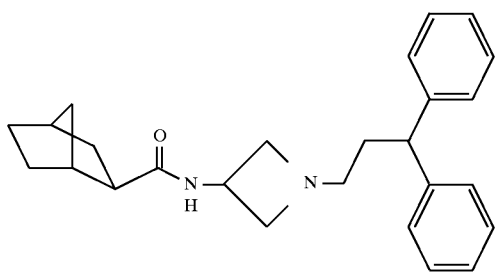
Example 231:
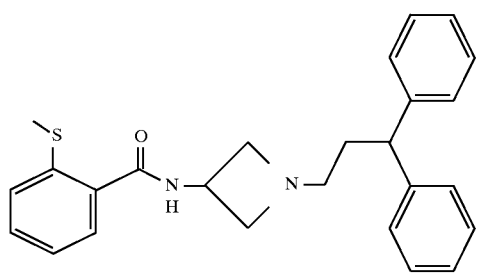
Example 232:
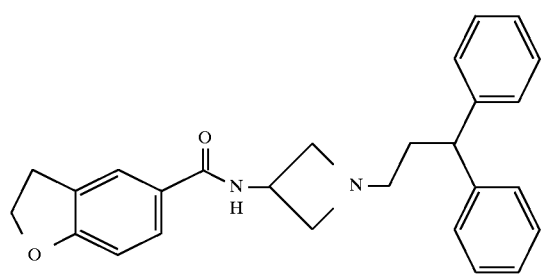
Example 233:
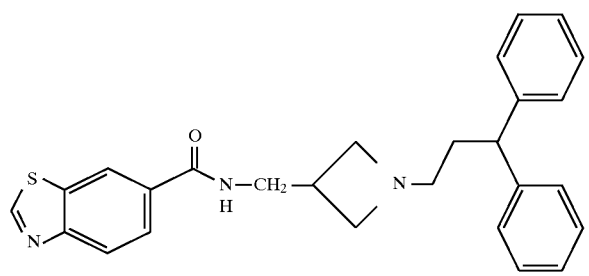
Example 234:
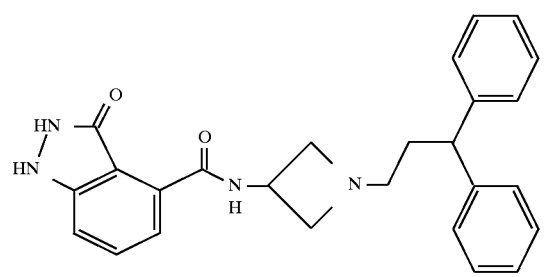

-continued
Example 235:
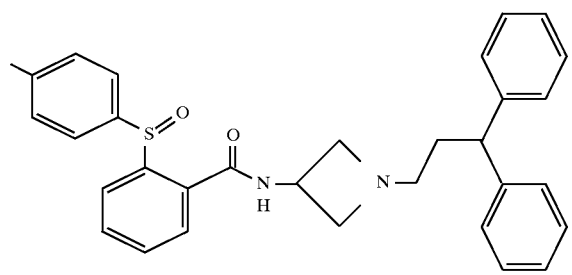
Example 236:
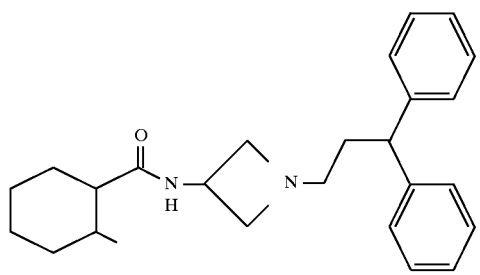
Example 237
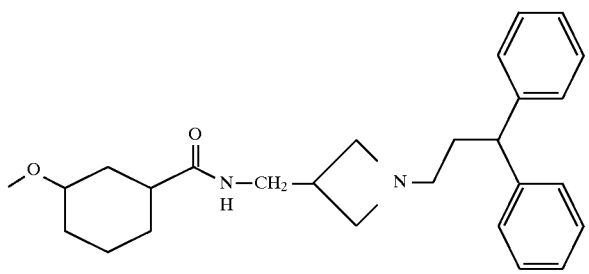
Example 238:
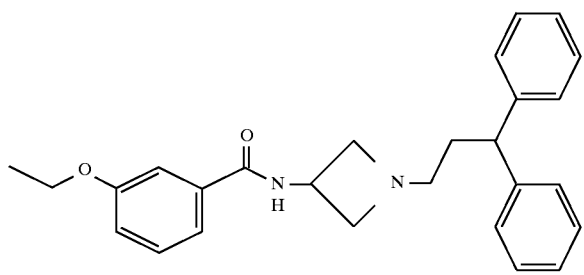
Example 239:
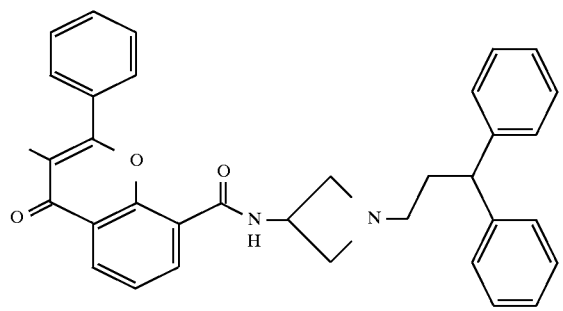

-continued
Example 240:
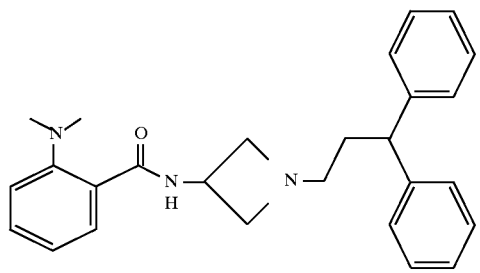
Example 241:
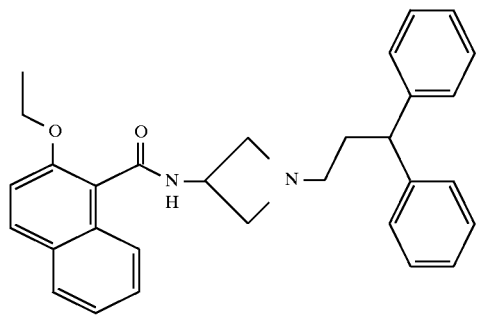
Example 242:
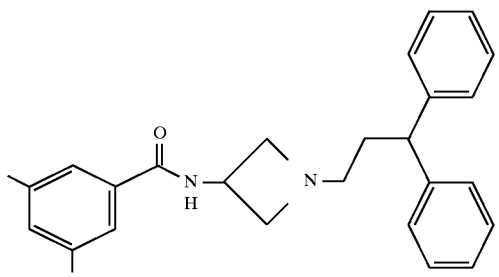
Example 243:
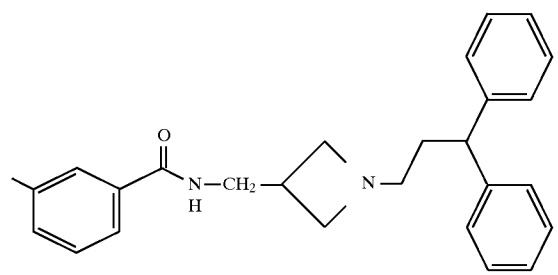
Example 244:
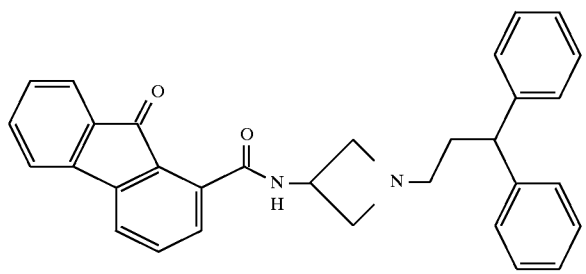

-continued
Example 245:
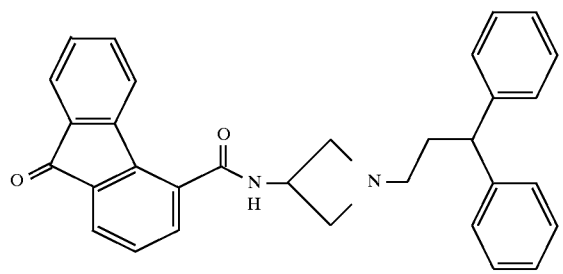
Example 246:
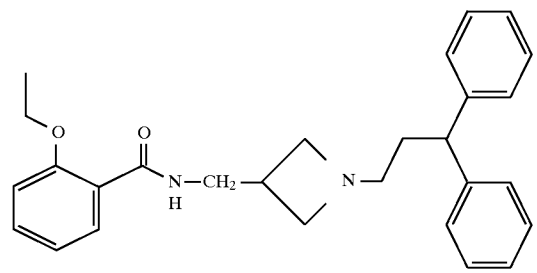
Example 247:
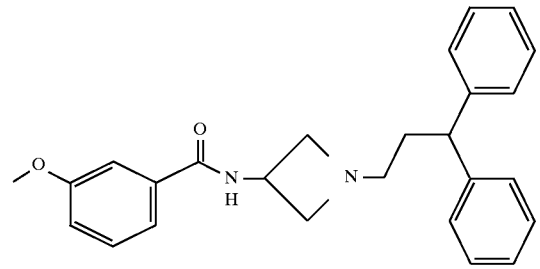
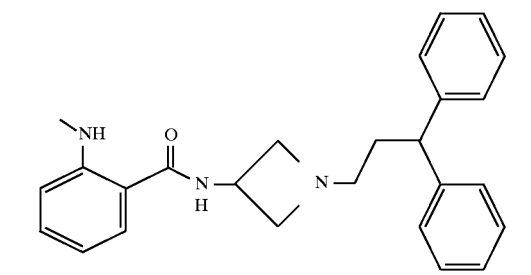
Example 249:
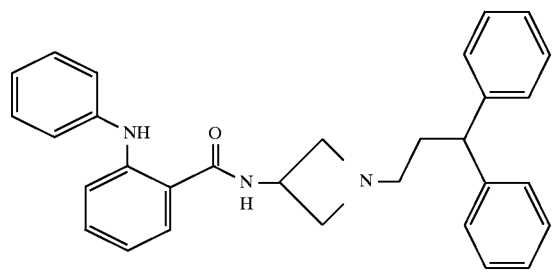

-continued
Example 250:
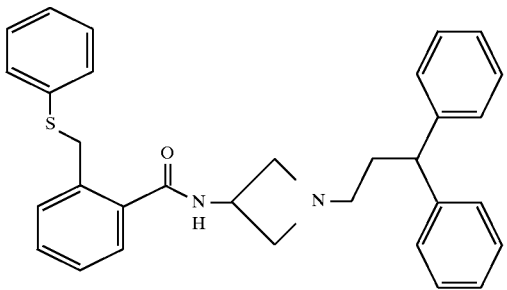
Example 251:
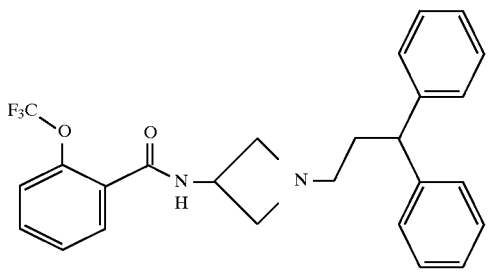
Example 252:
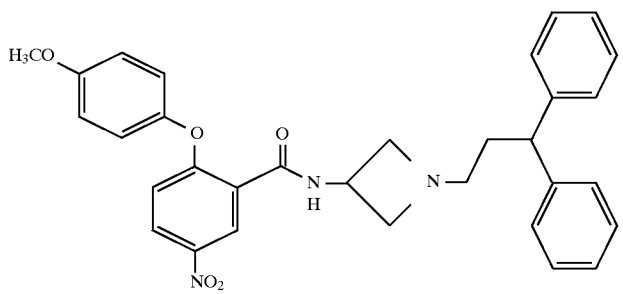
Example 253:
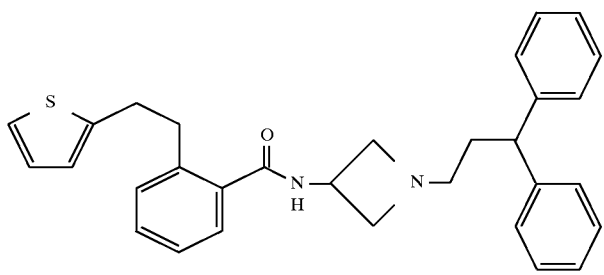
Example 254:
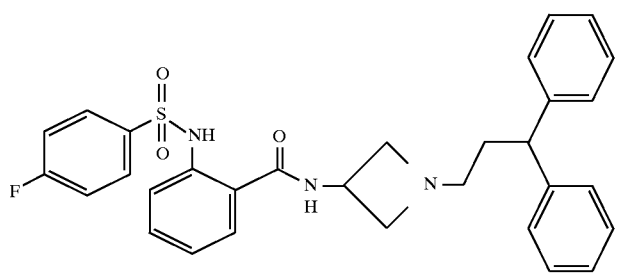

-continued
Example 255:
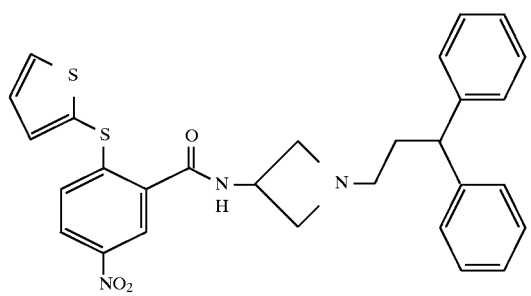
Example 256:
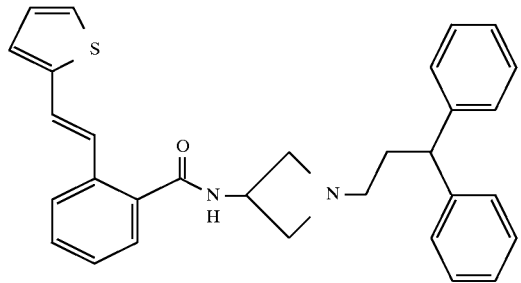
Example 257:
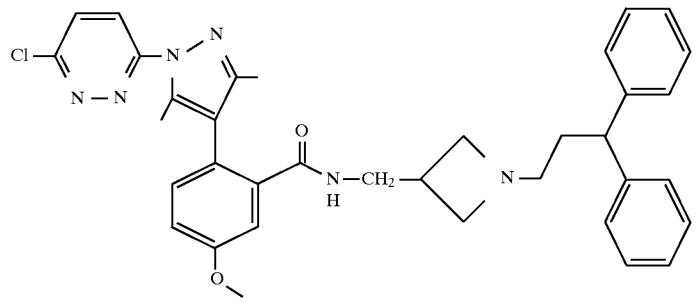
Example 258:
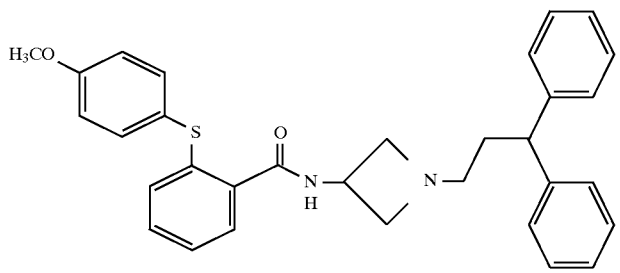

-continued
Example 259:
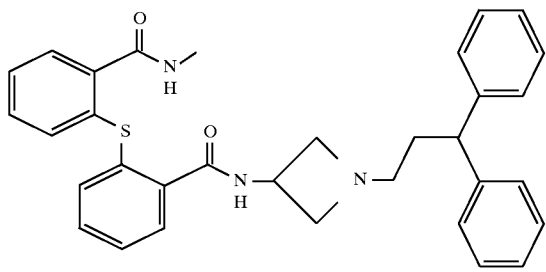
Example 260:
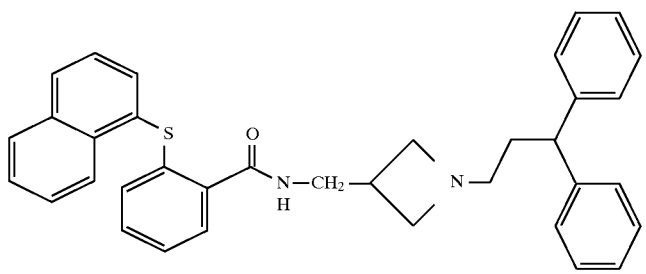
Example 261:
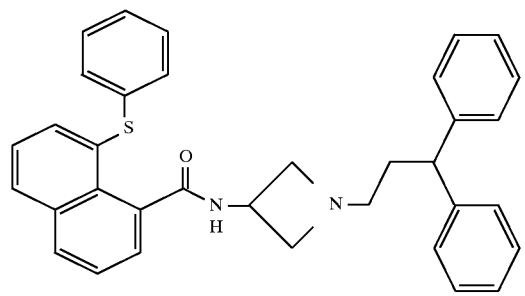
Example 262:
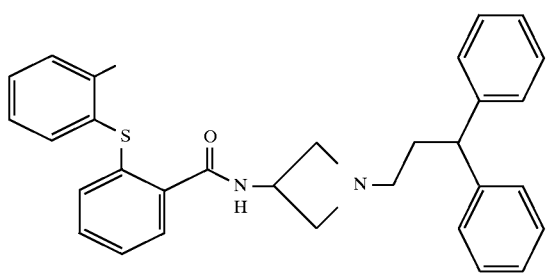
Example 263:
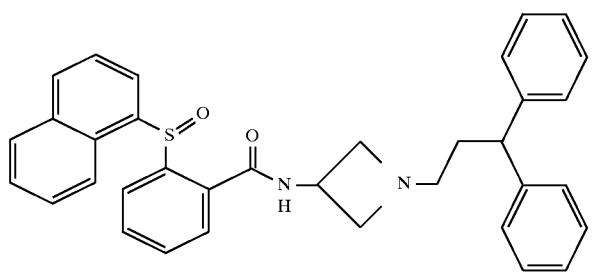

-continued
Example 264:
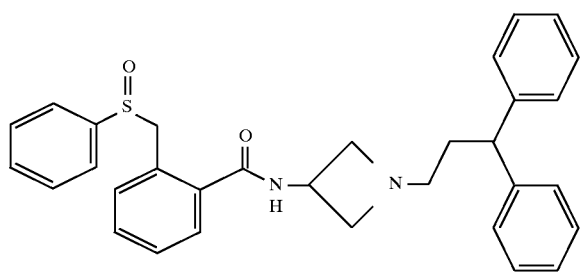
Example 265:
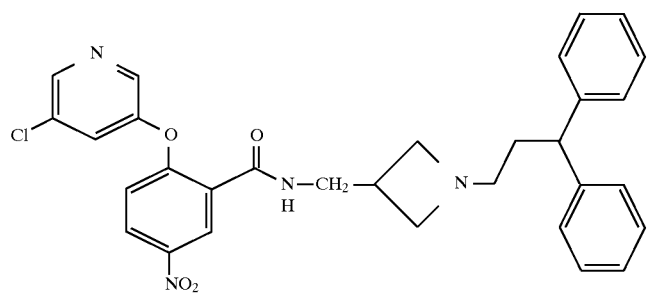
Example 266:
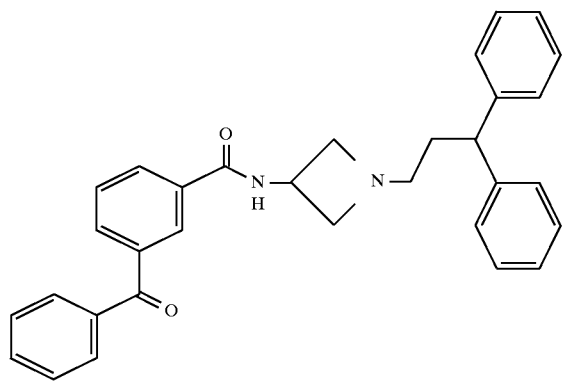
Example 267:
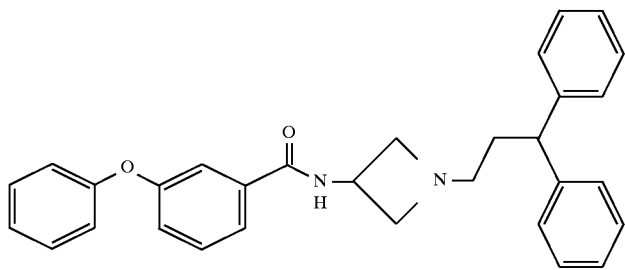

-continued
Example 268:
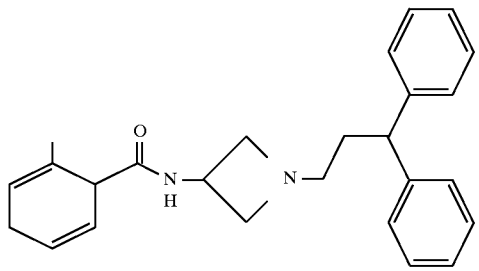
Example 269:
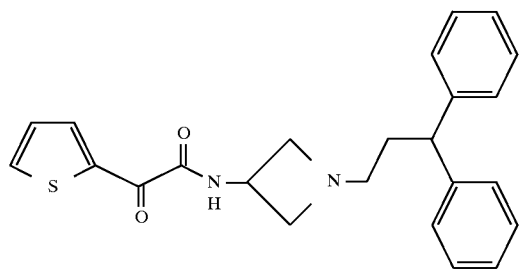
Example 270:
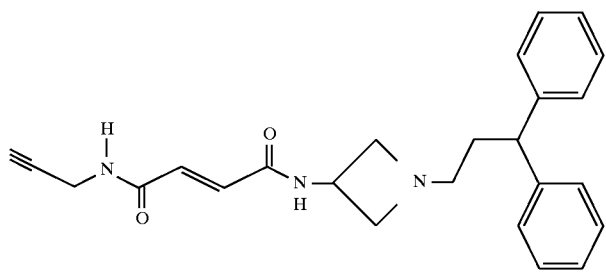
Example 271:
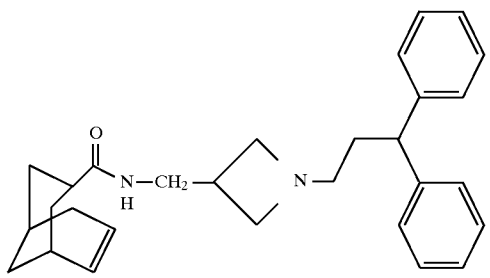
Example 272:
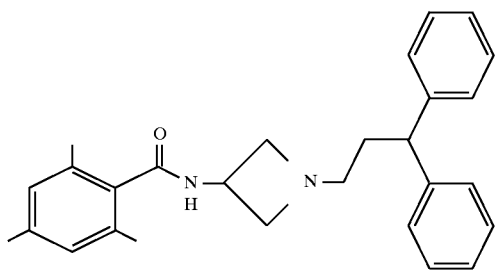

-continued
Example 273:
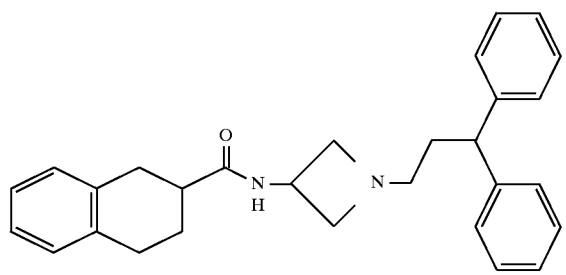
Example 274:
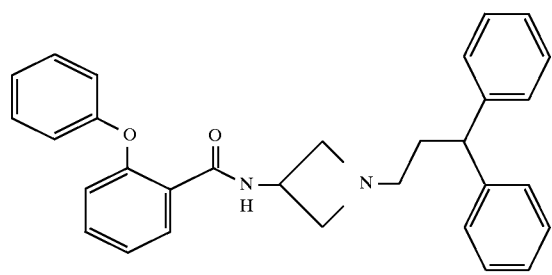
Example 275:
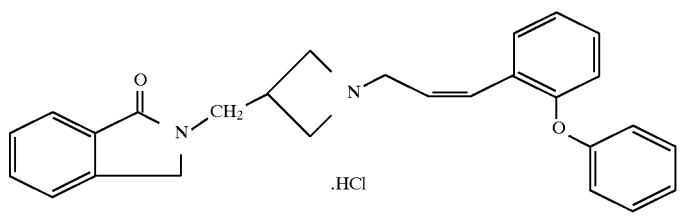
.HCl
Example 276:
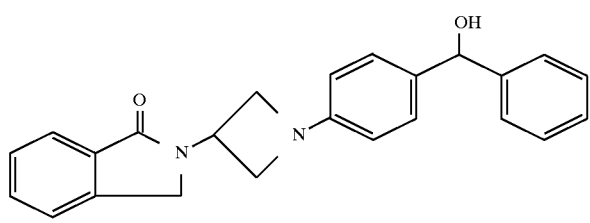
Example 277:
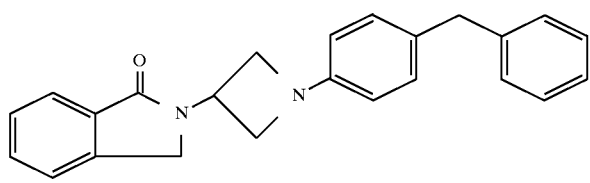
Example 278:
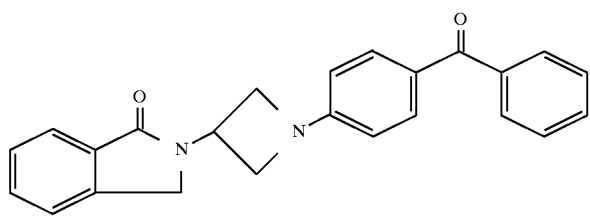

-continued
Example 279:
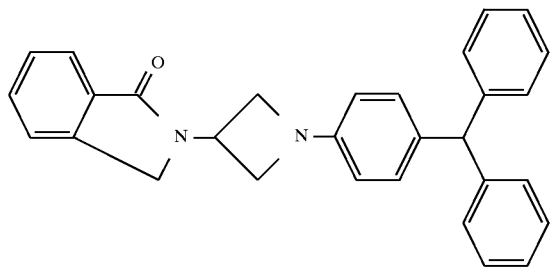
Example 280:
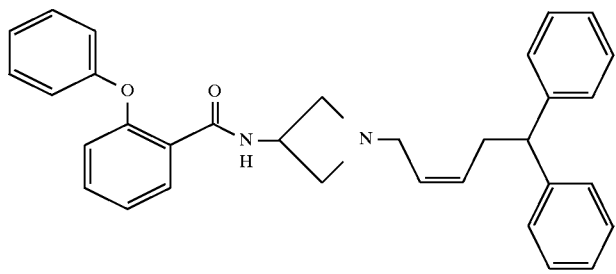
Example 281:
(Z)-N-[1-(5,5-Diphenyl-2-pentenyl)-2-azetidinyl]-2-phenoxybenzamide
Example 282:
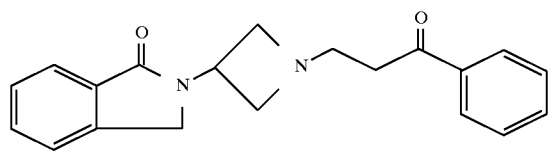
Example 283:
2,3-Dihydro-2-[1-[3-phenyl-3-(4-propylphenyl)-propyl]-2-azetidinyl]-1H-isoindol-1-one, monohydrochloride
Example 284:
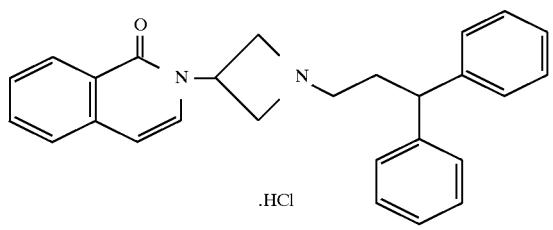
.HCl
Example 285:
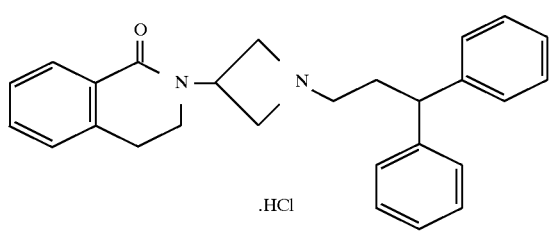
.HCl -continued
Example 286:
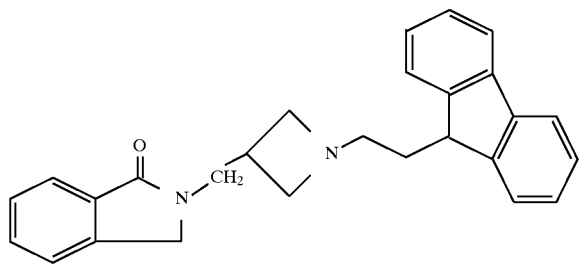
Example 287:
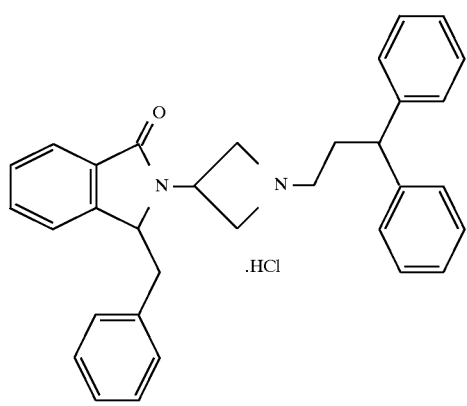
Example 288:
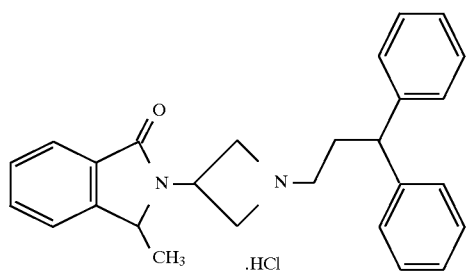
Example 289:
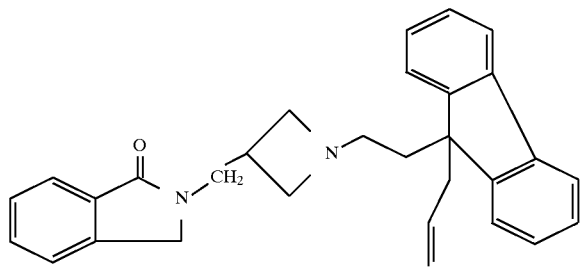

-continued
Example 290:
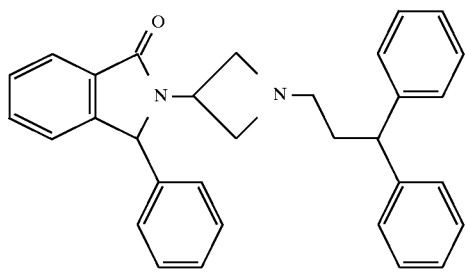
Example 291:
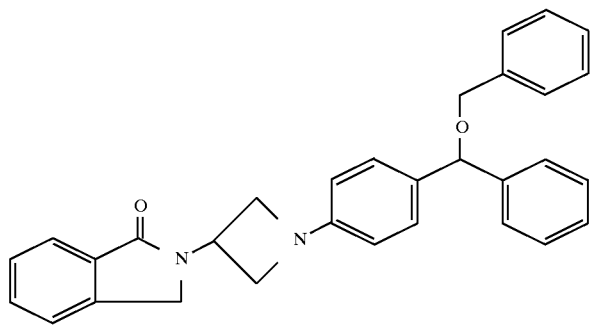
Example 292:
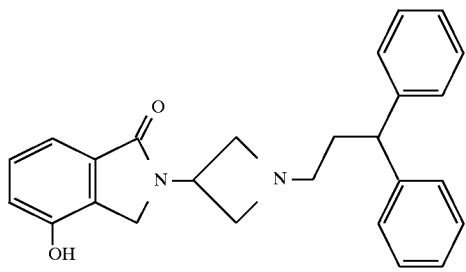
Example 293:
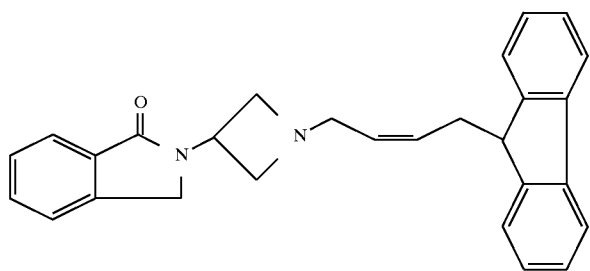
Example 294:
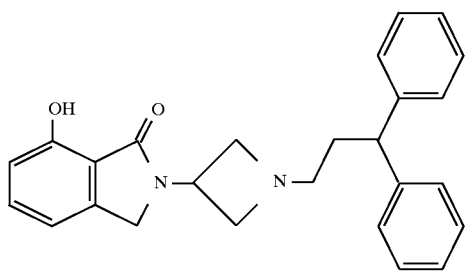

-continued
Example 295:
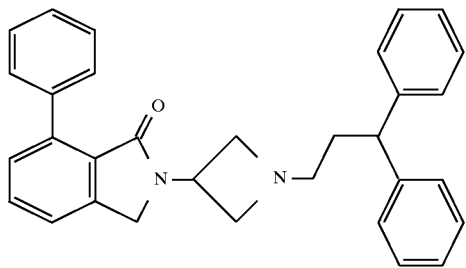
Example 296:
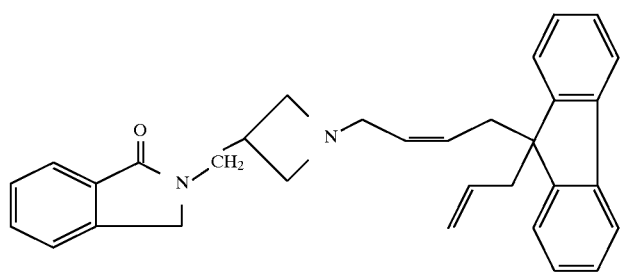
Example 297:
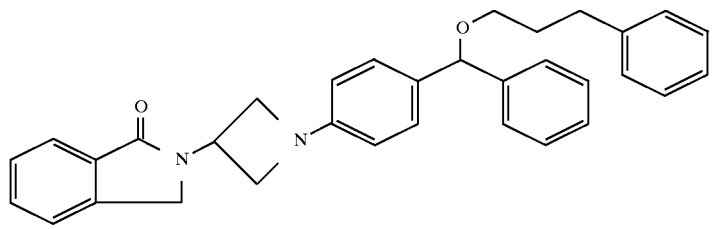
Example 298:
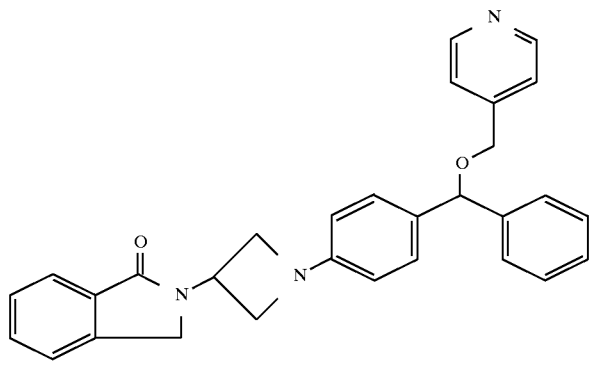

-continued
Example 299:
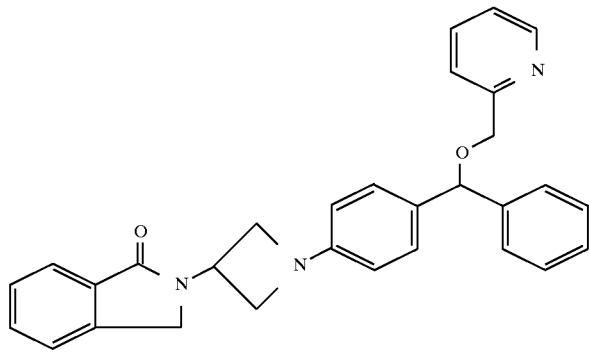
Example 300:
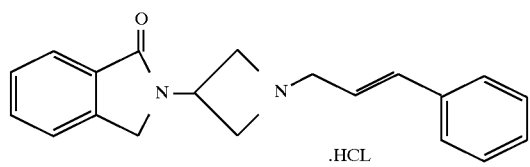
Example 301:
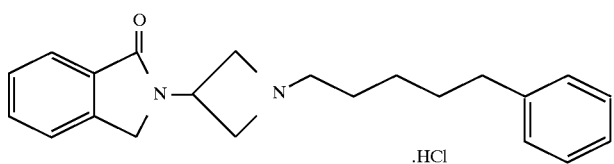
Example 302:
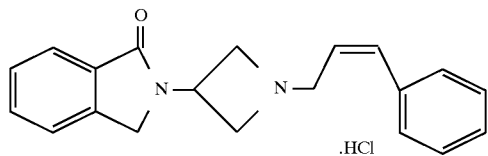
Example 303:
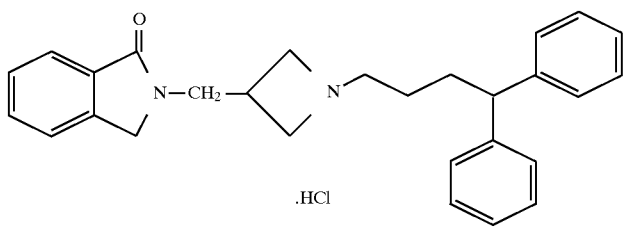
Example 304:
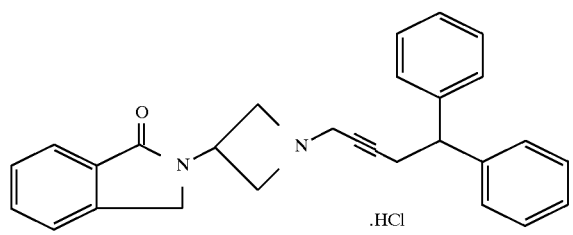

-continued
Example 305:
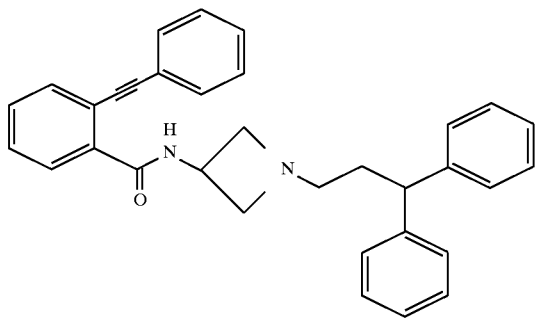
Example 306:
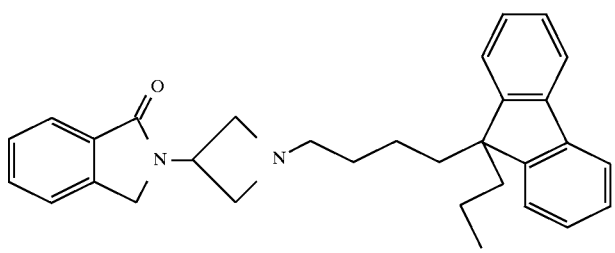
Example 307:
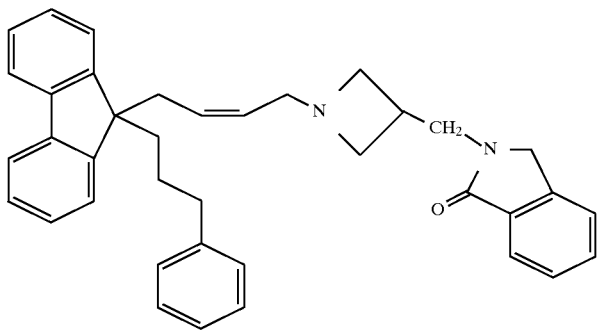
Example 308:
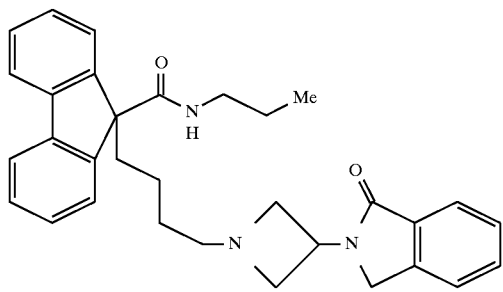

-continued
Example 309:
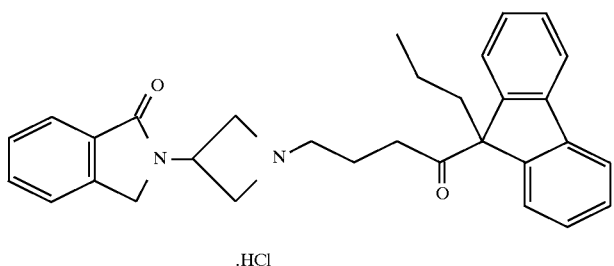
.HCl
Example 310:
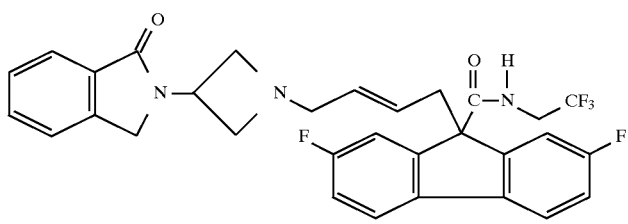
Example 311:
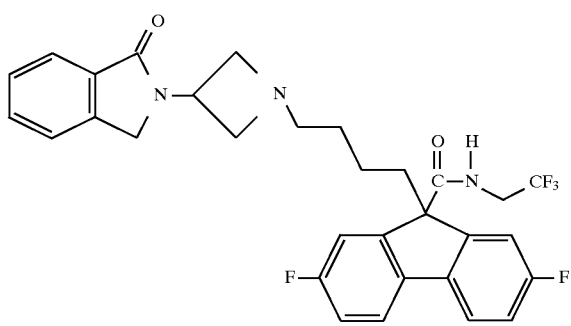
Example 312:
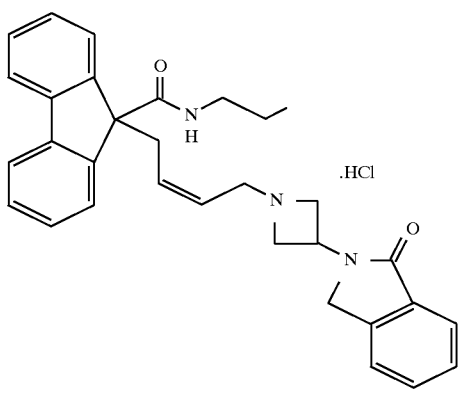
Example 313:
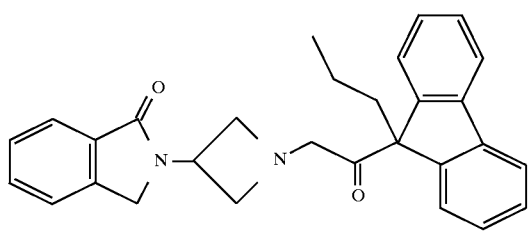

-continued
Example 314:
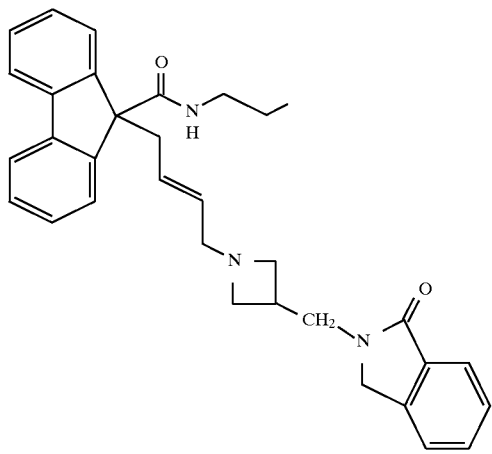
Example 315:
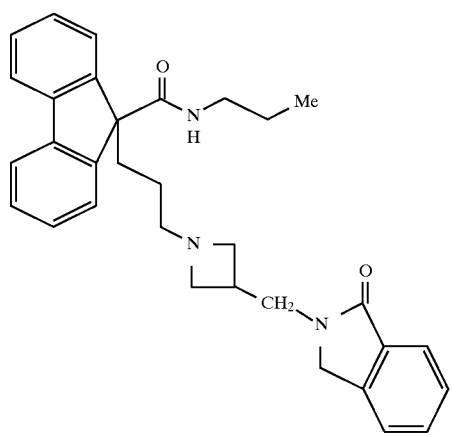
Example 316:
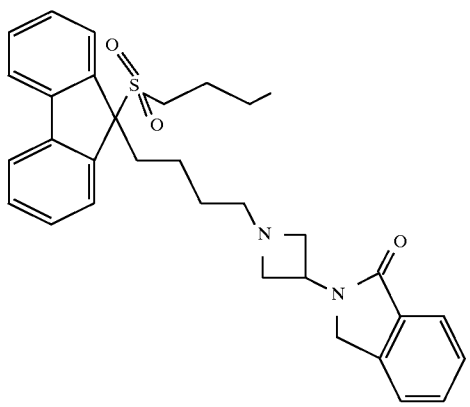

-continued
Example 317:
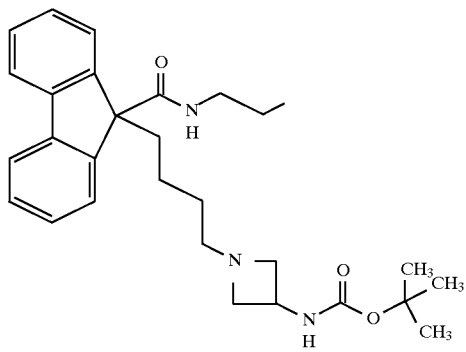
Example 318:
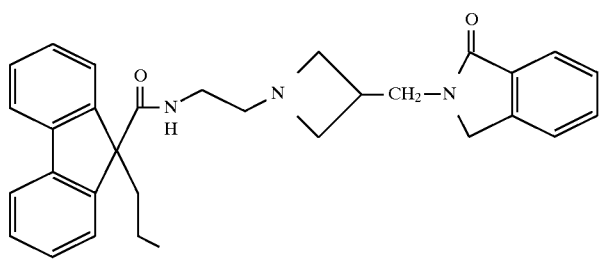
Example 319:
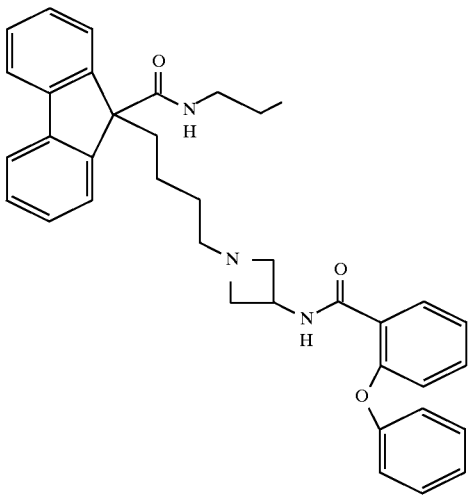

-continued
Example 320:
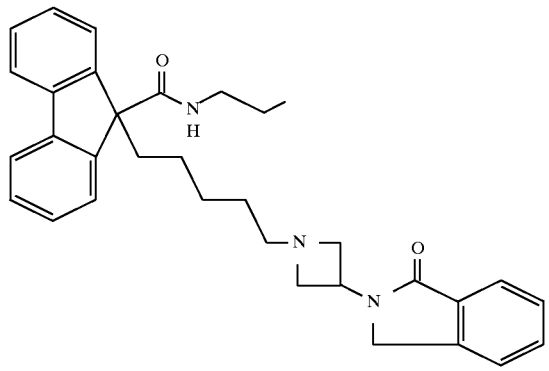
Example 321:
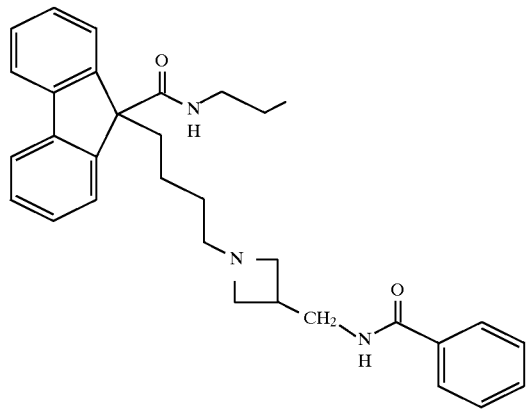
Example 322:
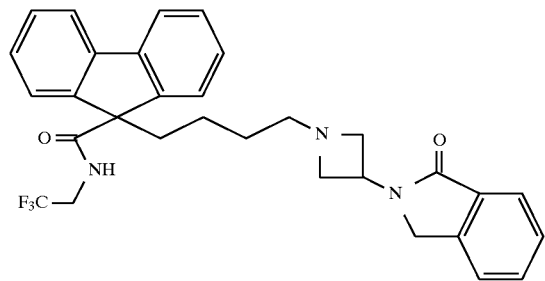
Example 323:
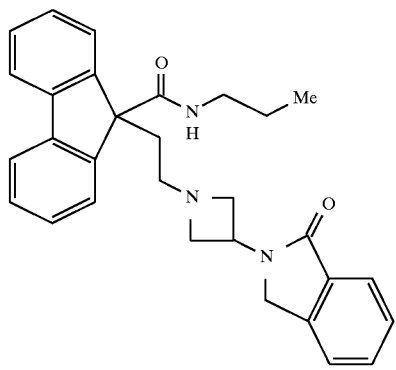

-continued
Example 324:
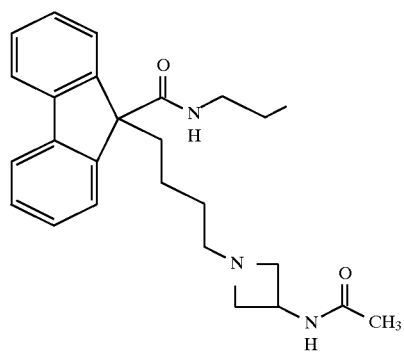
Example 325:
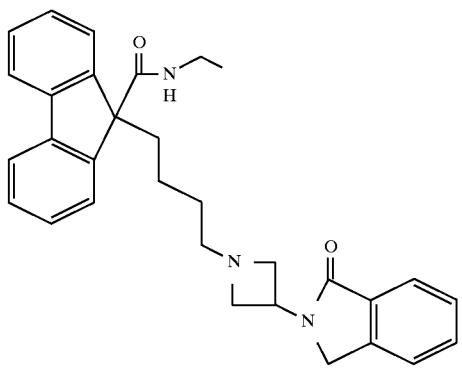
Example 326:
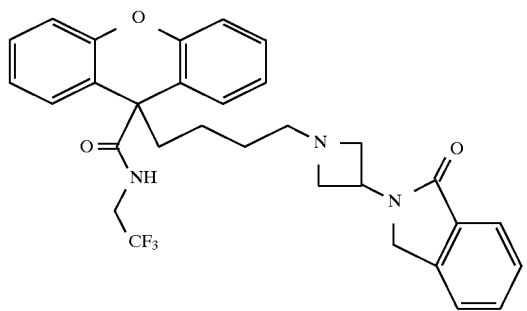
Example 327:
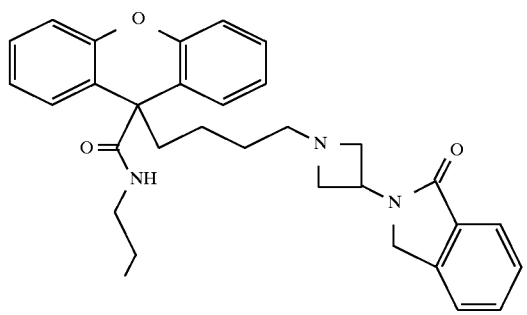

-continued
Example 328:
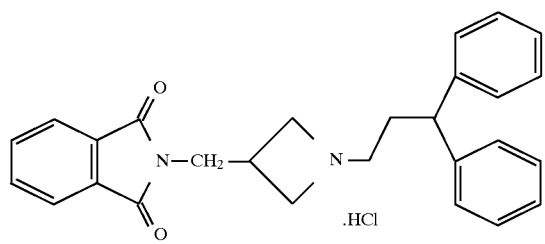
Example 329:
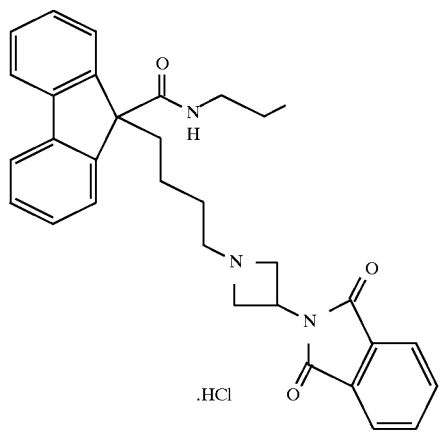
Example 330:
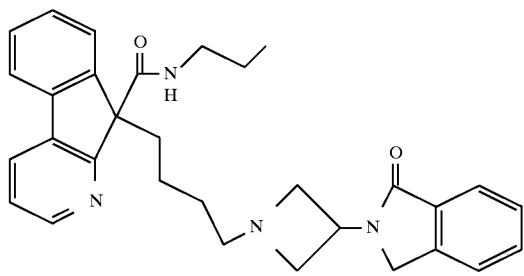
Example 331:
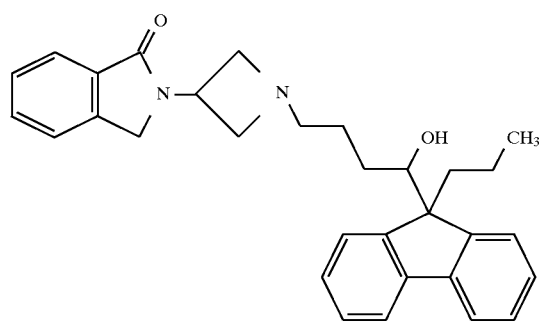

Example 332:
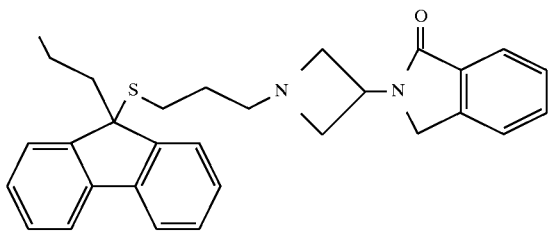
Example 333:
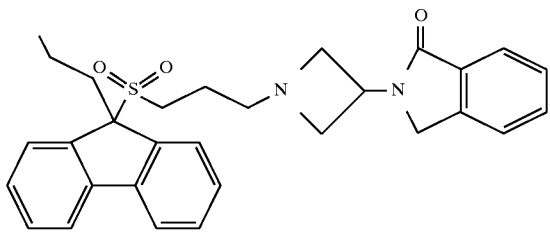
Example 334:
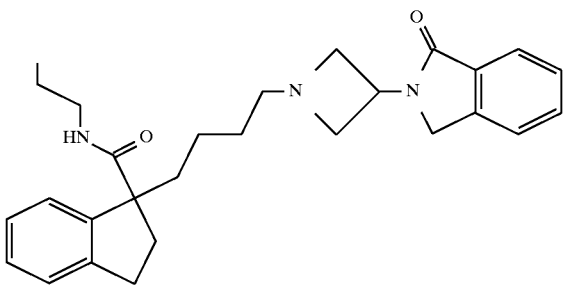
Example 335:
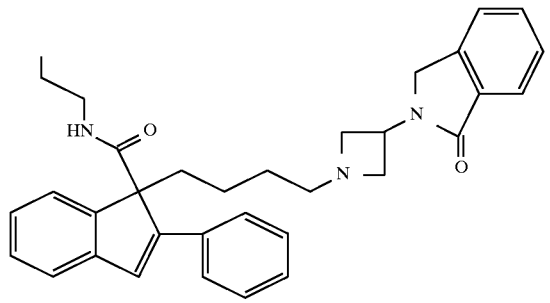
Example 336:
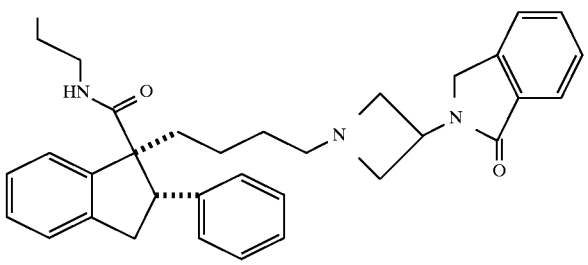
Additional compounds falling within the scope of the present invention are described by the following structures. Substituents for each example are identified in the table following each structure.

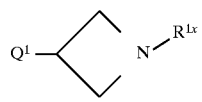
where R¹ˣ is (a), (b), (c), (d) or (e) as in Table A
Examples of Q¹
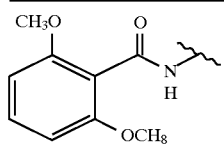 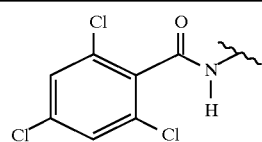 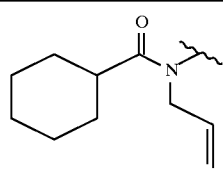
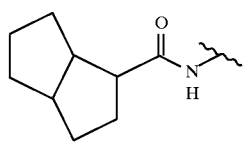 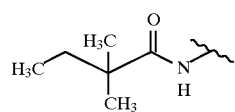 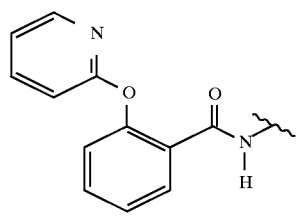
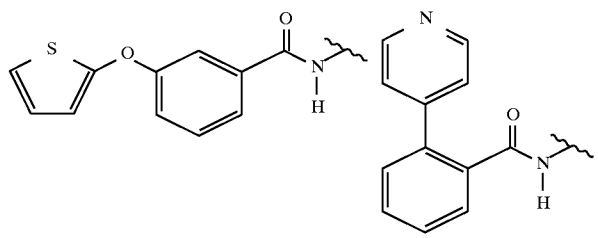 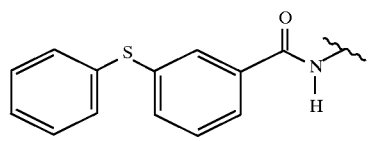
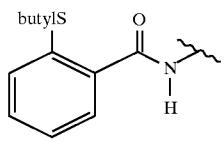 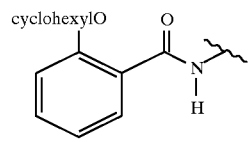 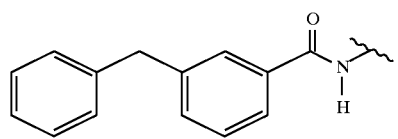
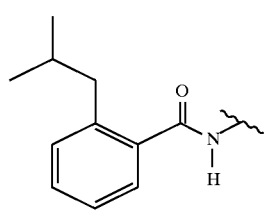 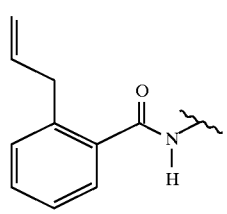 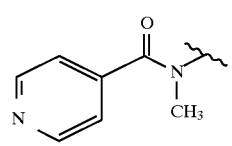
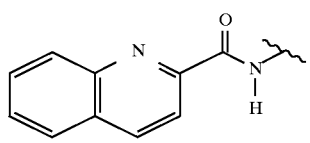 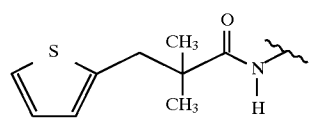 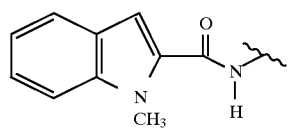

-continued
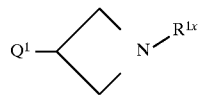
where $R^{1x}$ is (a), (b), (c), (d) or (e) as in Table A
Examples of $Q^1$
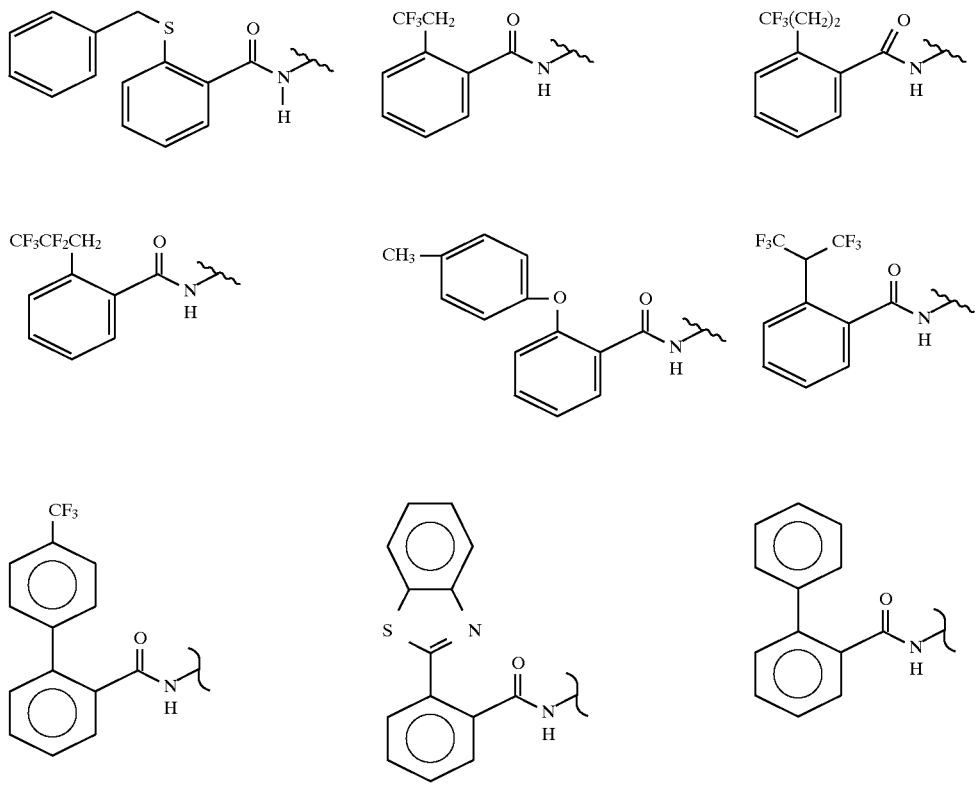

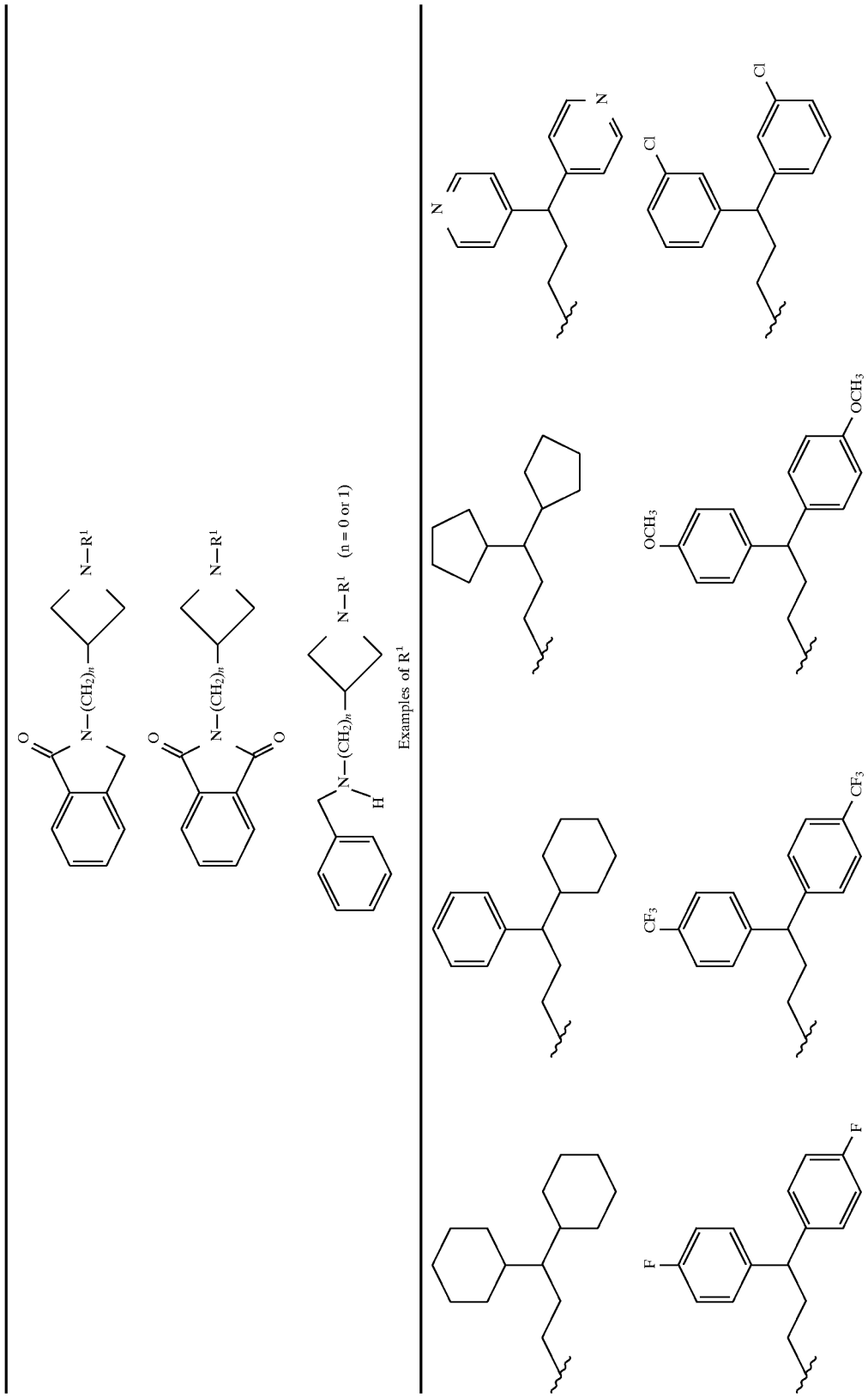

TABLE C-continued
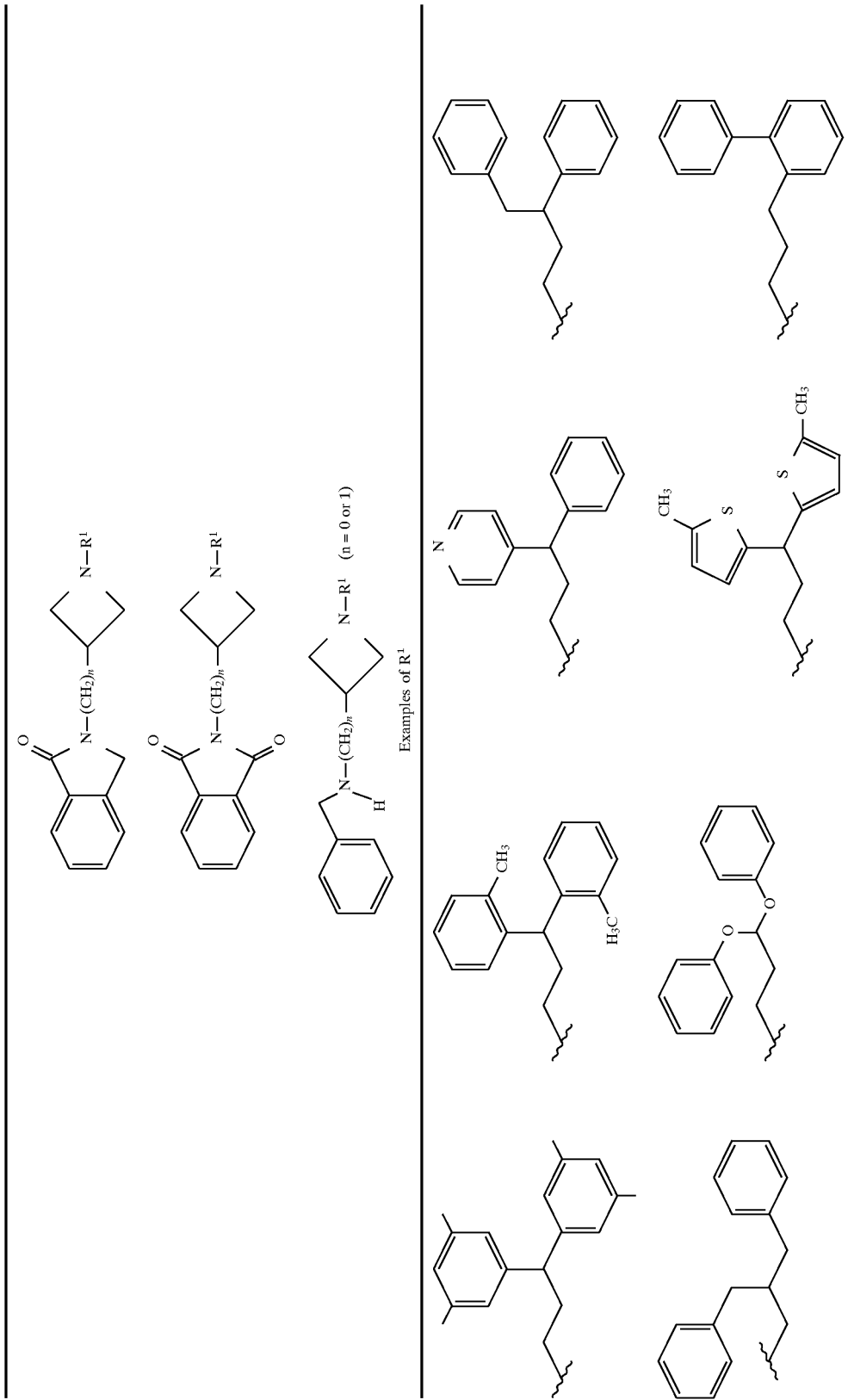

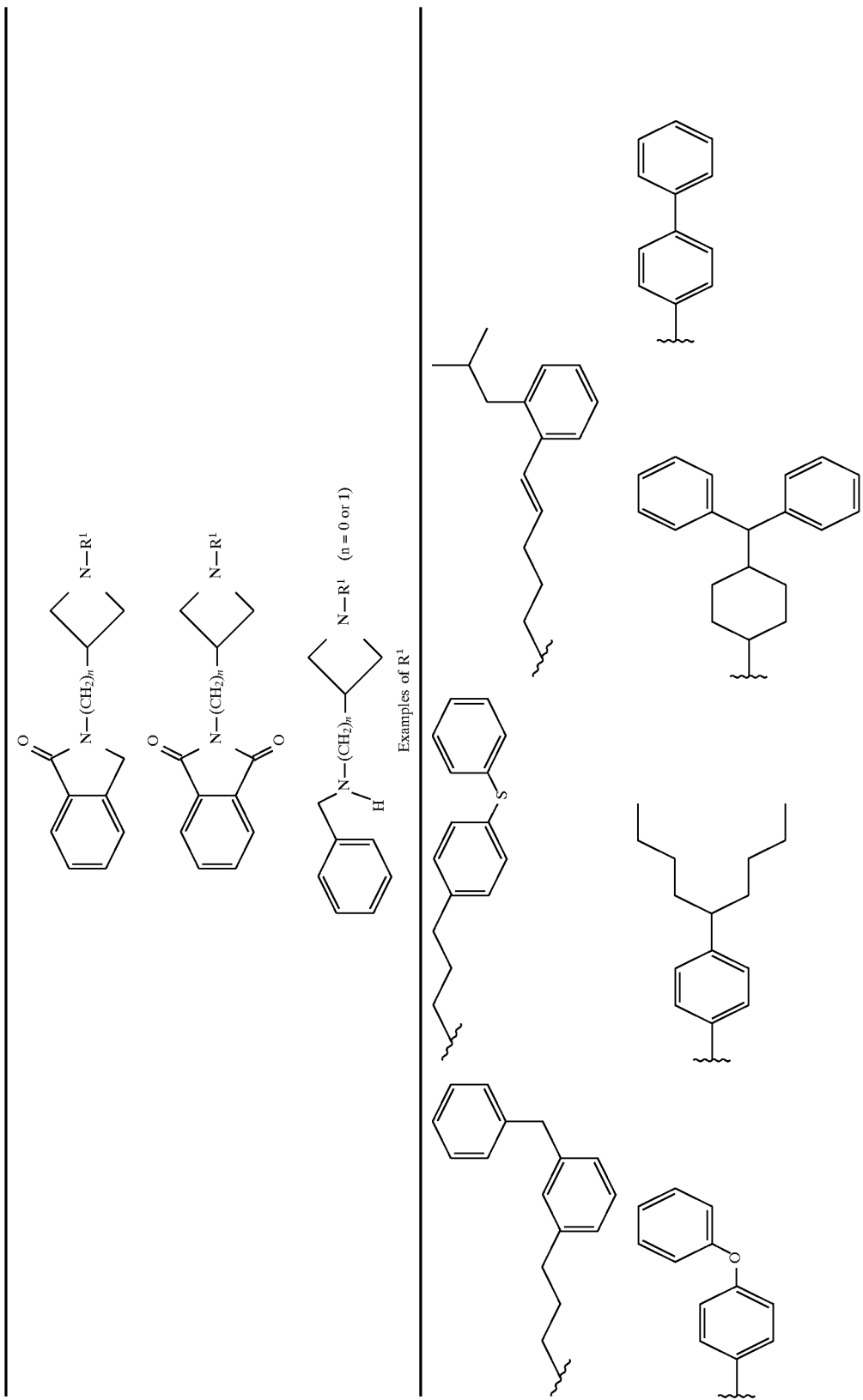

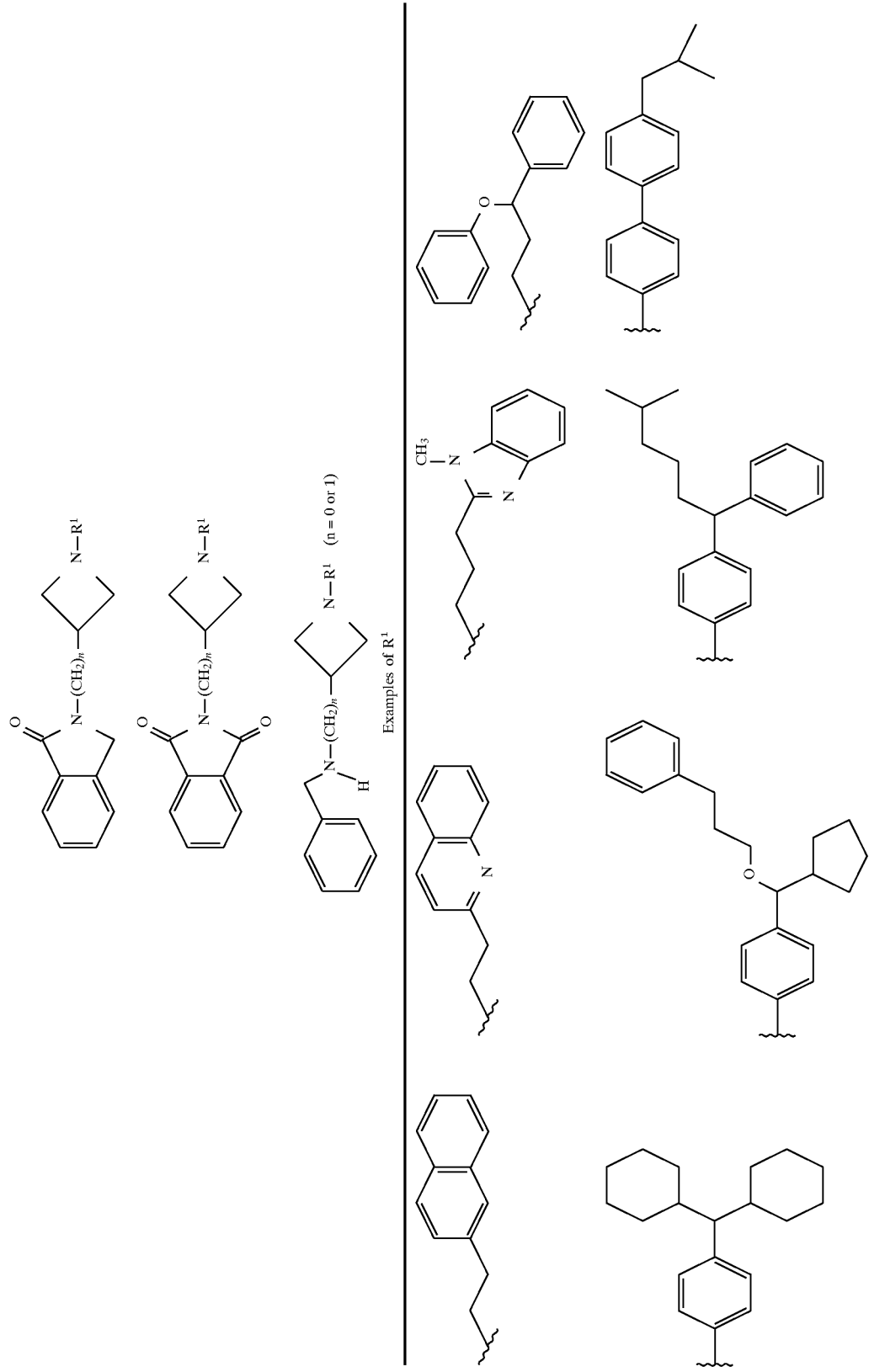

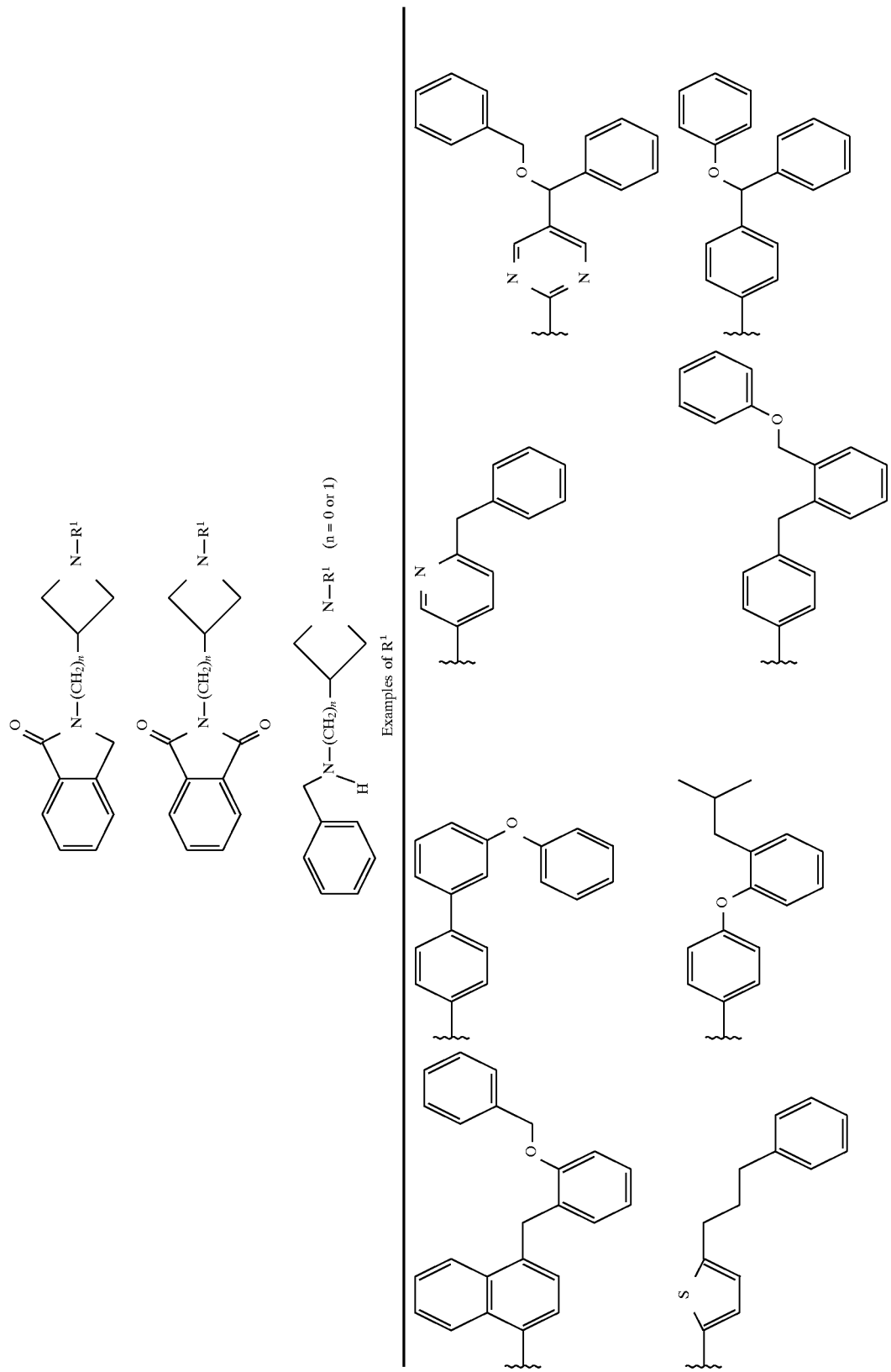

TABLE C-continued
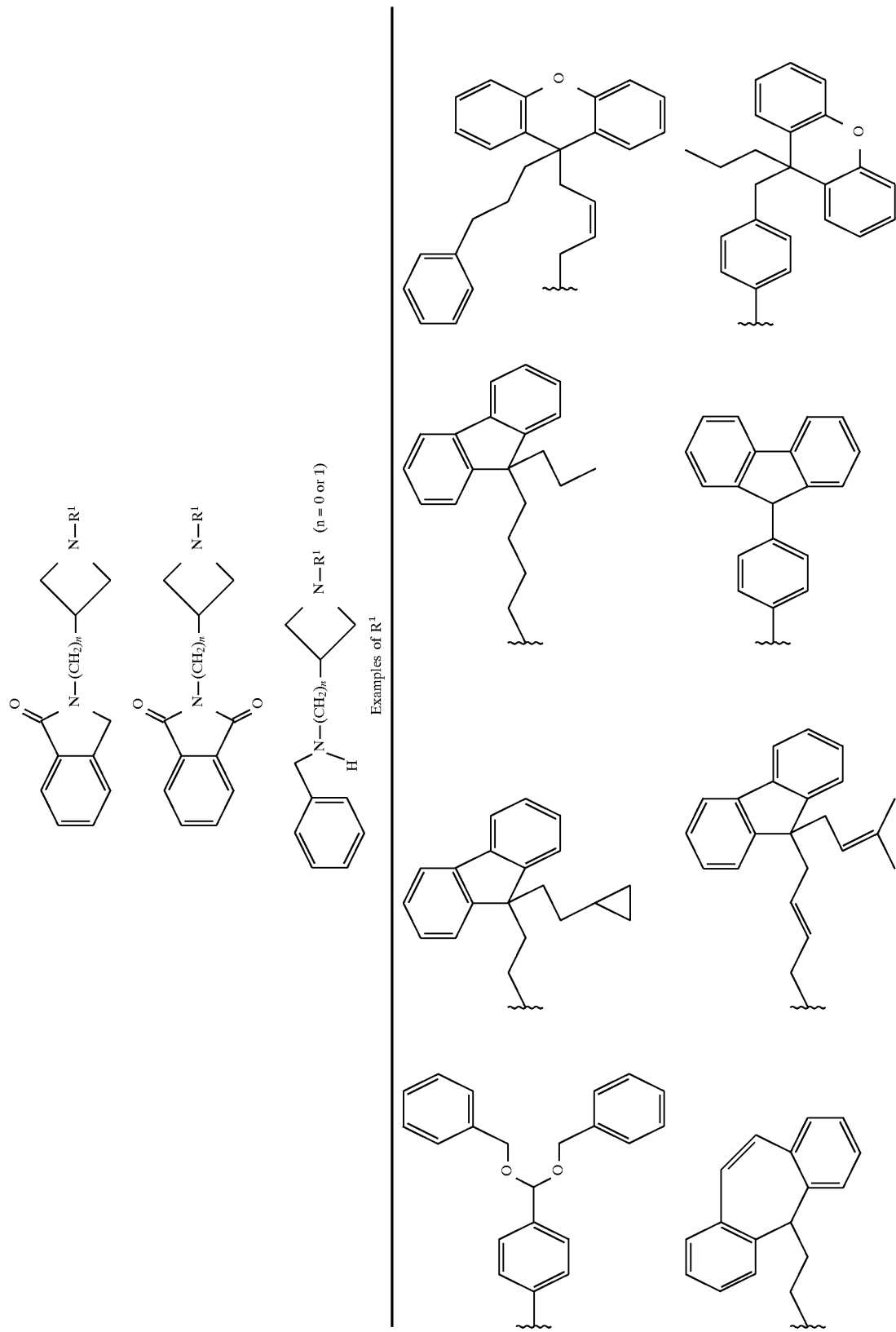

TABLE C-continued
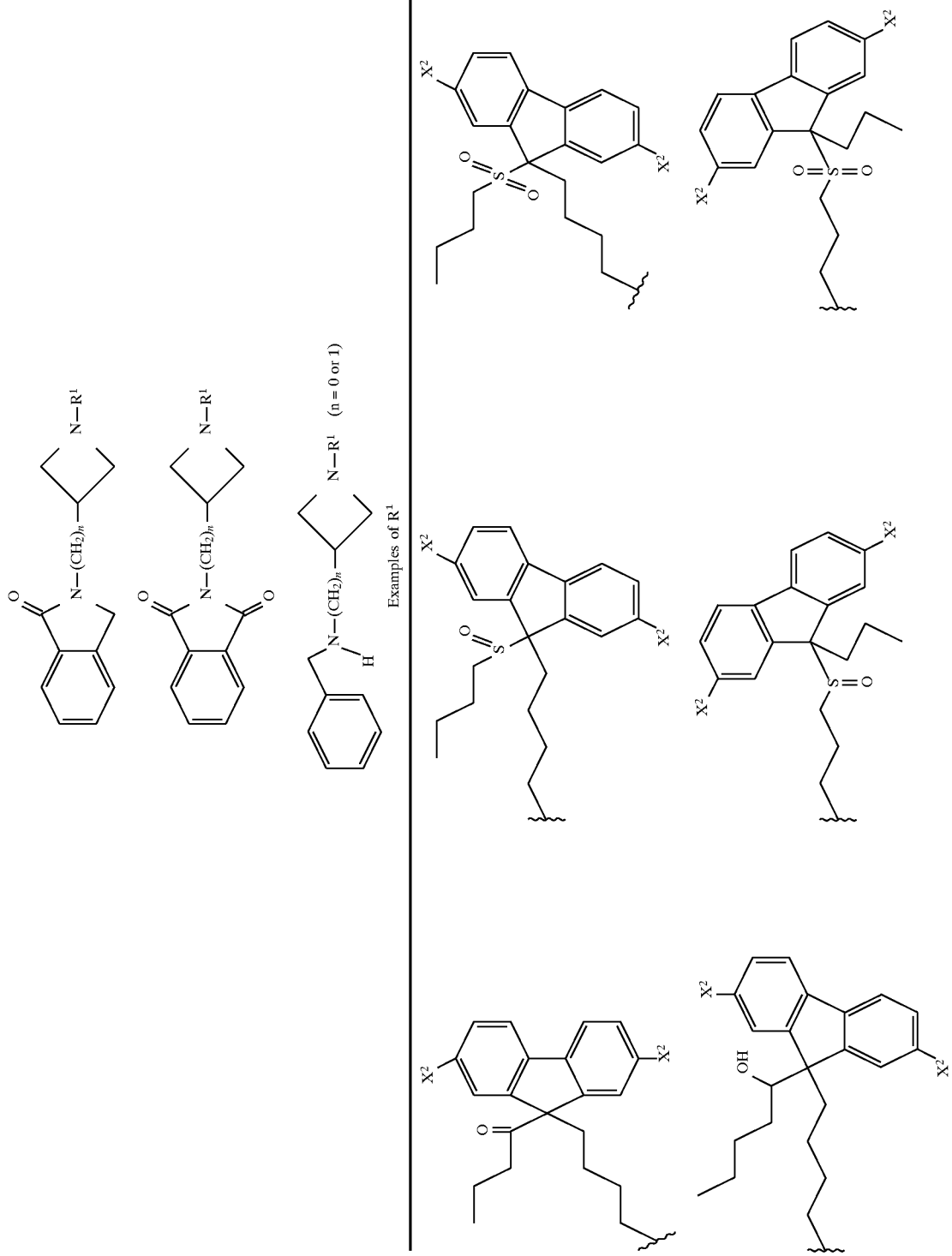
Examples of $R^1$

TABLE C-continued
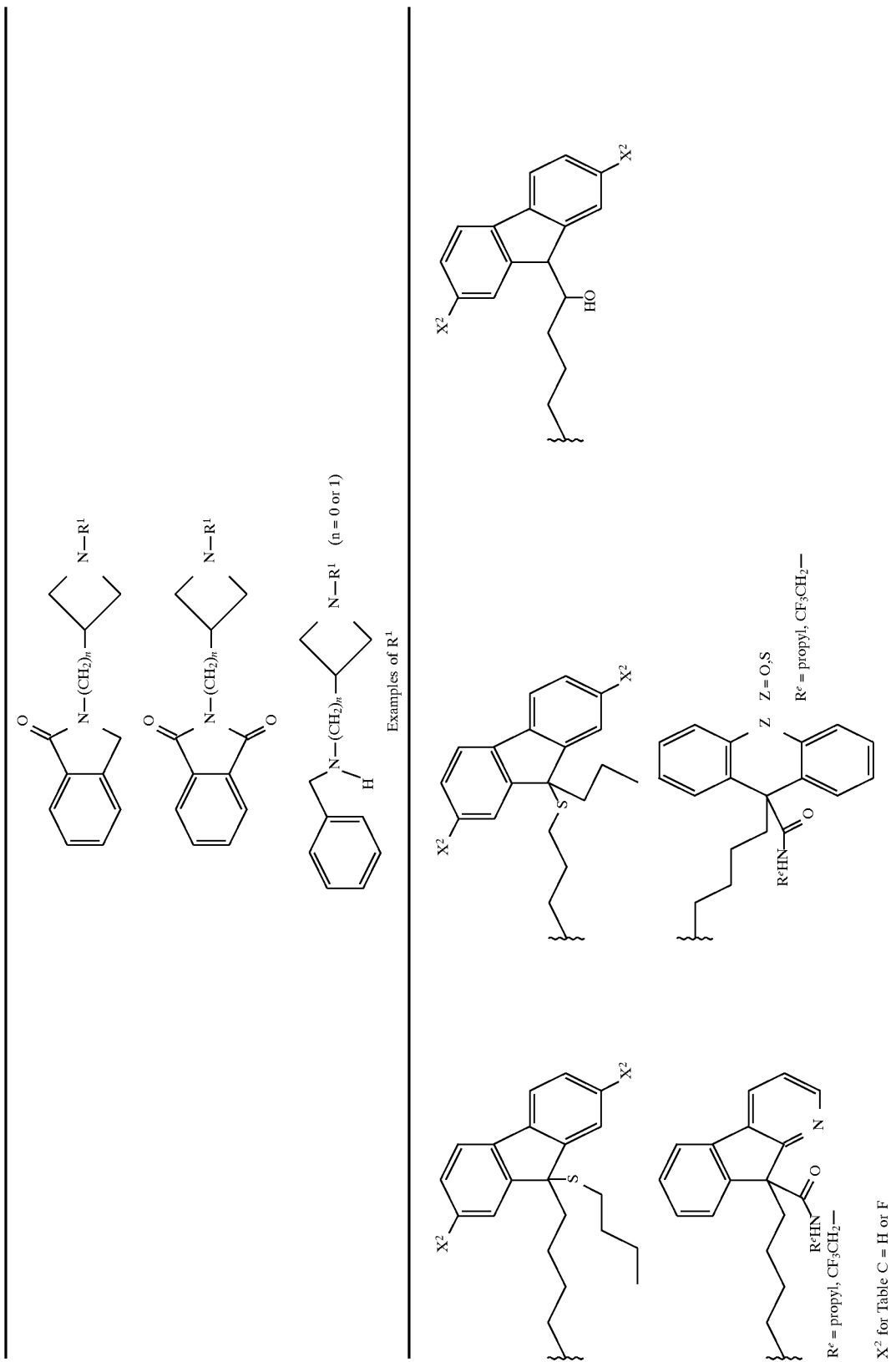
Examples of $R^1$
$R^e$ = propyl, $CF_3CH_2$—
$X^2$ for Table C = H or F TABLE D
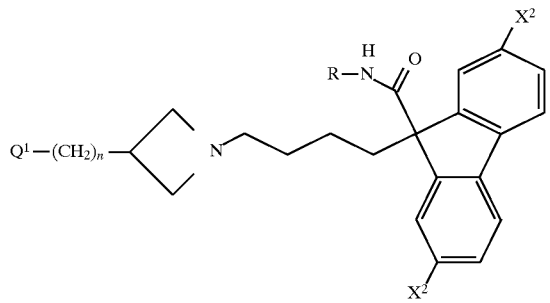
$X^2$ = H or F, n is 0 or 1
Example of R
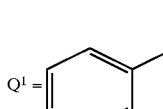

TABLE D-continued
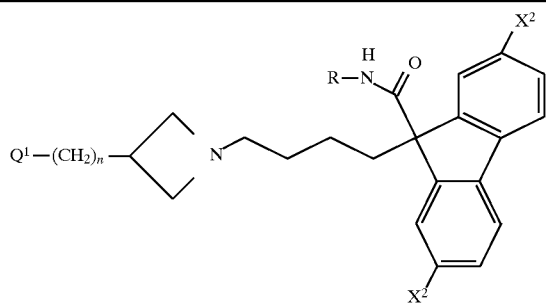
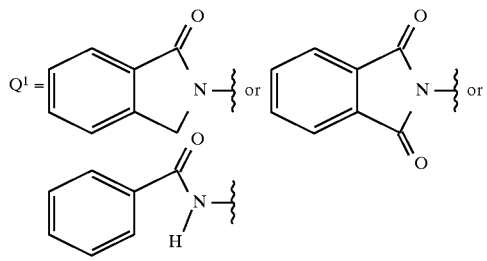
$X^2$ = H or F, n is 0 or 1
Example of R
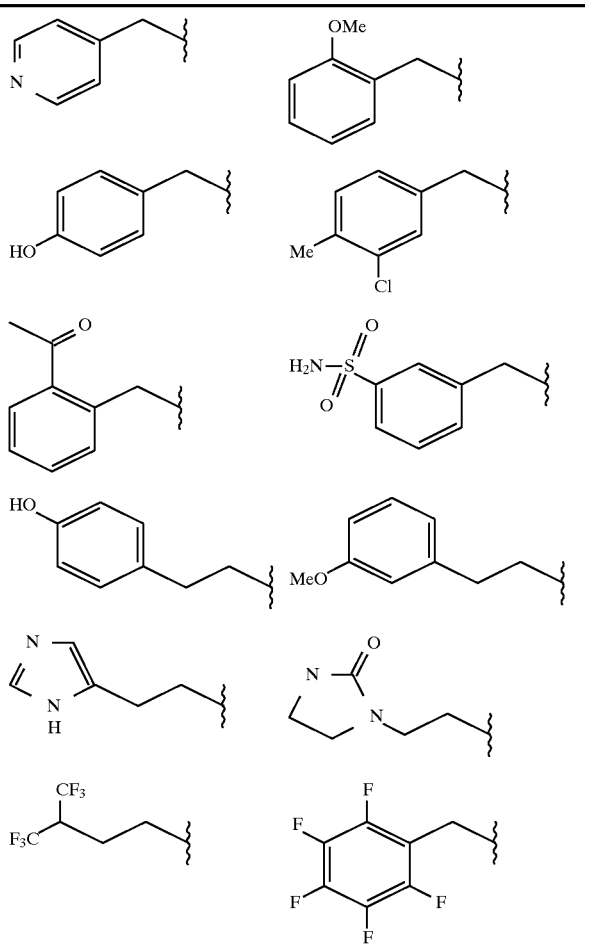

TABLE F
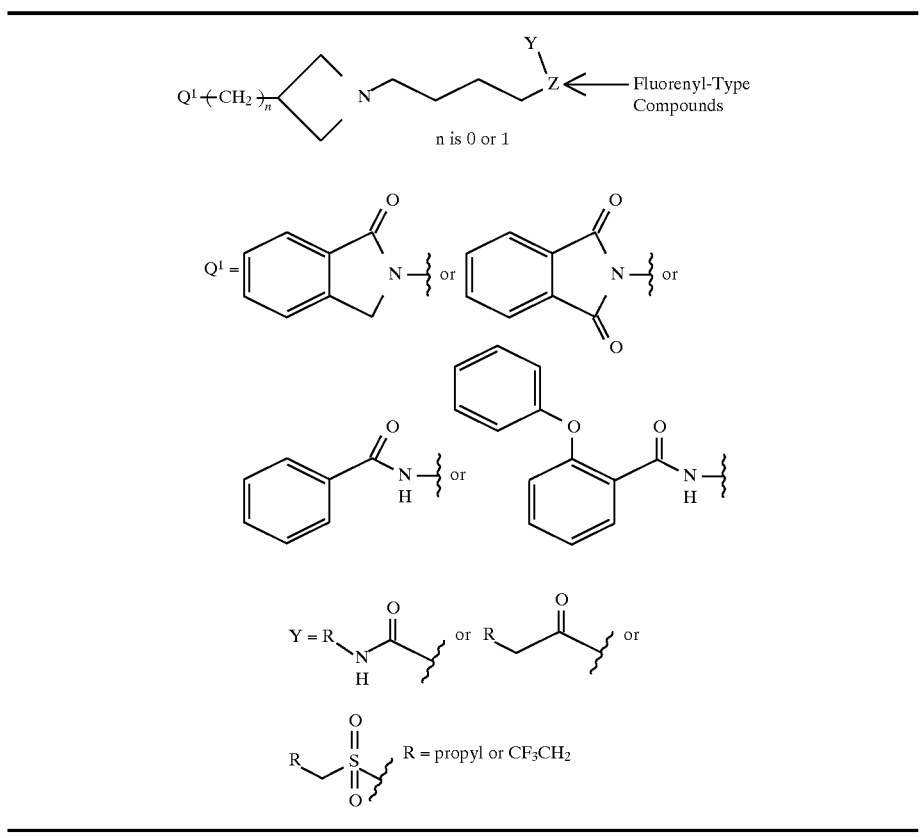
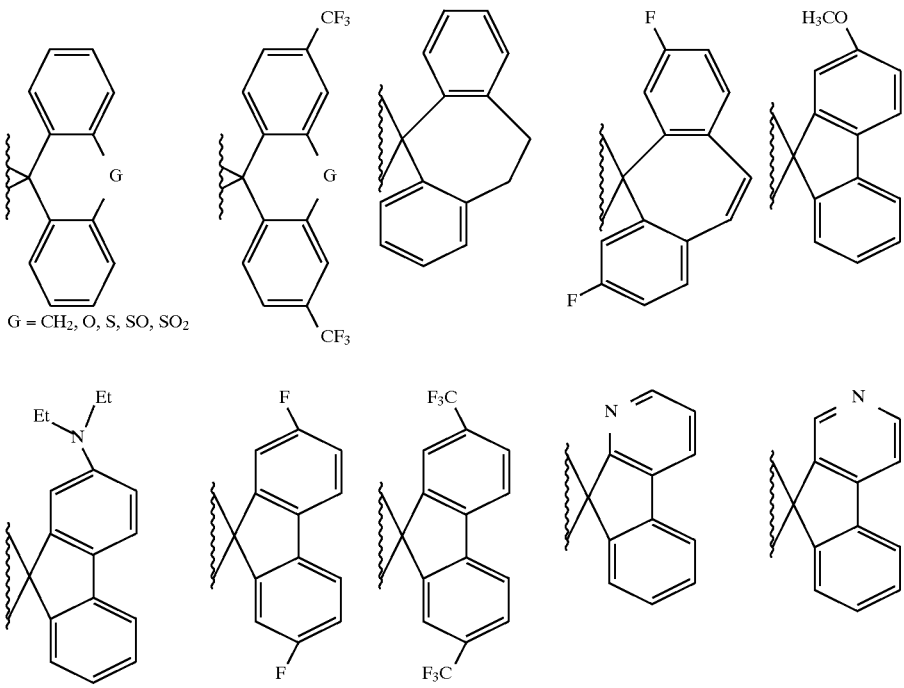

TABLE F-continued
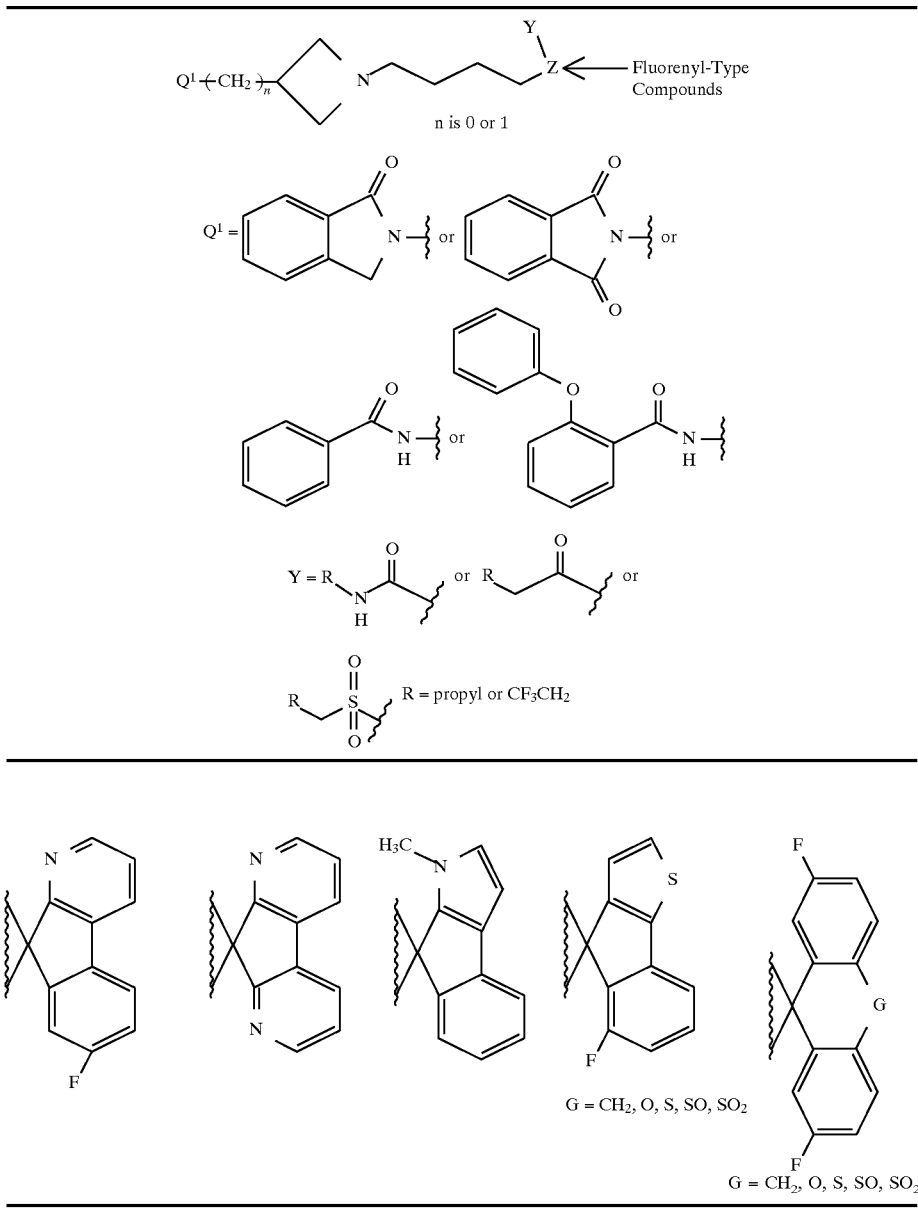

TABLE G
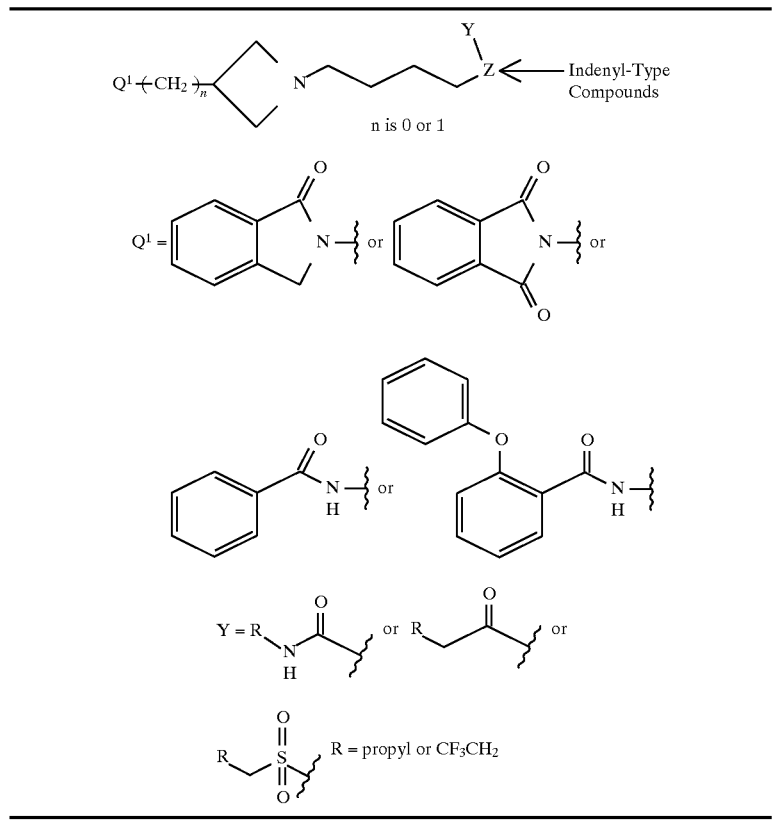
Indenyl-Type Rings: Z =
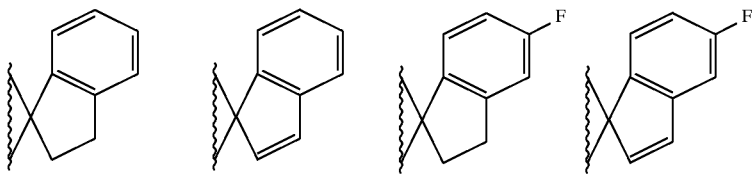
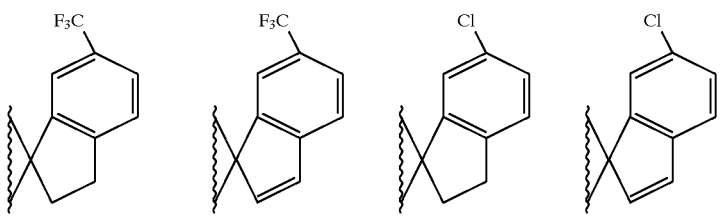
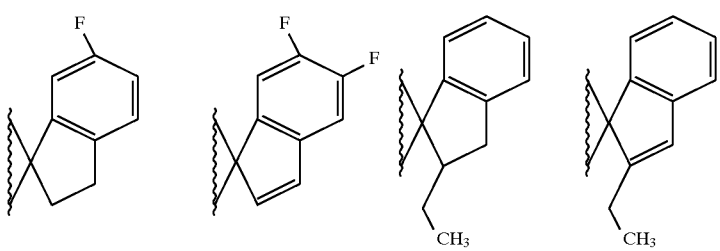

TABLE G-continued
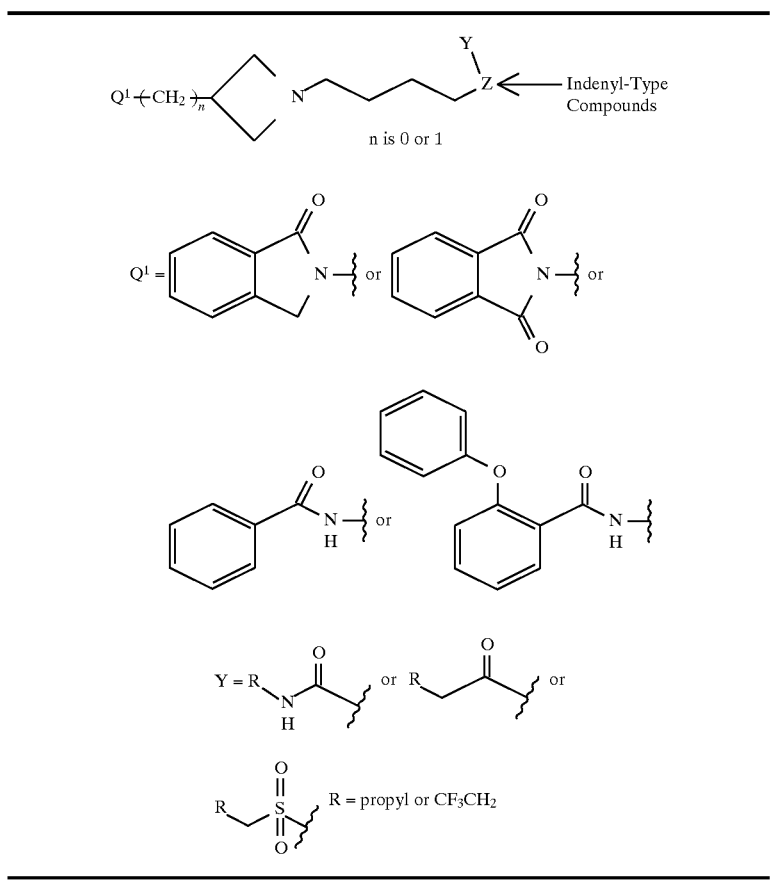
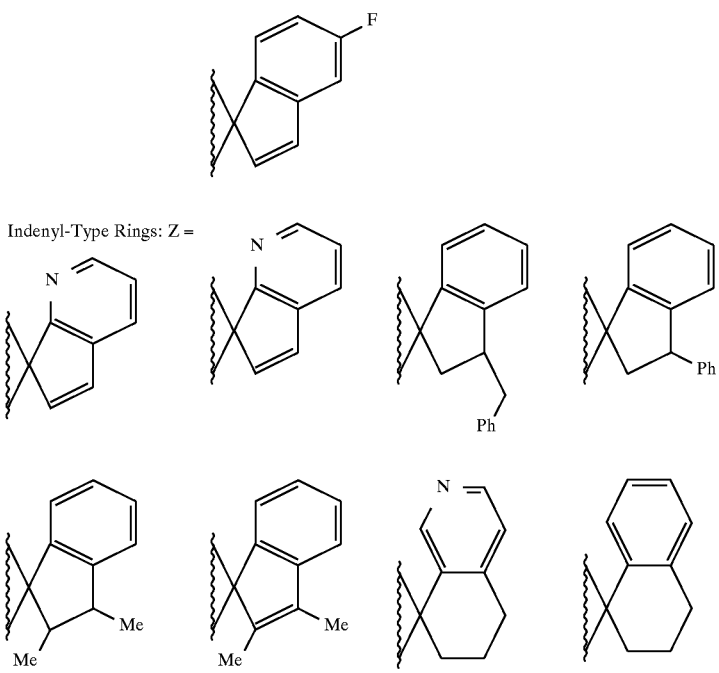

TABLE G-continued
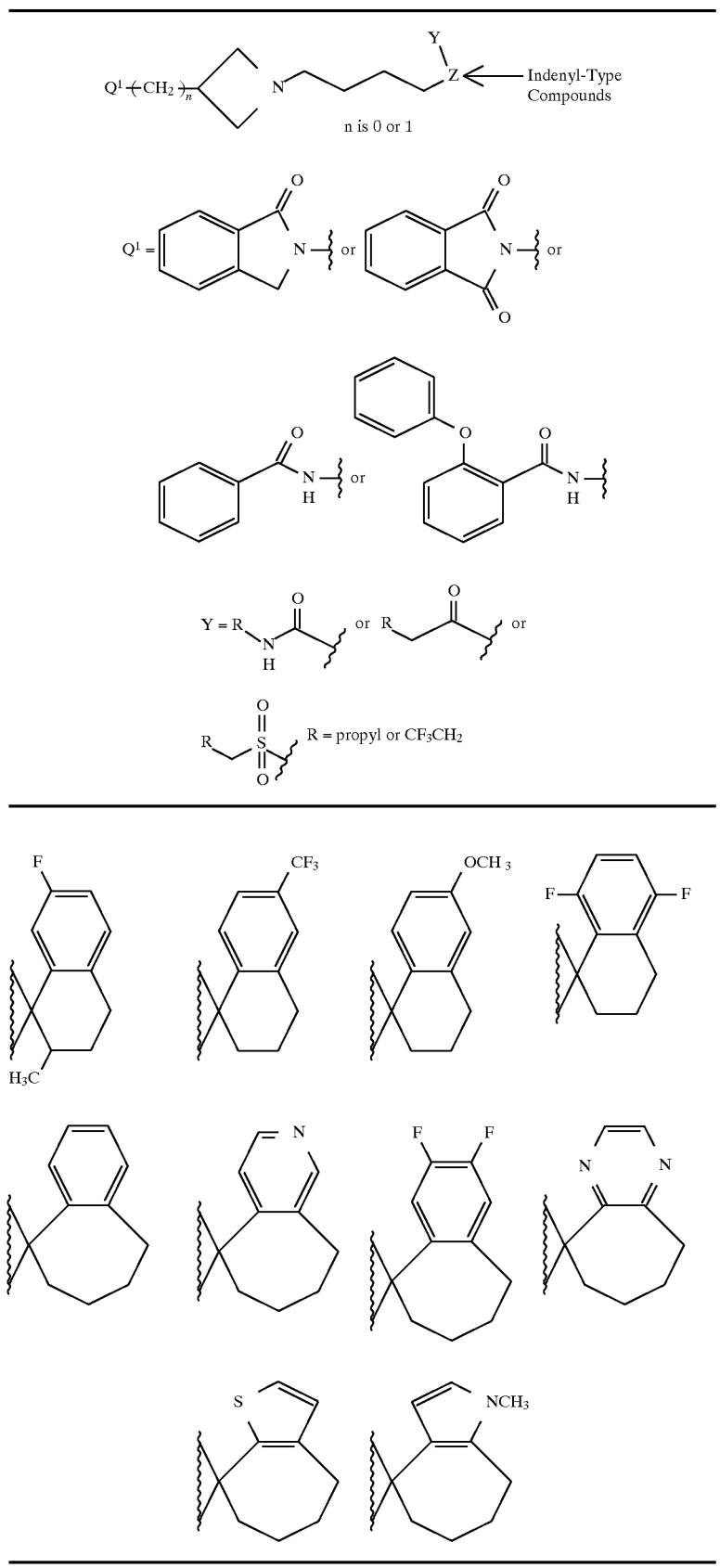

TABLE H

X¹ is H or F, n is 0 or 1

Example of R

EXAMPLE 337
cis-9-[4-[3-(2,3-Dihydro-1H-isoindol-2-yl)-1-azetidinyl]butyl]-N-propyl-9H-fluorene-9-carboxamide, N-oxide

EXAMPLE 338
2-[1-[4-[9-(Butylsulfonyl)-9H-fluoren-9-yl]butyl]-2-azetidinyl]-2,3-dihydro-1H-isoindol-1-one

EXAMPLE 339
9-[4-[[3-[(1,1-Dimethylethoxy)carbonyl]amino]-1-azetidinyl]butyl]-2,7-difluoro-N-(2,2,2-trifluoroethyl)-9H-fluorene-9-carboxamide

EXAMPLE 340
9-[4-[3-[(2-Phenoxybenzoyl)amino]-1-azetidinyl]-butyl]-N-(2,2,2-trifluoroethyl)-9H-fluorene-9-carboxamide, monohydrochloride

EXAMPLE 341
9-[4-[[3-(Benzoylamino)-1-azetidinyl]butyl]-2,7-difluoro-N-(2,2,2-trifluoroethyl)-9H-fluorene-9-carboxamide

EXAMPLE 342
9-[4-[[3-(1,3-Dihydro-1,3-dioxo-2H-isoindol-2-yl)-1-azetidinyl]butyl]-2,7-difluoro-N-(2,2,2-trifluoroethyl)-9H-fluorene-9-carboxamide

EXAMPLE 343
2,7-Difluoro-9-[4-[[3-[(2-phenoxybenzoyl)amino]-1-azetidinyl]butyl]-N-(2,2,2-trifluoroethyl)-9H-fluorene-9-carboxamide

EXAMPLE 344
9-[4-[3-(Benzoylamino)-1-azetidinyl]butyl]-N-(2,2,2-trifluoroethyl)-9H-fluorene-9-carboxamide, monohydrochloride

EXAMPLE 345
2,3-Dihydro-2-[1-[4-[9-(1-oxopentyl)-9H-fluoren-9-yl]butyl]-2-azetidinyl]-1H-isoindol-1-one, monohydrochloride

EXAMPLE 346
2,3-Dihydro-2-[1-(1-oxo-3,3-diphenylpropyl)-2-azetidinyl]-1H-isoindol-1-one

EXAMPLE 347
[1-[4-[9-[(Propylamino)carbonyl]-9H-fluoren-9-yl]-butyl]-2-azetidinyl]carbamic acid, phenylmethyl ester, monohydrochloride

EXAMPLE 348
9-[4-[3-(2,3-Dihydro-1-oxo-1H-isoindol-2-yl)-1-azetidinyl]butyl]-N-(2,2,2-trifluoroethyl)-9H-fluorene-9-carboxamide, hydrochloride salt

EXAMPLE 349
9-[4-[3-(2,3-Dihydro-1-oxo-1H-isoindol-2-yl)-1-azetidinyl]butyl]-N-(2,2,2-trifluoroethyl)-9H-fluorene-9-carboxamide, hydrochloride salt

EXAMPLE 350
9-[4-[3-(Benzoylamino)-1-azetidinyl]butyl]-N-propyl-9H-fluorene-9-carboxamide

EXAMPLE 351
9-[4-[3-(1,3-Dihydro-1,3-dioxo-2H-isoindol-2-yl)-1-azetidinyl]-butyl]-N-propyl-9H-fluorene-9-carboxamide

EXAMPLE 352
9-[4-[3-(2,3-Dihydro-1-oxo-1H-isoindol-2-yl)-1-azetidinyl]butyl]-N-(2,2,3,3,4,4,4-heptafluoro-butyl)-9H-fluorene-9-carboxamide, monohydrochloride

EXAMPLE 353
9-[4-[[3-[(1,1-Dimethylethoxy)carbonyl]amino]-1-azetidinyl]butyl]-3,6-difluoro-N-(2,2,2-trifluoroethyl)-9H-fluorene-9-carboxamide

EXAMPLE 354
1-[4-[3-(1,3-Dihydro-1-oxo-2H-isoindol-2-yl)-1-azetidinyl]butyl]-2-methyl-N-(2,2,2-trifluoroethyl)-1H-indene-1-carboxamide

EXAMPLE 355
9-[4-[3-(1,3-Dihydro-1-oxo-2H-isoindol-2-yl)-1-azetidinyl]butyl]-N-(2,2,3,3,3-pentafluoropropyl)-9H-fluorene-9-carboxamide, monohydrochloride

EXAMPLE 356
1-[4-[3-(1,3-Dihydro-1-oxo-2H-isoindol-2-yl)-1-azetidinyl]butyl]-N-(2,2,2-trifluoroethyl)-1H-indene-1-carboxamide

EXAMPLE 357
9-[4-[3-(Benzoylamino)-1-azetidinyl]butyl]-3,6-difluoro-N-(2,2,2-trifluoroethyl)-9H-fluorene-9-carboxamide

EXAMPLE 358
3,6-Difluoro-9-[4-[3-[(2-phenoxybenzoyl)amino]-1-azetidinyl]butyl]-N-(2,2,2-trifluoroethyl)-9H-fluorene-9-carboxamide Please note that in the Examples 359 to 475 for structures bearing only two single bonded substituents to nitrogen, the third substituent is always hydrogen, but it is not shown explicitly in the structures. Also, please note that in the Examples 359 to 475 for structures bearing oxygen and sulfurs with only one single bonded substituent, the second substituent is always hydrogen, but is not shown explicitly in the structures.

359

-continued
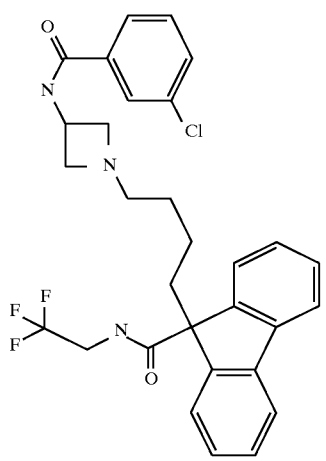
360
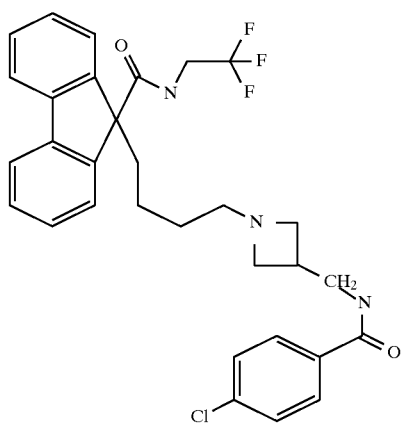
361
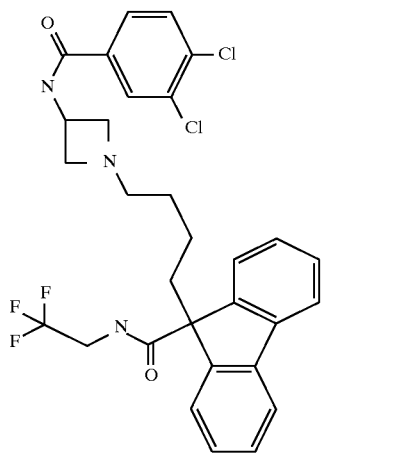
362

-continued
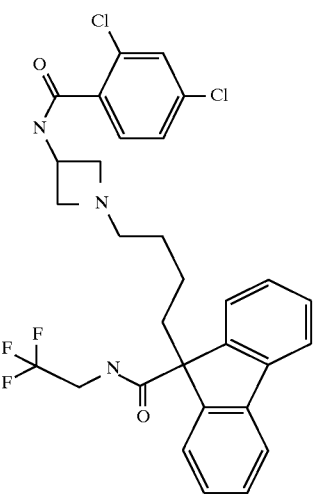
363
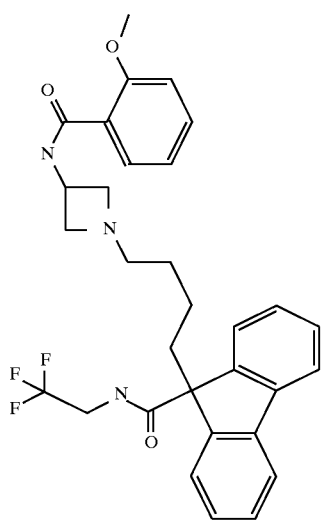
364
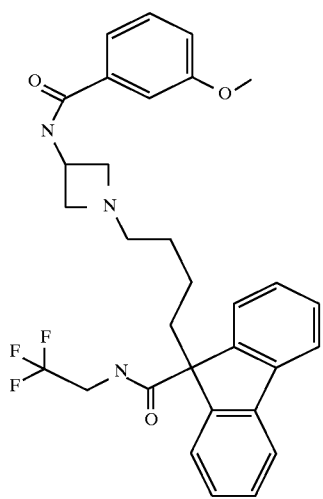
365

366
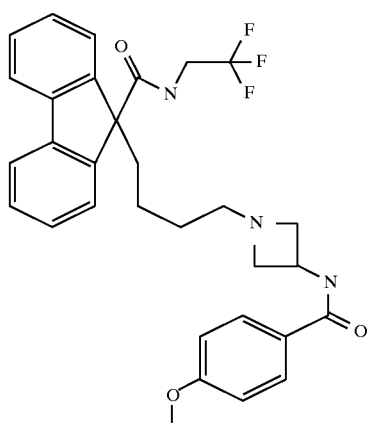
367
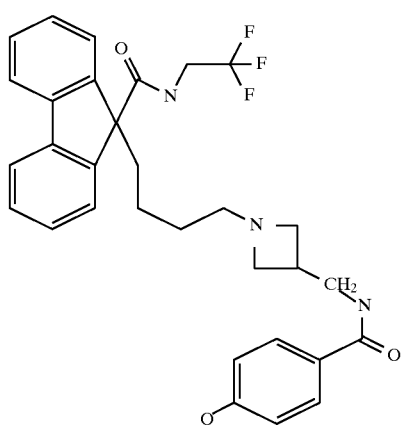
368
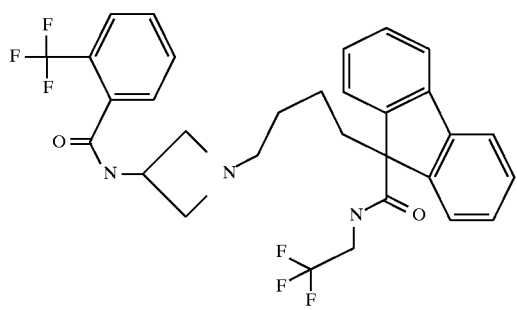
369
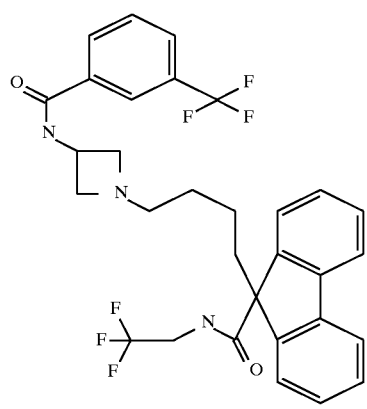

370
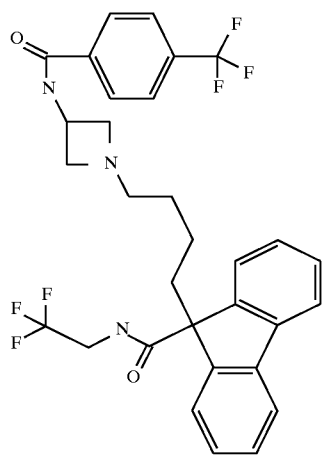
371
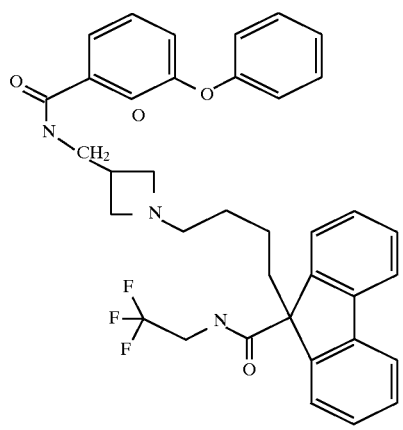
372
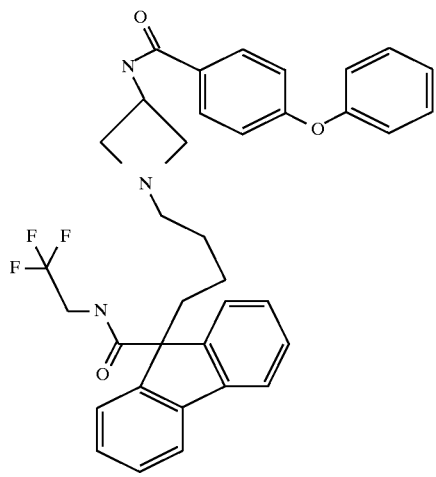

373
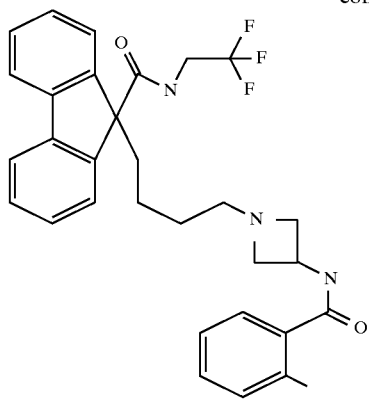
374
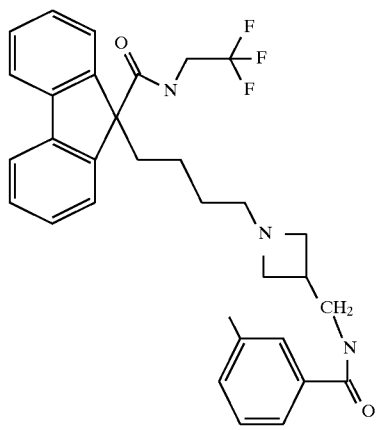
375
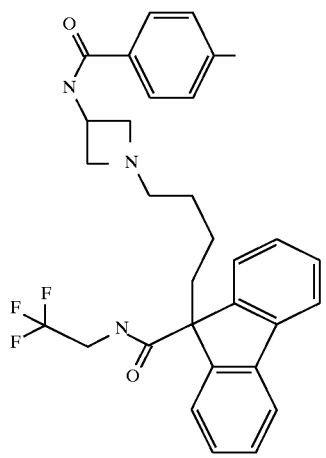
376
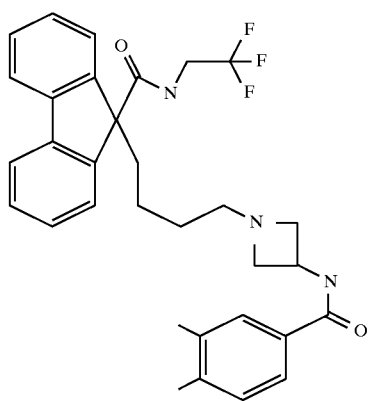

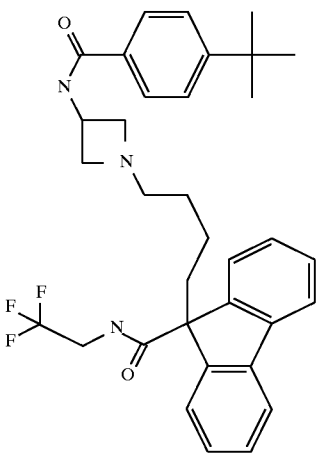
377
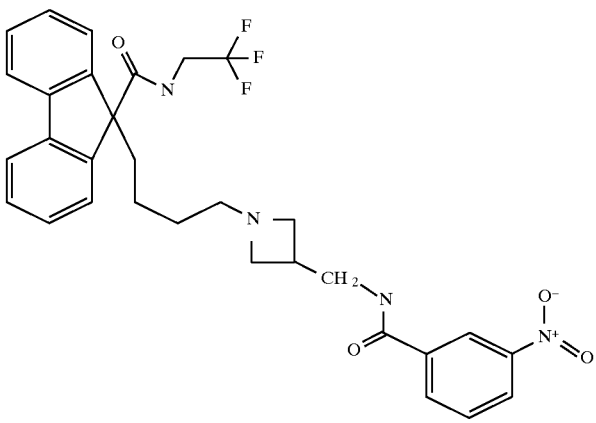
378
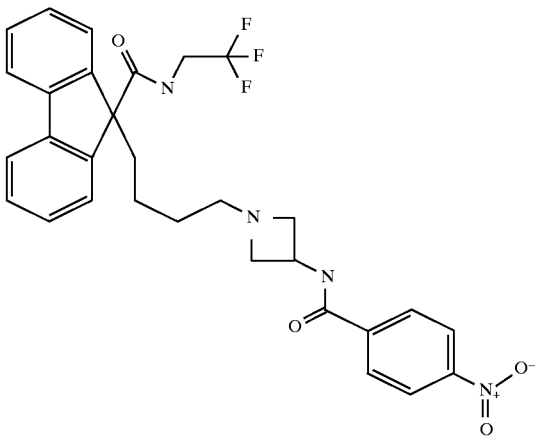
379
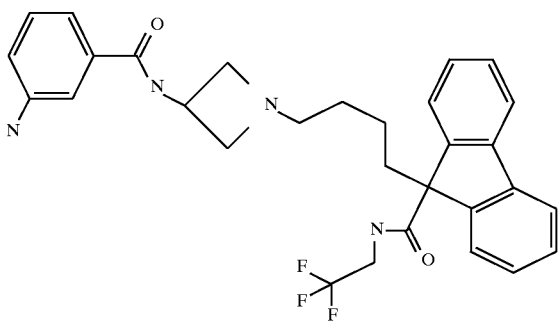
380

381
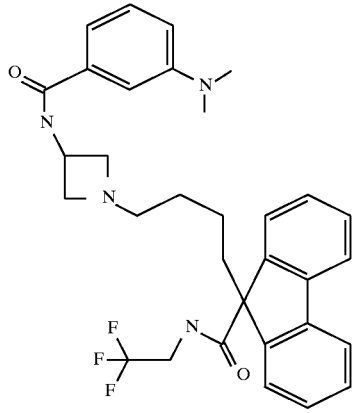
382
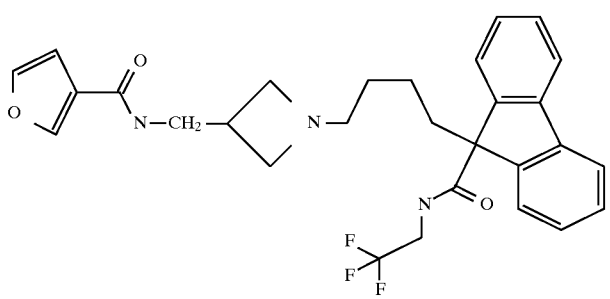
383
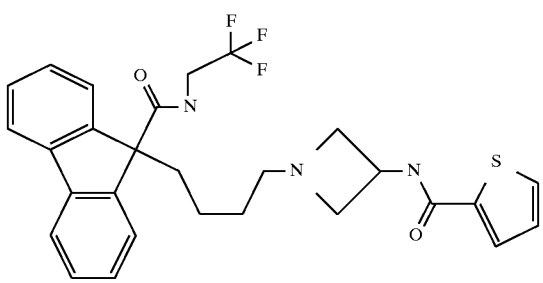
384
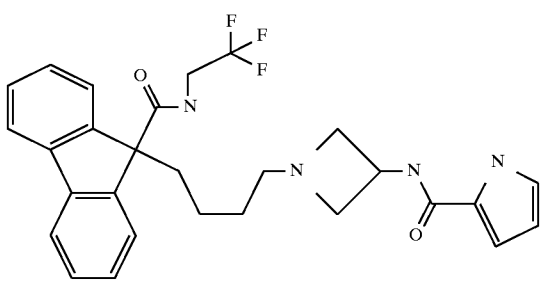
385
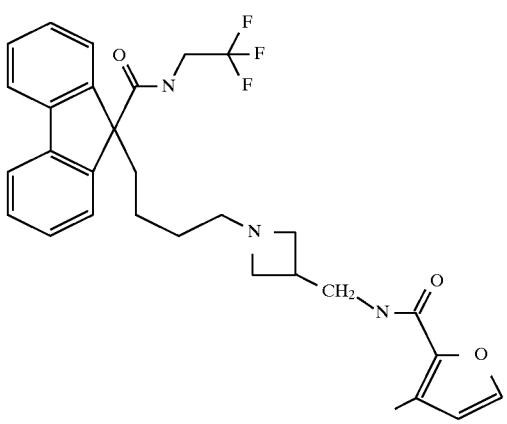

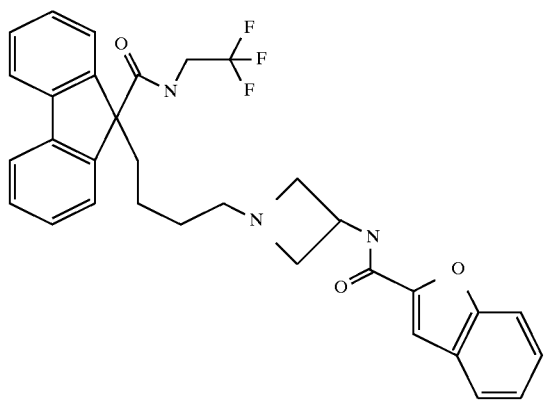
386
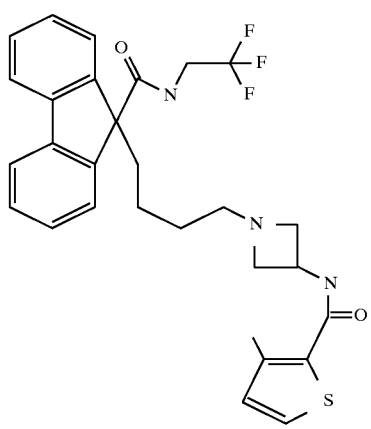
387
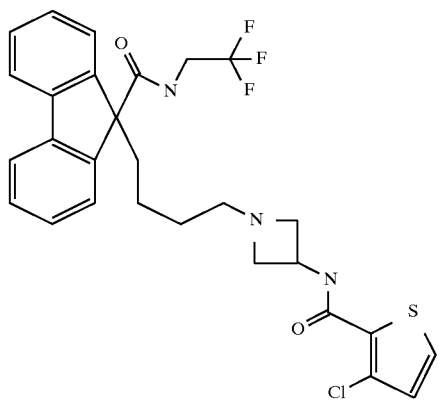
388
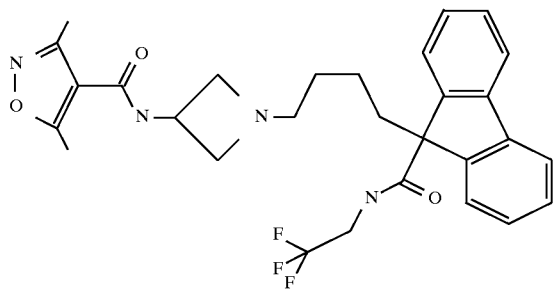
389

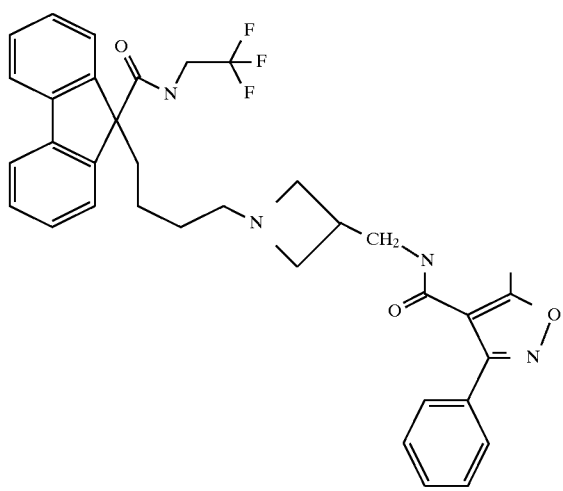
390
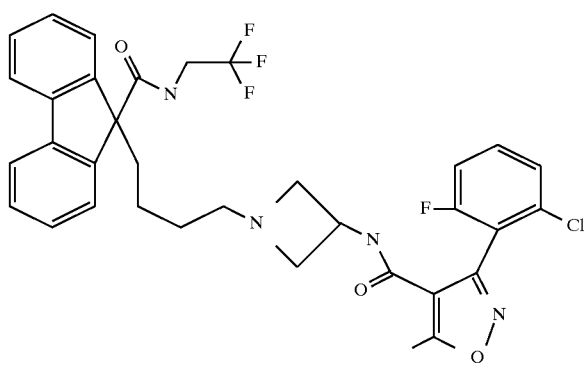
391
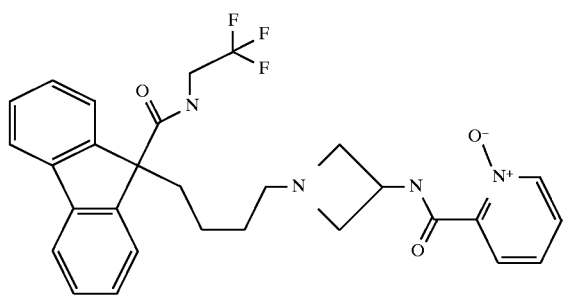
392
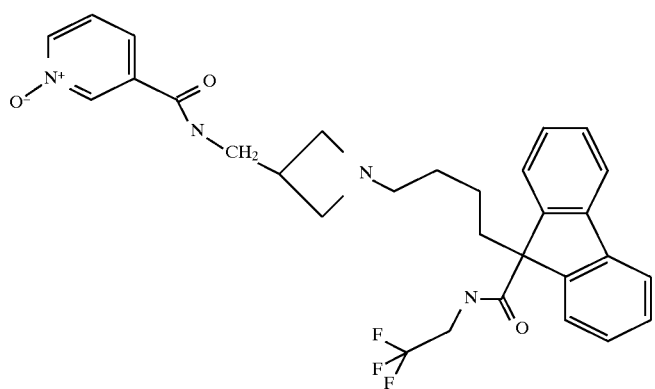
393

394
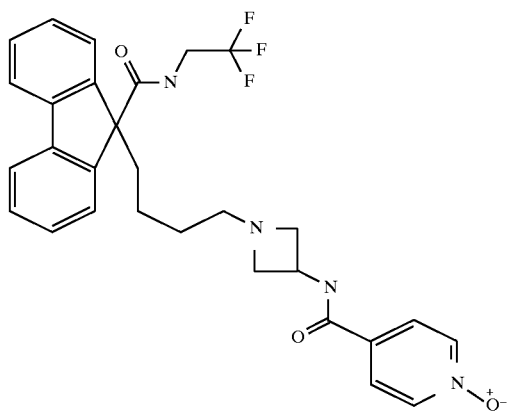
395
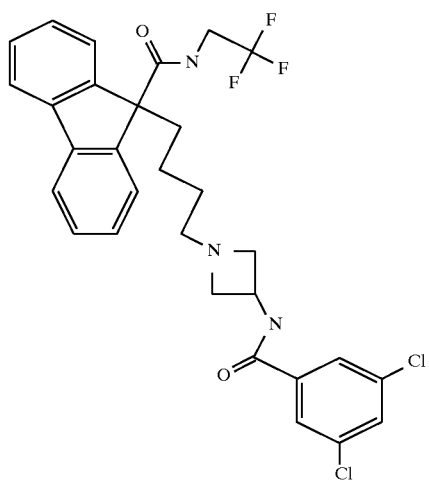
396
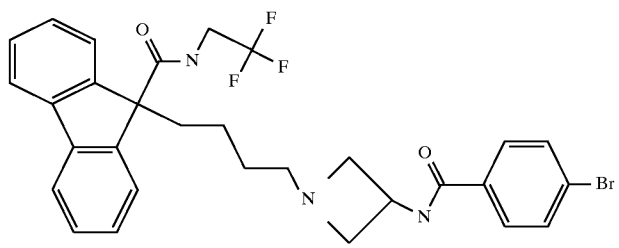
397
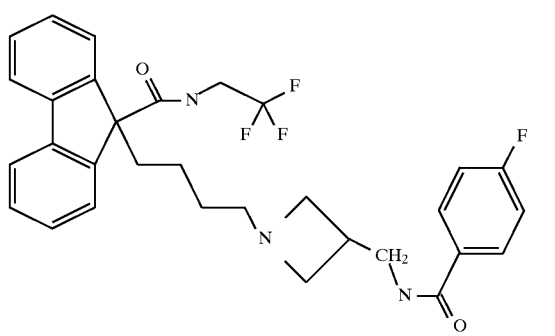

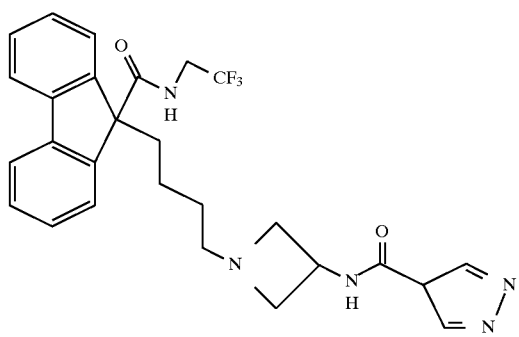
398
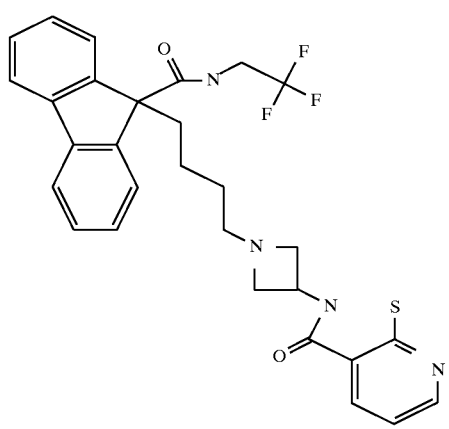
399
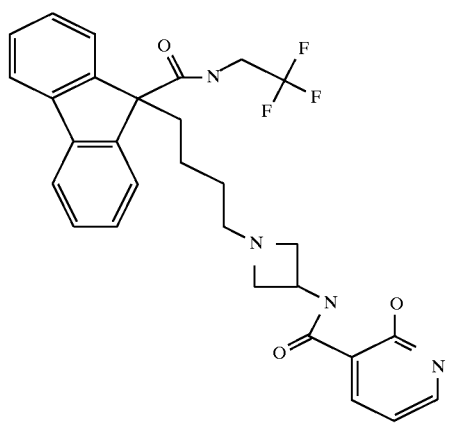
400
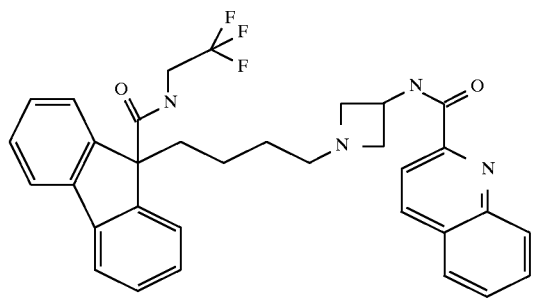
401

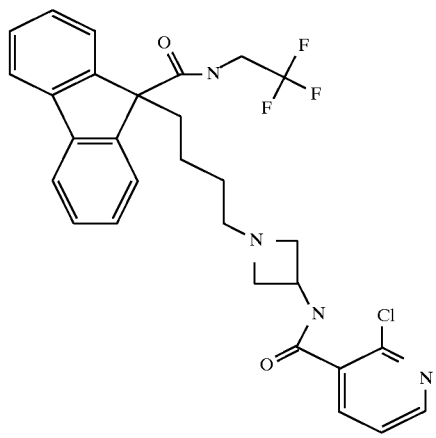
402
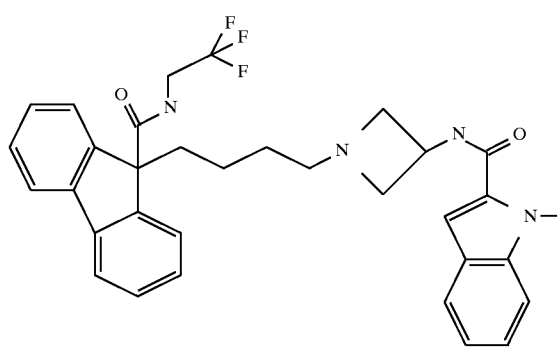
403
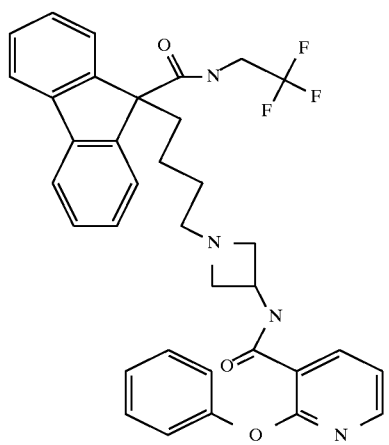
404
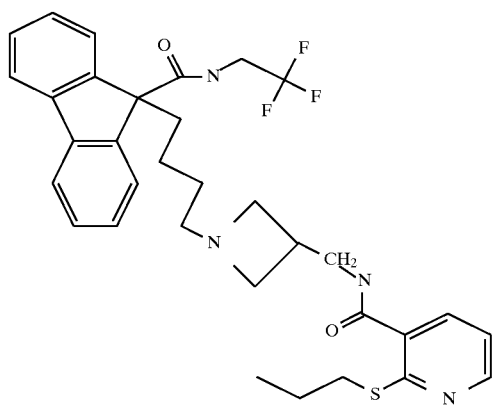
405

406
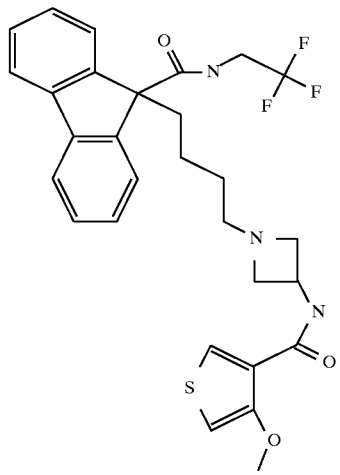
407
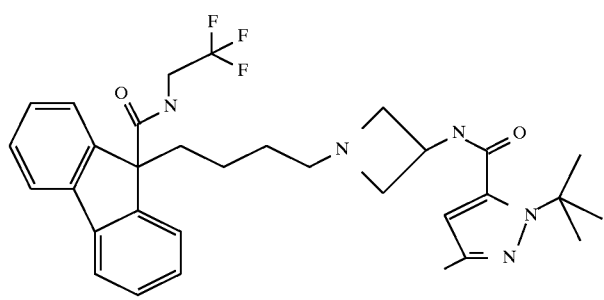
408
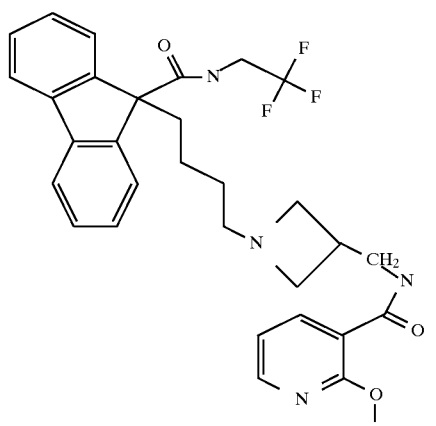
409
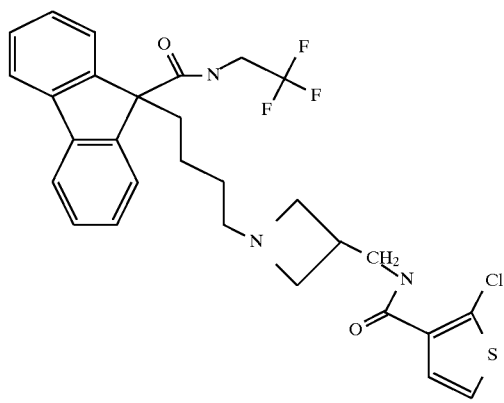

410
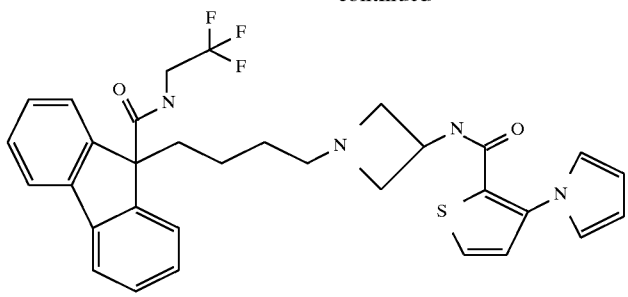
411
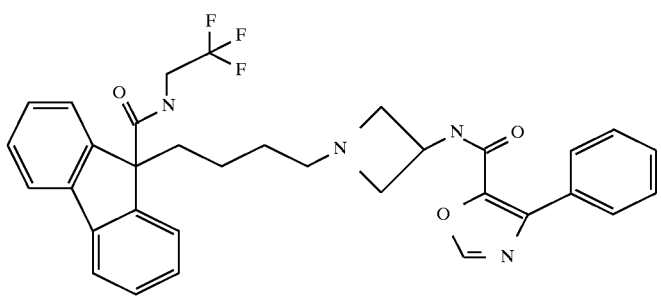
412
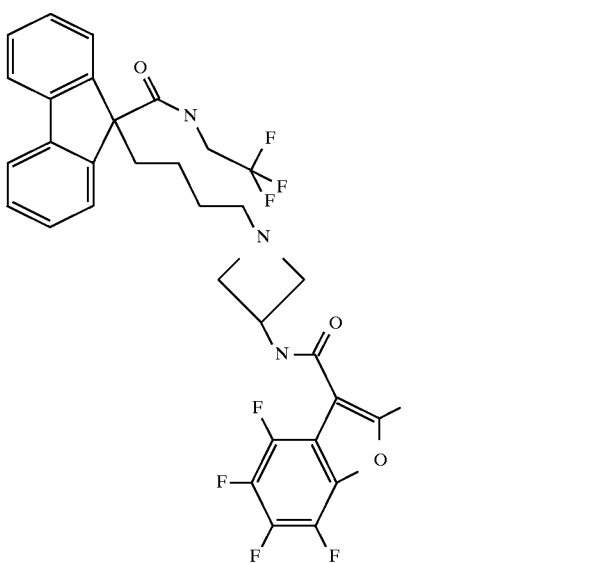
413
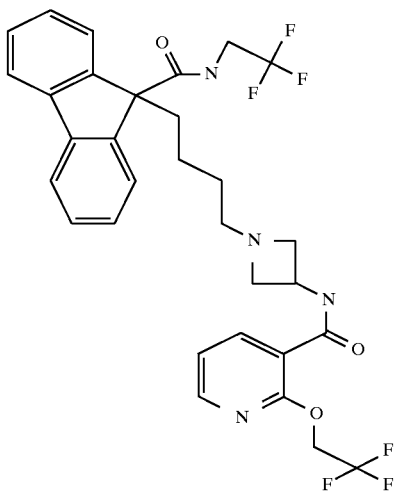

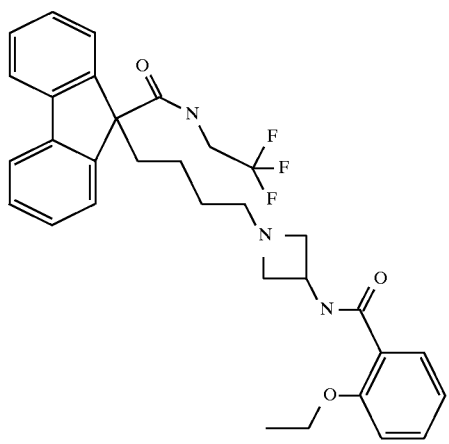
414
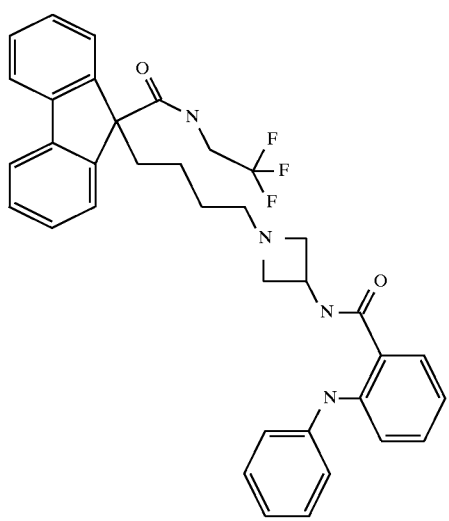
415
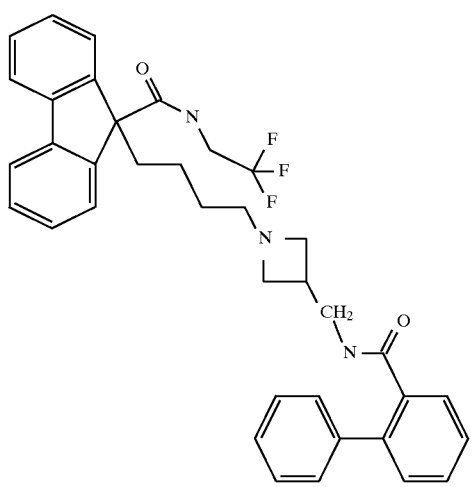
416

417
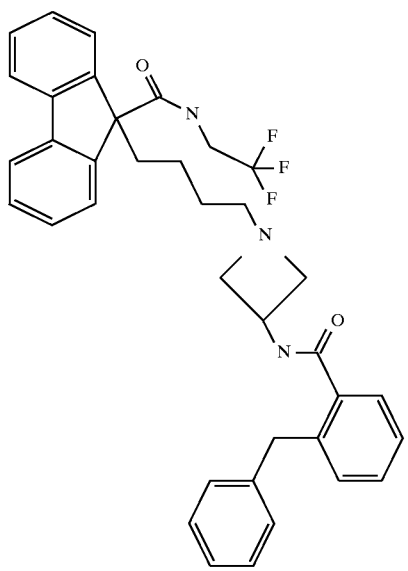
418
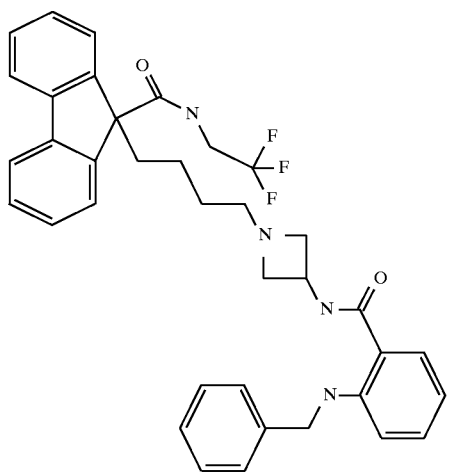
419
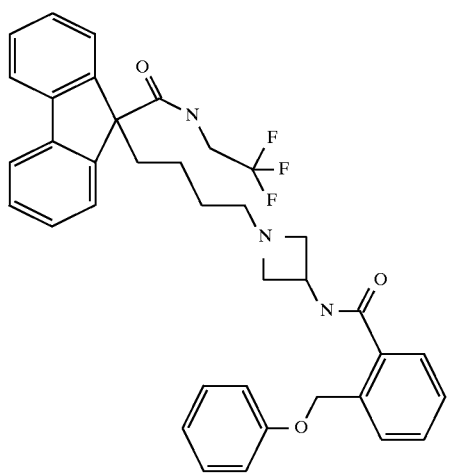

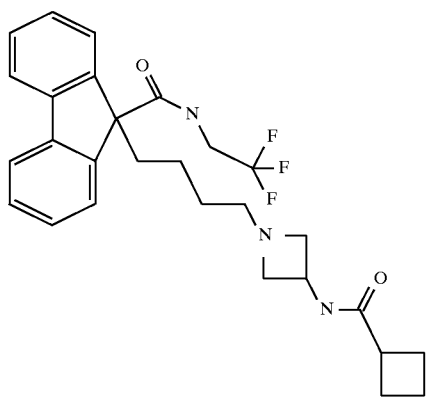
420
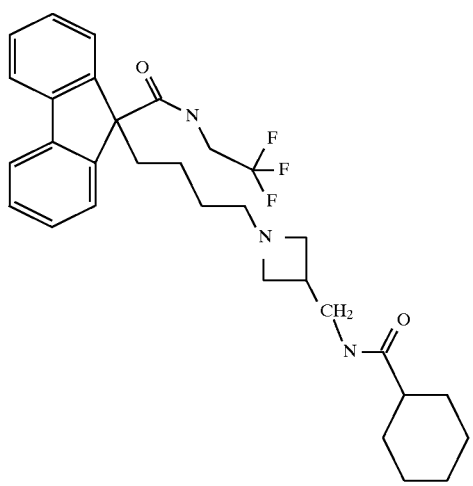
421
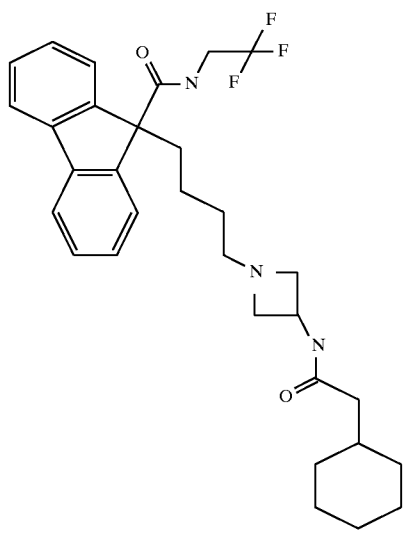
422

423
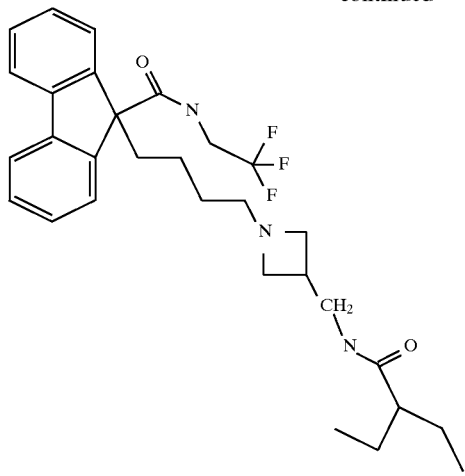
424
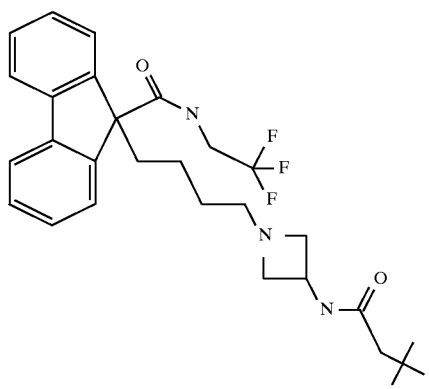
425
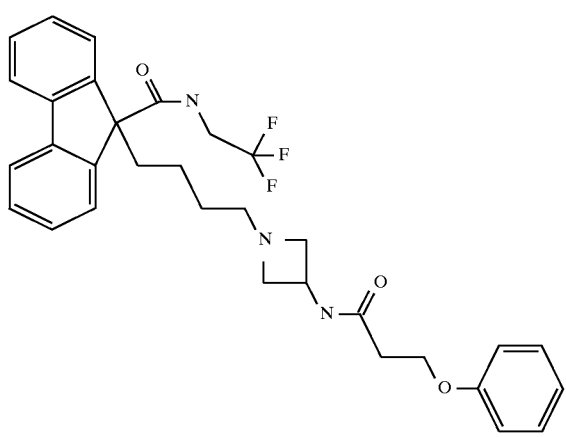
426
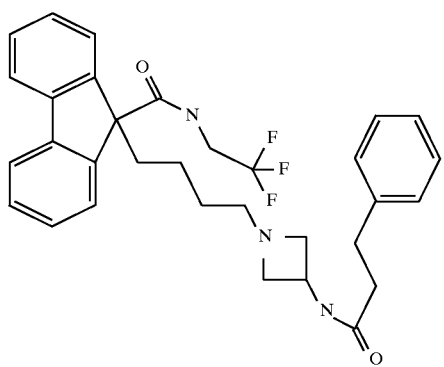

427
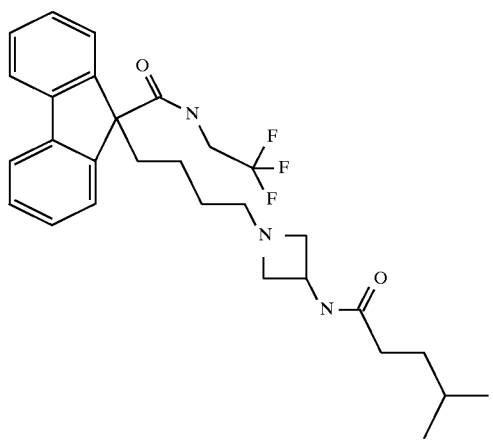
428
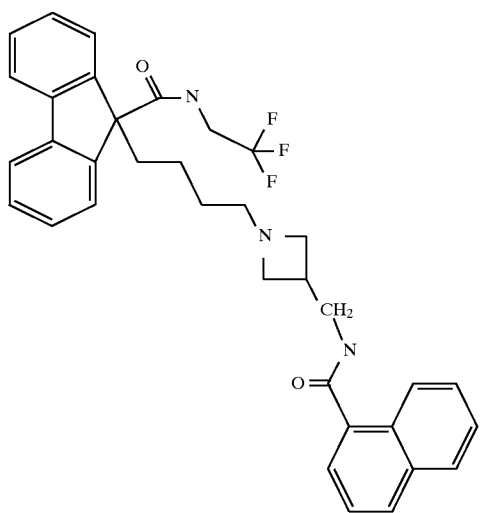
429
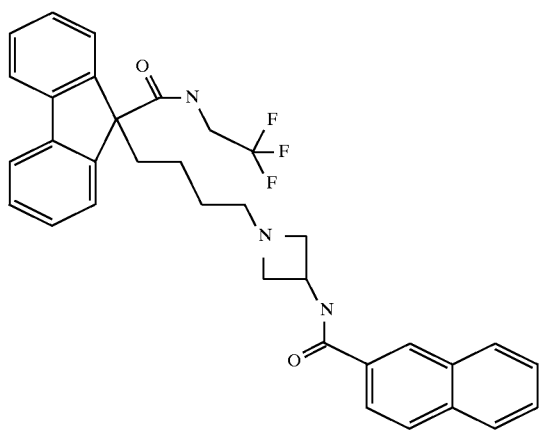

430
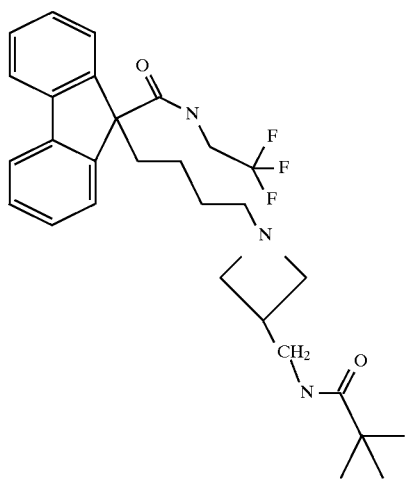
431
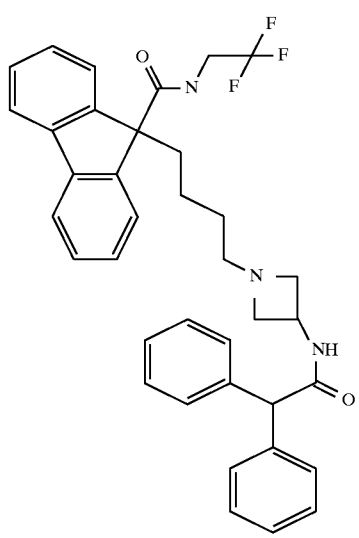
432
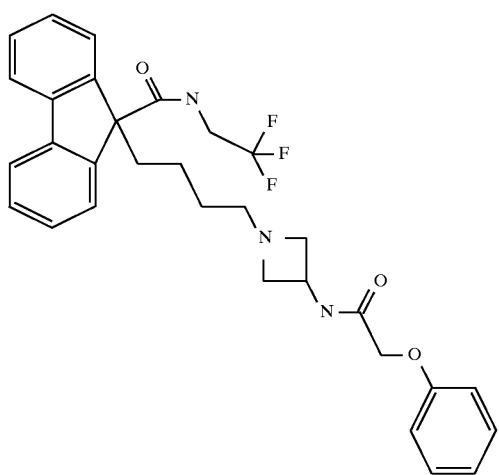

433
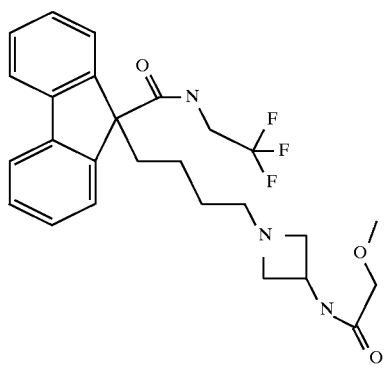
434
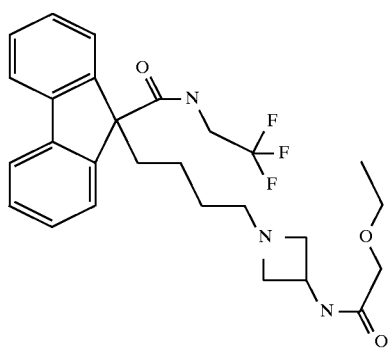
435
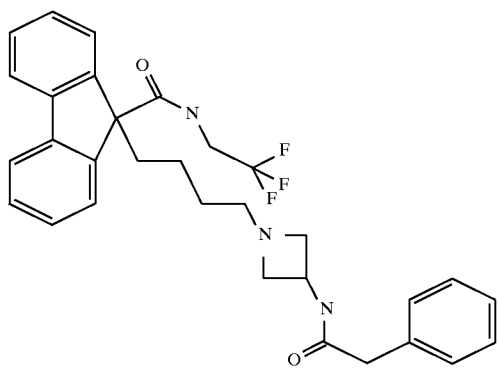
436
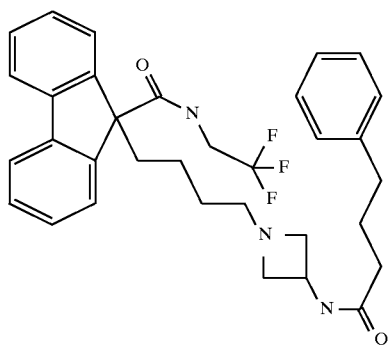

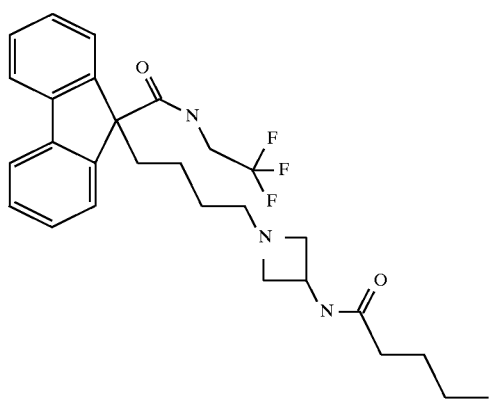
437
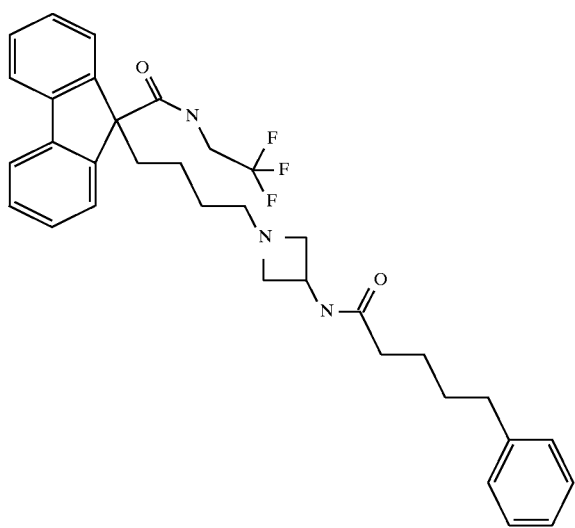
438
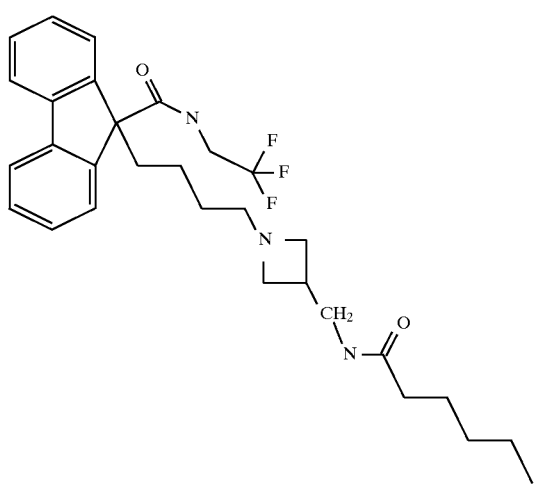
439

-continued
440
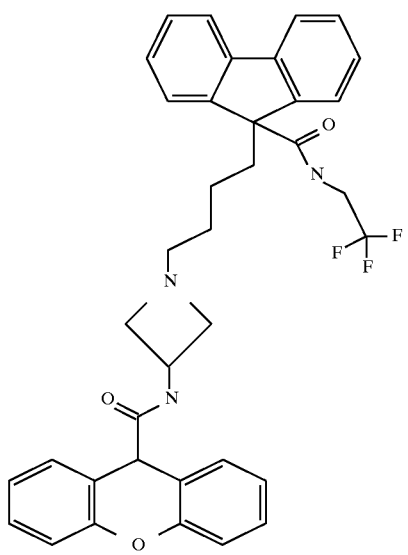
441
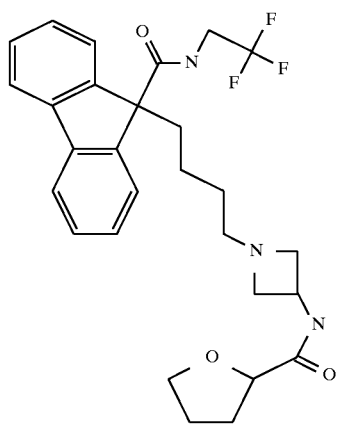
442
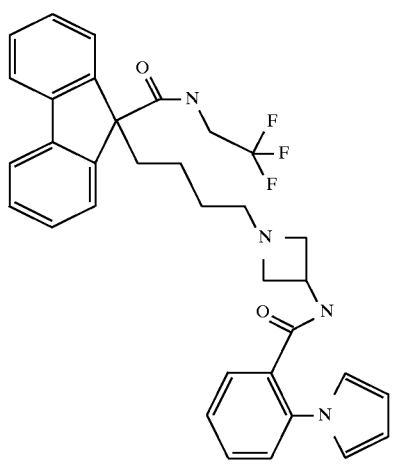

443
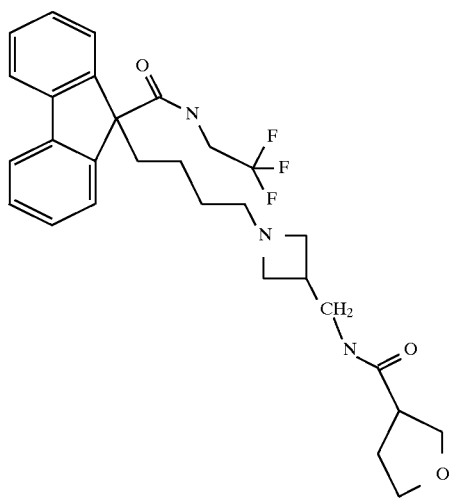
444
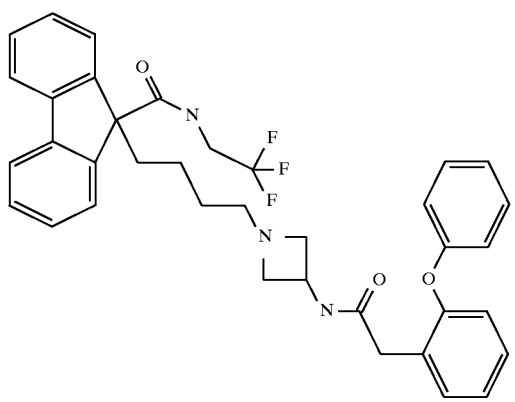
445
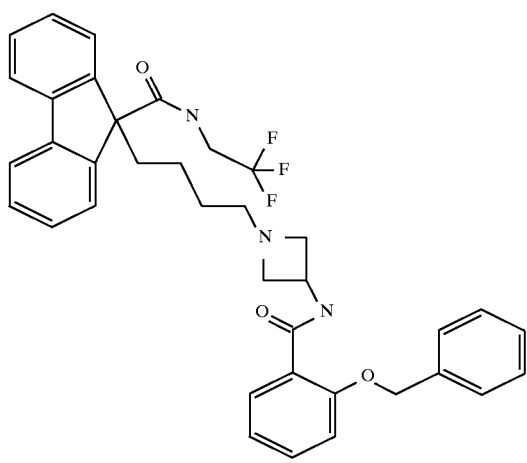

-continued
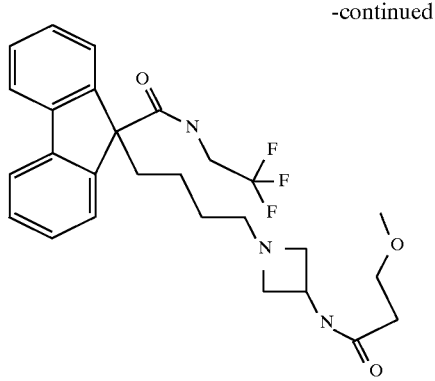
446
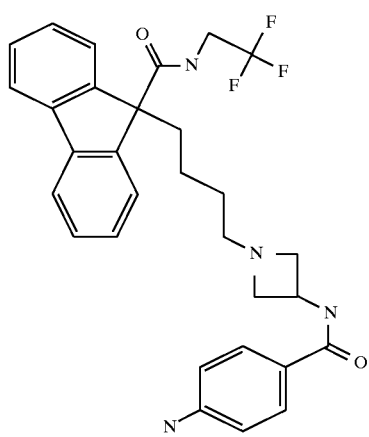
447
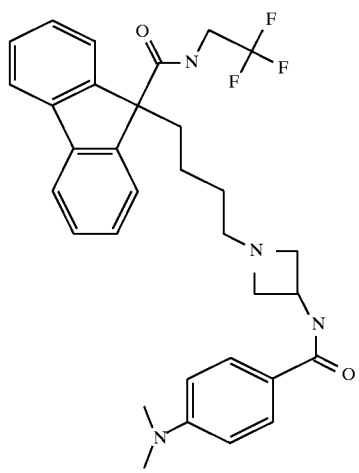
448
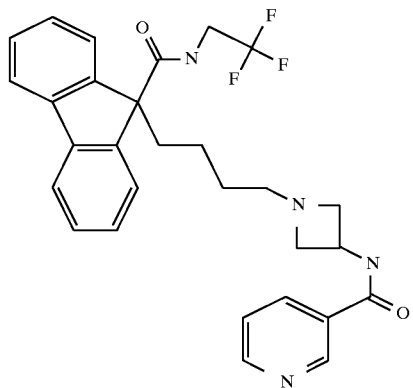
449

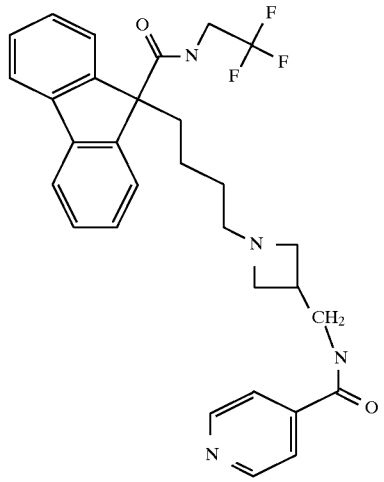
450
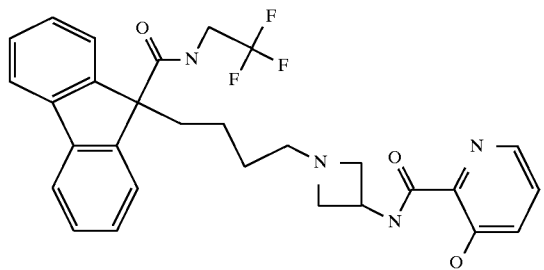
451
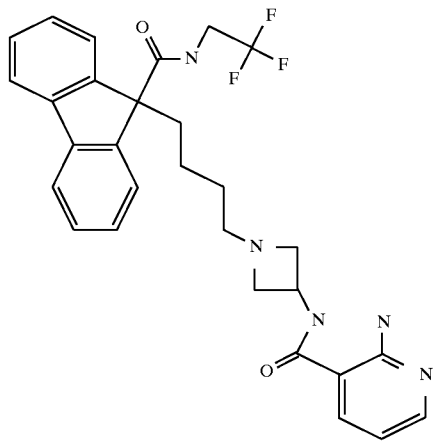
452
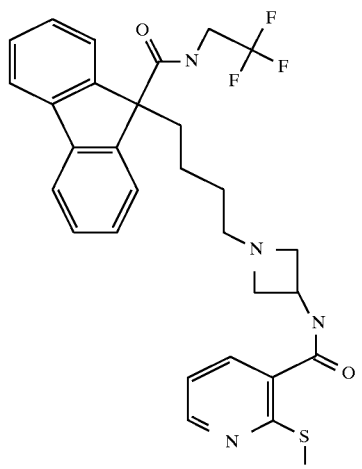
453

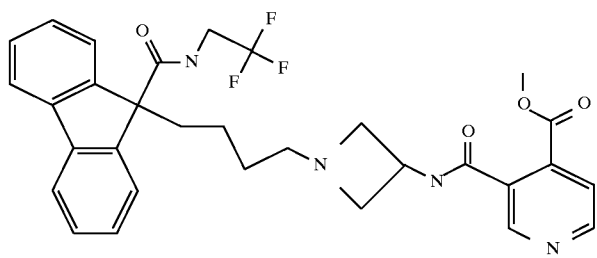
454
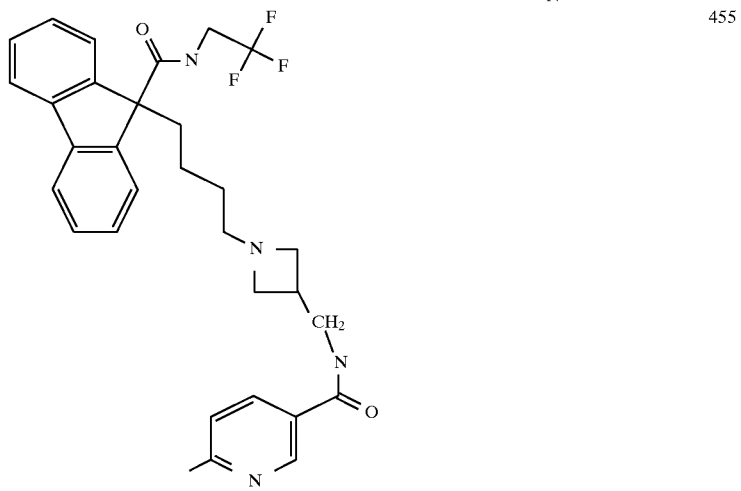
455
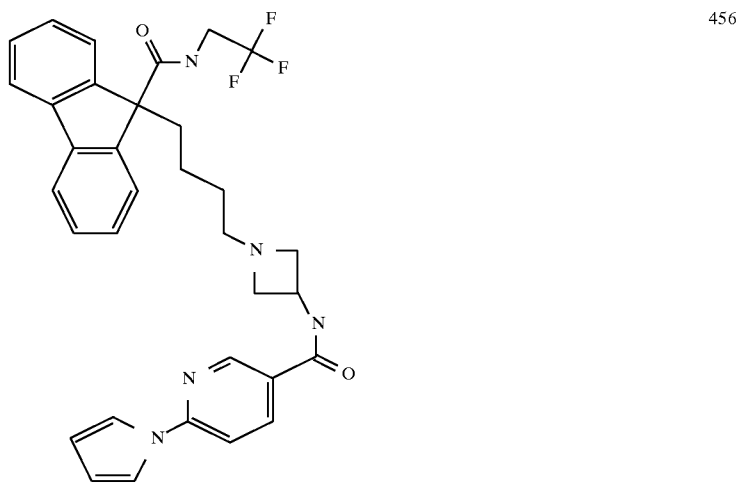
456
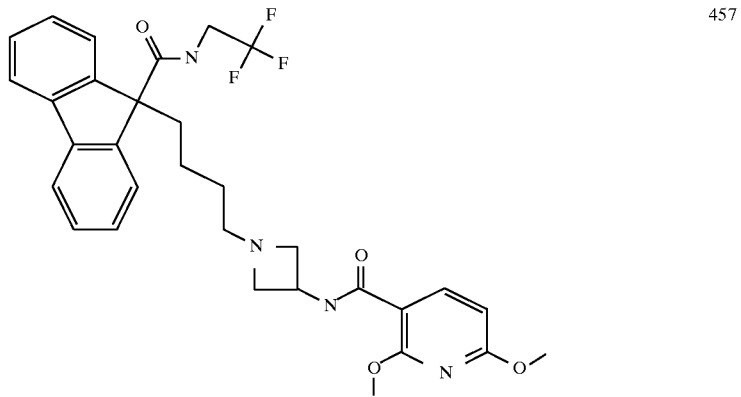
457

458
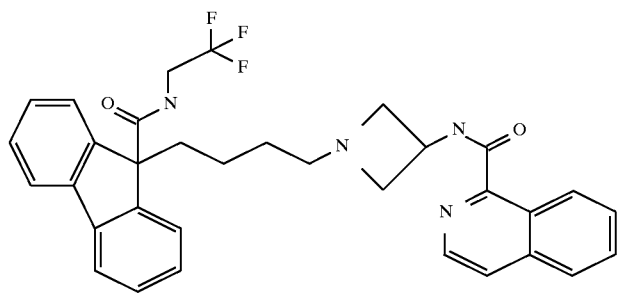
459
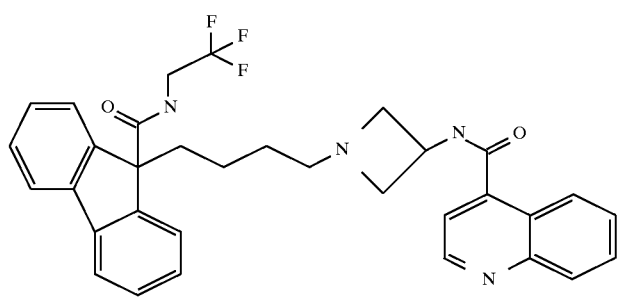
460
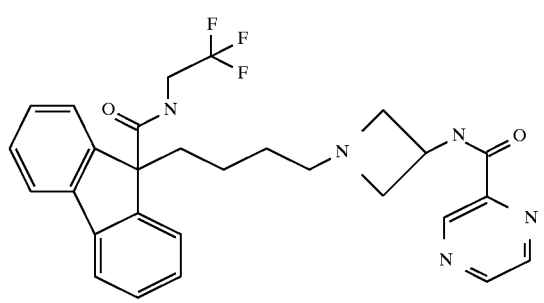
461
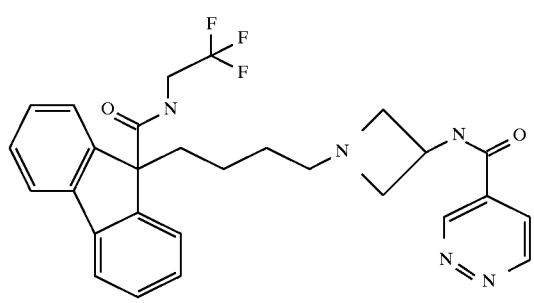
462
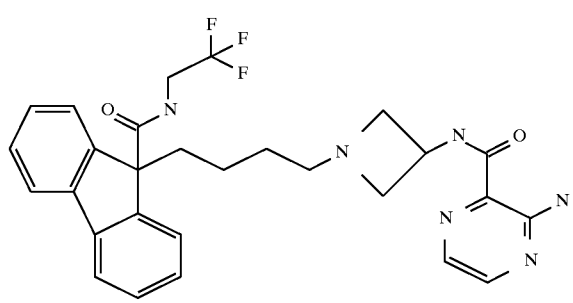

462
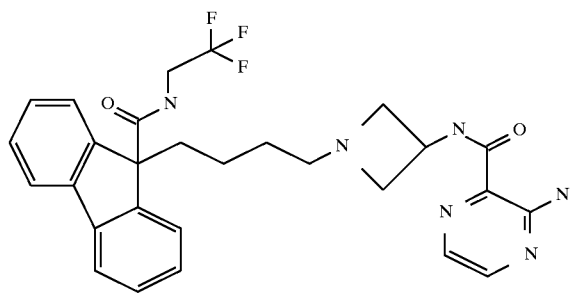
463
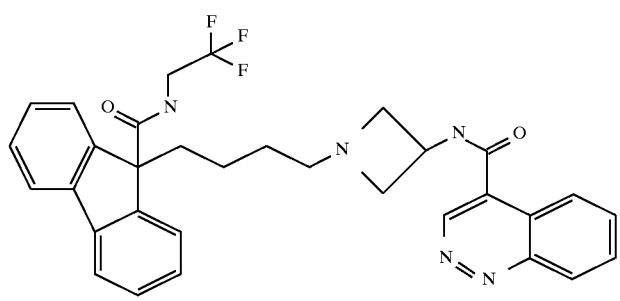
464
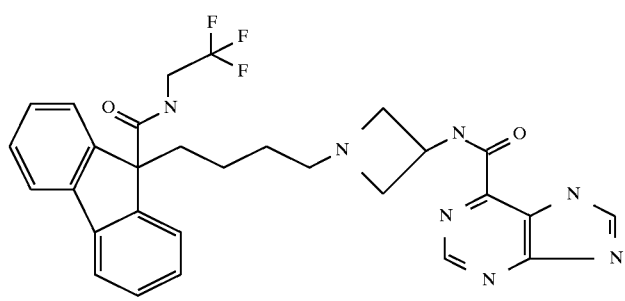
465
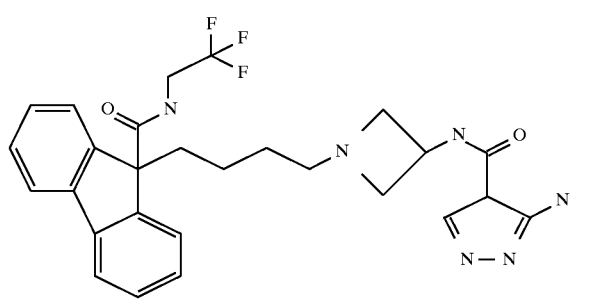
466
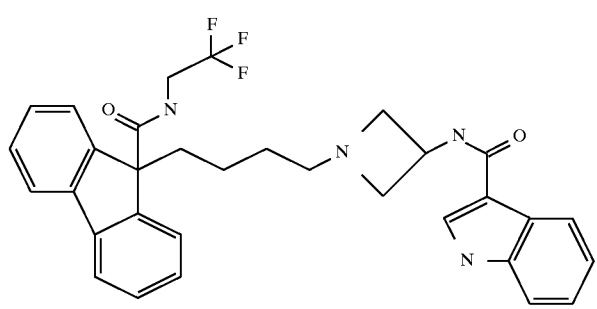

467
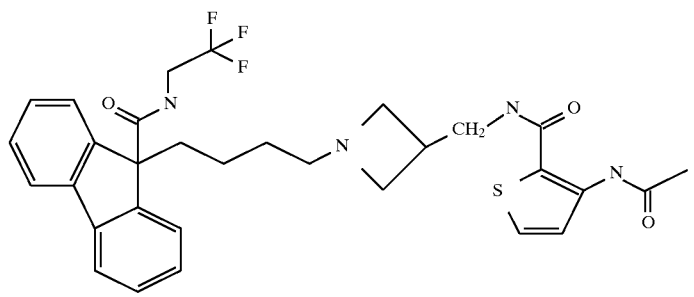
468
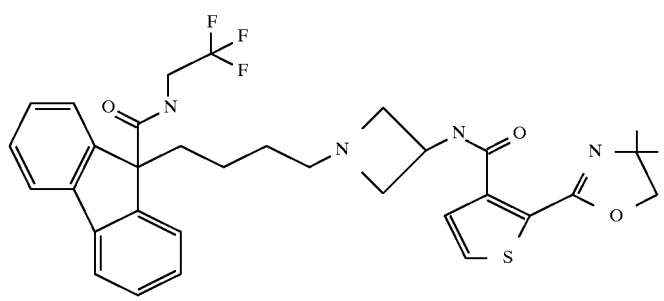
469
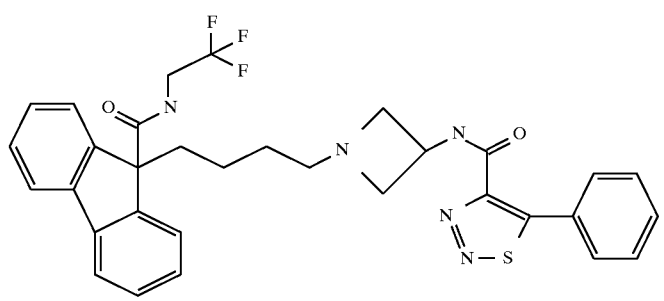
470
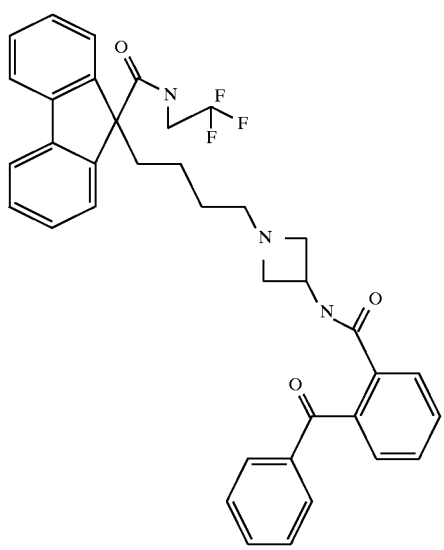

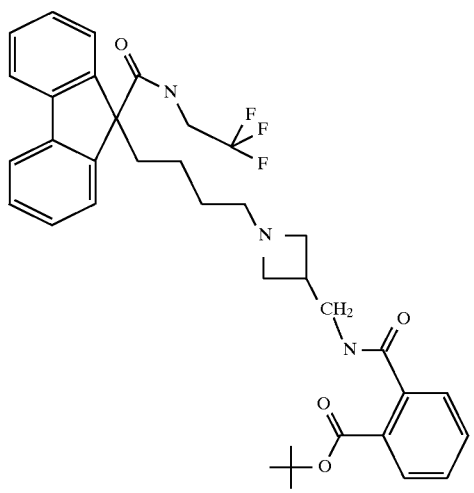
471
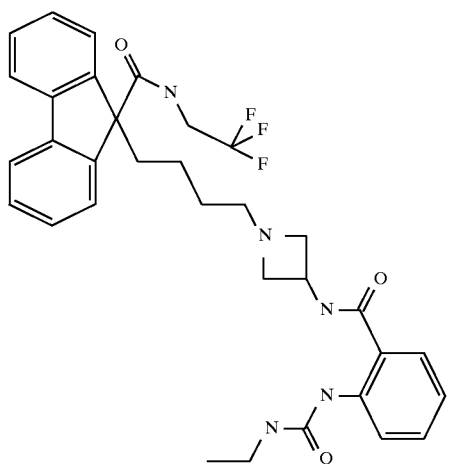
472
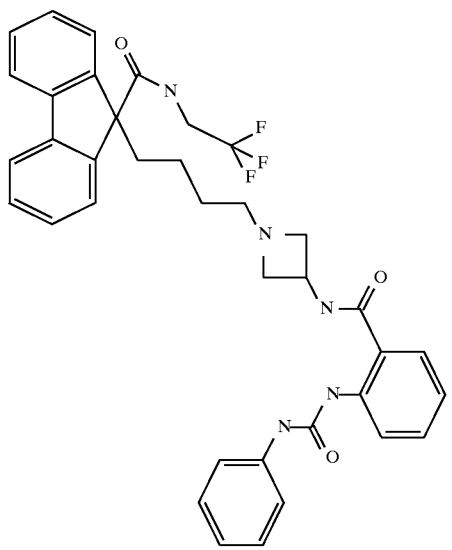
473

474
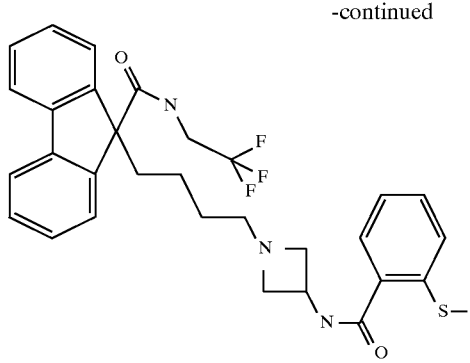
475
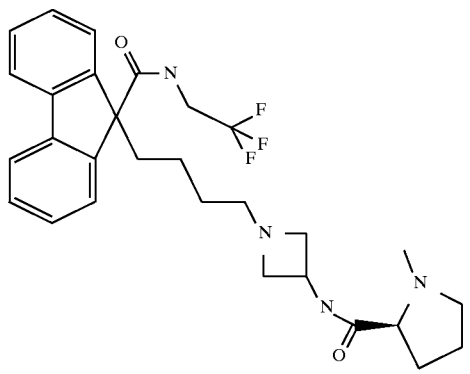
EXAMPLE 476
9-[4-[3-[(Phenoxycarbonyl)amino]-1-azetidinyl]-butyl]-N-(2,2,2-trifluoroethyl)-9H-fluorene-9-carboxamide, monohydrochloride
What is claimed is:
1. A compound which has the structure
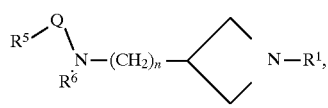
where Q is
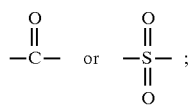
$R^1$ is a fluorenyl-type group of the structure
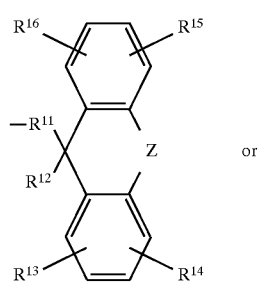
A
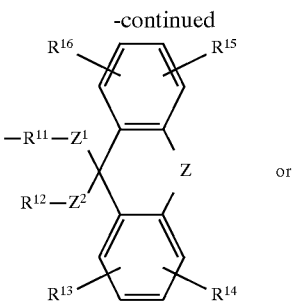
B
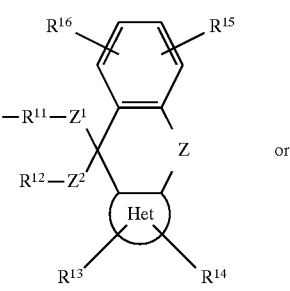
C
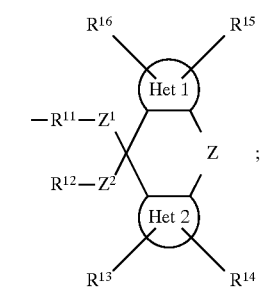
D $R^1$ is an indenyl-type group of the structure

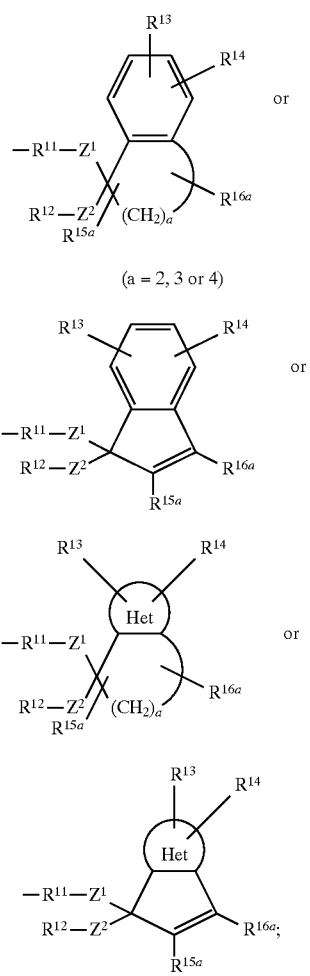

$Z^1$ and $Z^2$ are the same or different and are independently a bond, O, S,

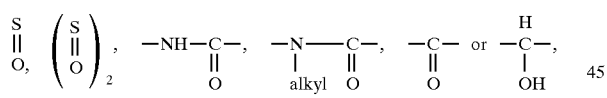

with the proviso that with respect to B, at least one of $Z^1$ and $Z^2$ will be other than a bond; $R^{11}$ is alkylene, alkenylene or alkynylene of up to 10 carbon atoms; arylene or mixed arylene-alkylene; $R^{12}$ is hydrogen, alkyl, alkenyl, aryl, haloalkyl, trihaloalkyl, trihaloalkylalkyl, heteroaryl, heteroarylalkyl, arylalkyl, arylalkenyl, cyclo-alkyl, aryloxy, alkoxy, arylalkoxy or cycloalkyl-alkyl, with the provisos that (1) when $R^{12}$ is H, aryloxy, alkoxy or arylalkoxy, then $Z^2$ is

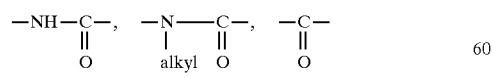

or a bond and (2) when $Z^2$ is a bond, $R^{12}$ cannot be heteroaryl or heteroarylalkyl;

Z is bond, O, S, N-alkyl, N-aryl, or alkylene or alkenylene from 2 to 5 carbon atoms; $R^{13}$, $R^{14}$, $R^{15}$, and $R^{16}$ are independently hydrogen, alkyl, halo, haloalkyl, aryl, cycloalkyl, cyclo-heteroalkyl, alkenyl, alkynyl, hydroxy, alkoxy, nitro, amino, thio, alkylsulfonyl, arylsulfonyl, alkylthio, arylthio, aminocarbonyl, alkylcarbonyloxy, arylcarbonylamino, alkylcarbonylamino, arylalkyl, heteroaryl, heteroarylalkyl or aryloxy;

$R^{15a}$ and $R^{16a}$ are independently hydrogen, alkyl, halo, haloalkyl, aryl, cycloalkyl, cycloheteroalkyl, alkenyl, alkynyl, alkoxy, alkylsulfonyl, arylsulfonyl, alkylthio, arylthio, aminocarbonyl, alkylcarbonyloxy, arylcarbonylamino, alkylcarbonylamino, arylalkyl, heteroaryl, heteroarylalkyl, or aryloxy;

$R^5$ is independently alkyl, alkenyl, alkynyl, aryl, alkoxy, aryloxy, arylalkoxy, heteroaryl, arylalkyl, heteroarylalkyl, cycloalkyl, cycloalkylalkyl, polycycloalkyl, polycycloalkylalkyl, cycloalkenyl, cycloheteroalkyl, heteroaryloxy, cycloalkenylalkyl, polycycloalkenyl, polycycloalkenylalkyl, heteroarylcarbonyl, amino, alkylamino, arylamino, heteroarylamino, cycloalkyloxy, cycloalkylamino, all optionally substituted through available carbon atoms with 1, 2, 3 or 4 groups selected from hydrogen, halo, alkyl, haloalkyl, alkoxy, haloalkoxy, alkenyl, alkynyl, cycloalkyl, cycloalkylalkyl, cycloheteroalkyl, cycloheteroalkylalkyl, aryl, heteroaryl, arylalkyl, arylcycloalkyl, arylalkenyl, arylalkynyl, aryloxy, aryloxyalkyl, arylalkoxy, arylazo, heteroaryloxo, heteroarylalkyl, heteroarylalkenyl, heteroaryloxy, hydroxy, nitro, cyano, amino, substituted amino, thiol, alkylthio, arylthio, heteroarylthio, arylthioalkyl, alkylcarbonyl, arylcarbonyl, arylaminocarbonyl, alkoxycarbonyl, aminocarbonyl, alkynylaminocarbonyl, alkylaminocarbonyl, alkenylaminocarbonyl, alkylcarbonyloxy, arylcarbonyloxy, alkylcarbonylamino, arylcarbonylamino, arylsulfinyl, arylsulfinylalkyl, arylsulfonyl, alkylsulfonyl, arylsulfonylamino, heteroarylcarbonylamino, heteroarylsulfinyl, heteroarylthio, heteroarylsulfonyl, alkylsulfinyl;

$R^6$ is hydrogen or $C_1$–$C_4$ alkyl or $C_1$–$C_4$ alkenyl; all optionally substituted with 1, 2, 3 or 4 groups which may independently be any of the substituents listed in the definition of $R^5$ set out above;

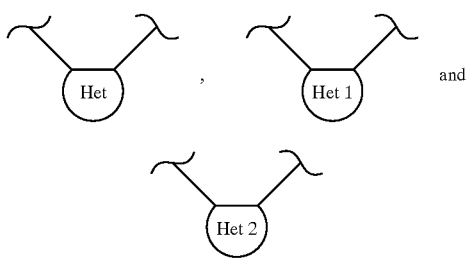

are the same or different and are independently selected from heteroaryl containing 5- or 6-ring members; or an N-oxide

thereof; a stereoisomer thereof; or a pharmaceutically acceptable salt thereof.

2. The compound as defined in claim 1 having the formula

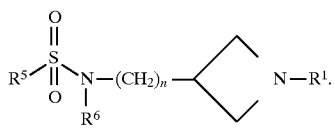

3. The compound as defined in claim 1 having the formula

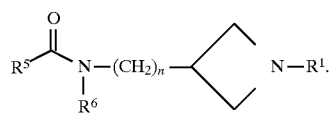

4. The compound as defined in claim 1 wherein $R^1$ is

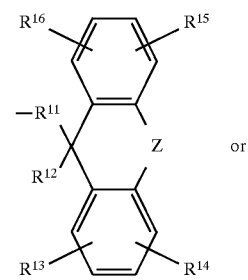
A

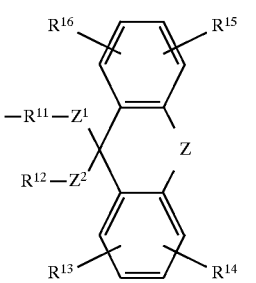
B

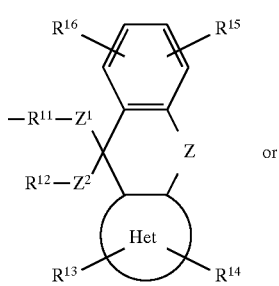
C

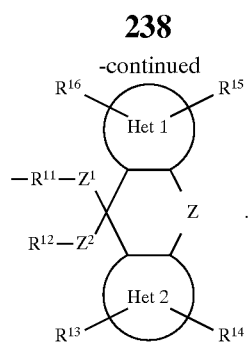
D

5. The compound as defined in claim 4 wherein $R^1$ is

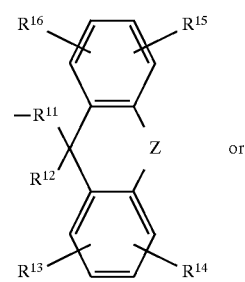
A

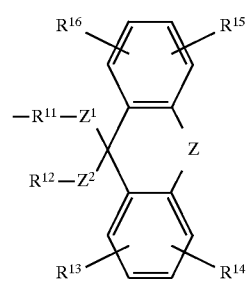
B

Z is a bond, O or S;
$R^{13}$, $R^{14}$, $R^{15}$ and $R^{16}$ are each H or one of $R^{15}$ and $R^{16}$ and one of $R^{13}$ and $R^{14}$ are halogen;
$z^1$ is a bond or C=O;
$R^{11}$ is alkylene or alkenylene;
$R^{12}$—$Z^2$ is

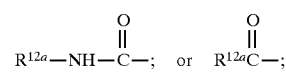

$R^{12a}$ is alkyl, fluorinated lower alkyl or polyfluorinated lower alkyl.

6. The compound as defined in claim 1 wherein $R^1$ is

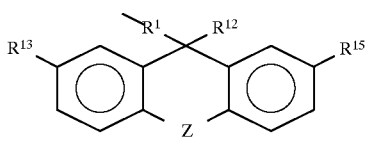

where $R^{11}$ is alkylene or alkenylene; $R^{12}$ is H, alkyl, alkenyl, aralkyl, aralkenyl; and $R^{13}$ is H or F; and $R^{15}$ is H or F; Z is O, S or a bond.

7. The compound as defined in claim 1 wherein $R^1$ is an indenyl-type group of the structure

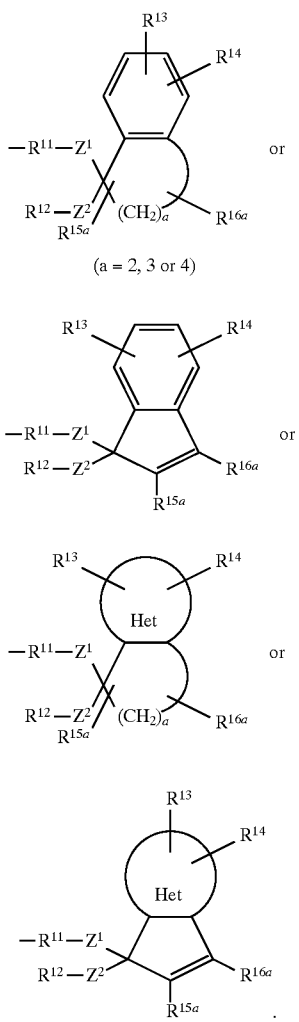

(a = 2, 3 or 4)

8. The compound as defined in claim 1 having the structure

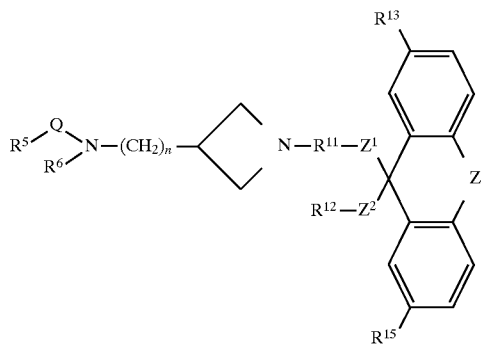

where Q is

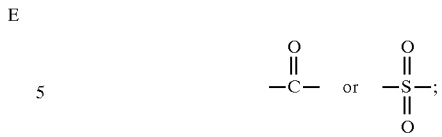

Z is a bond, O or S;

where $R^5$ is cycloalkyl, phenyl, aryl, heteroaryl, or cycloalkyl, phenyl, aryl or heteroaryl, independently substituted at the ortho position with alkyl, alkoxy, haloalkyl (optionally substituted with up to 5 halogens), trifluoro-methyl, aryl, aryloxy, haloalkoxy (optionally substituted with up to 5 halogens), arylalkyl or arylalkoxy;

$R^6$ is H or $CH_3$;

$R^{13}$ and $R^{15}$ are independently H or F;

$Z^1$ is a bond;

$R^{11}$ is alkylene;

$R^{12}$—$Z^2$ is

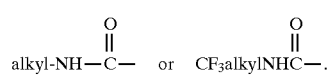

9. The compound as defined in claim 8 wherein $R^{11}$ is —$(CH_2)_4$—, $Z^1$ is a bond, and $R^{12}$—$Z^2$ is

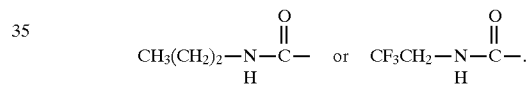

10. The compound as defined in claim 8 having the structure

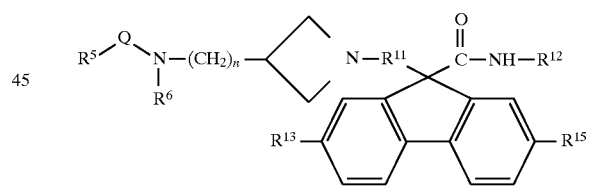

and $R^{12}$ is trifluoromethylalkyl or alkyl.

11. The compound as defined in claim 8 having the structure

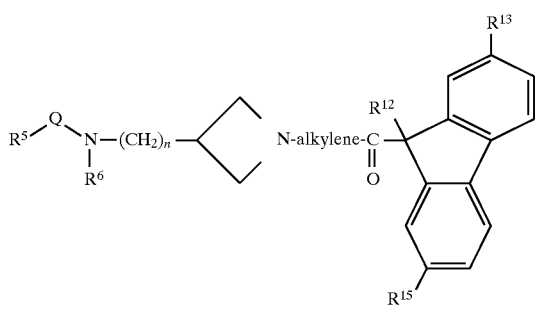

where $R^{12}$ is alkyl.

12. The compound as defined in claim 1 having the structure

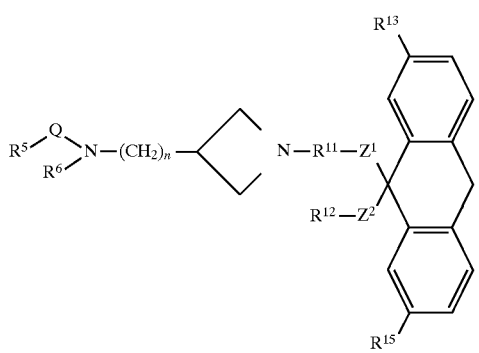

where Q is

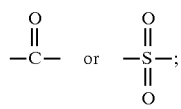

where $R^5$ is cycloalkyl, phenyl, aryl, heteroaryl, or cycloalkyl, phenyl, aryl or heteroaryl, independently substituted at the ortho position with alkyl, alkoxy, haloalkyl (optionally substituted with up to 5 halogens), trifluoromethyl, aryl, aryloxy, haloalkoxy (optionally substituted with up to 5 halogens), arylalkyl or arylalkoxy;

$R^6$ is H or $CH_3$;
$R^{13}$ and $R^{15}$ are independently H or F;
$Z^1$ is a bond;
$R^{11}$ is alkylene;
$R^{12}$—$Z^2$ is

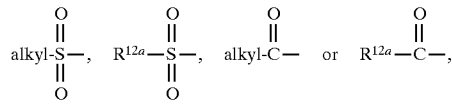

$R^{12a}$ is alkyl, fluorinated lower alkyl or polyfluorinated lower alkyl, or $Z^2$ is a bond and $R^{12}$ is alkyl.

13. The compound as defined in claim 1 which is
N-(2,2,2-trifluoroethyl)-9-[5-[3-[[[4'-(trifluoromethyl)[1,1'-biphenyl]-2-yl]carbonyl]amino]-1-azetidinyl]pentyl]-9H-fluorene-9-carboxamide, 9-[5-[3-(benzoylamino)-1-azetidinyl]pentyl]-N-(2,2,2-trifluoroethyl)-9H-fluorene-9-carboxamide, N-(2,2,2-trifluoroethyl)-9-[4-[3-[[[[4'-(trifluoromethyl)[1,1'-biphenyl]-3-yl]carbonyl]-amino]methyl]-1-azetidinyl]butyl]-9H-fluorene-9-carboxamide, 9-[4-[3-[(benzoylamino)methyl]-1-azetidinyl]-butyl]-N-(2,2,2-trifluoroethyl)-9H-fluorene-9-carboxamide, N-(2,2,2-trifluoroethyl)-9-[4-[3-[[[4'-(trifluoromethyl)[1,1'-biphenyl]-2-yl]carbonyl]-amino]-1-azetidinyl]butyl]-9H-fluorene-9-carboxamide, 9-[4-[3-(benzoylamino)-1-azetidinyl]butyl]-N-(2,2,2-trifluoroethyl)-9H-fluorene-9-carboxamide, or a pharmaceutically acceptable salt thereof.

14. A method for or treating atherosclerosis, pancreatitis or obesity responsive to a decrease in MTP activity in a patient, which comprises administering to a patient in need of treatment a MTP activity decreasing amount of a compound as defined in claim 1.

15. A method of lowering serum lipid levels, cholesterol and/or triglycerides, or treating hyperlipemia, hyperlipidemia, hyperlipoproteinemia, hypercholes-terolemia and/or hypertriglyceridemia responsive to a decreasing MTP activity in a patient, which comprises administering to a patient in need of treatment a MTP activity decreasing amount of a compound as defined in claim 1.

* * * * *